(12) United States Patent
Nakatsuru et al.

(10) Patent No.: US 10,695,746 B2
(45) Date of Patent: Jun. 30, 2020

(54) WATER ABSORBENT AGENT

(71) Applicant: NIPPON SHOKUBAI CO., LTD., Osaka-shi, Osaka (JP)

(72) Inventors: Reiko Nakatsuru, Himeji (JP); Kazuki Kimura, Himeji (JP)

(73) Assignee: NIPPON SHOKUBAI CO., LTD., Osaka-shi, Osaka (JP)

( * ) Notice: Subject to any disclaimer, the term of this patent is extended or adjusted under 35 U.S.C. 154(b) by 374 days.

(21) Appl. No.: 15/541,845

(22) PCT Filed: Dec. 28, 2015

(86) PCT No.: PCT/JP2015/086474
§ 371 (c)(1),
(2) Date: Jul. 6, 2017

(87) PCT Pub. No.: WO2016/111223
PCT Pub. Date: Jul. 14, 2016

(65) Prior Publication Data
US 2018/0001300 A1 Jan. 4, 2018

(30) Foreign Application Priority Data

Jan. 7, 2015 (JP) ................................. 2015-001206

(51) Int. Cl.
| | | |
|---|---|---|
| *B01J 20/26* | (2006.01) |
| *A61L 15/60* | (2006.01) |
| *A61F 13/49* | (2006.01) |
| *A61F 13/53* | (2006.01) |
| *B01J 20/28* | (2006.01) |
| *B01J 20/30* | (2006.01) |
| *A61L 15/24* | (2006.01) |
| *G01N 5/02* | (2006.01) |

(52) U.S. Cl.
CPC ............ *B01J 20/267* (2013.01); *A61F 13/49* (2013.01); *A61F 13/53* (2013.01); *A61L 15/24* (2013.01); *A61L 15/60* (2013.01); *B01J 20/26* (2013.01); *B01J 20/28* (2013.01); *B01J 20/28004* (2013.01); *B01J 20/30* (2013.01); *B01J 20/3021* (2013.01); *B01J 20/3085* (2013.01); *G01N 5/025* (2013.01)

(58) Field of Classification Search
CPC ...... B01J 20/26; B01J 20/267; B01J 20/3021; B01J 20/3085; A61L 15/24; A61L 15/60; G01N 5/025
USPC ........................................................ 423/401
See application file for complete search history.

(56) References Cited

U.S. PATENT DOCUMENTS

| | | |
|---|---|---|
| 5,118,719 A | 6/1992 | Lind |
| 5,154,713 A | 10/1992 | Lind |
| 6,107,358 A | 8/2000 | Harada et al. |
| 2002/0128618 A1 | 9/2002 | Frenz et al. |
| 2003/0181115 A1 | 9/2003 | Nagasuna et al. |
| 2007/0207924 A1 | 9/2007 | Ikeuchi et al. |
| 2011/0313113 A1 | 12/2011 | Sakamoto et al. |
| 2012/0258851 A1 † | 10/2012 | Nakatsuru |
| 2013/0026412 A1 | 1/2013 | Machida et al. |
| 2013/0101851 A1 | 4/2013 | Takaai et al. |
| 2014/0296465 A1 | 10/2014 | Sakamoto et al. |
| 2014/0312273 A1 | 10/2014 | Wattebled et al. |
| 2015/0259494 A1 | 9/2015 | Takaai et al. |
| 2016/0332141 A1 | 11/2016 | Machida et al. |

FOREIGN PATENT DOCUMENTS

| | | |
|---|---|---|
| JP | 5-237378 | 9/1993 |
| JP | 2003-290290 A | 10/2003 |
| JP | 2007-529295 A | 10/2007 |
| JP | 2014-98172 A | 5/2014 |
| WO | WO-1992/018171 A1 | 10/1992 |
| WO | WO-2005/097313 A1 | 10/2005 |
| WO | WO-2006/082197 A1 | 8/2006 |
| WO | WO-2008/026783 A1 | 3/2008 |
| WO | WO-2010/095427 A1 | 8/2010 |
| WO | WO-2011/040530 A1 | 4/2011 |
| WO | WO-2011/078298 A1 | 6/2011 |
| WO | WO-2011/126079 A1 | 10/2011 |
| WO | WO-2013/072268 A1 | 5/2013 |

OTHER PUBLICATIONS

Partial Supplementary European Search Report dated Jul. 4, 2018 issued in European Patent Application No. 15877095.8.
International Preliminary Report on Patentability dated Jul. 20, 2017 issued in International Patent Application No. PCT/JP2015/086474.
International Search Report dated Mar. 22, 2016 issued in International Patent Application No. PCT/JP2015/086474.

† cited by third party

*Primary Examiner* — Edward M Johnson
(74) *Attorney, Agent, or Firm* — Harness Dickey & Pierce P.L.C.

(57) ABSTRACT

Provided is a water-absorbing agent which maintains a certain degree of liquid permeability and water absorption speed while also reducing re-wet in a disposable diaper, without the use of costly raw materials or costly apparatuses. The water-absorbing agent of the present invention contains a polyacrylic acid salt-based water-absorbing resin as a main component and has physical properties falling within a specific range, the physical properties being saline flow conductivity (SFC), gap fluid retention property under pressure, and a proportion of particles having a particle diameter of not less than 150 μm and less than 710 μm.

10 Claims, 6 Drawing Sheets

WATER ABSORBENT AGENT

PRIORITY STATEMENT

This application is a national stage application under 35 U.S.C. § 371 of PCT International Application No. PCT/JP/2015/086474 which has an International filing date of 28 Dec. 2015 and claims priority to Japanese Patent Application No. JP 2015-001206 which has a filing date of 7 Jan. 2015. The contents of each application recited above are incorporated herein by reference in their entirety.

TECHNICAL FIELD

The present invention relates to a water-absorbing agent and a method for producing the water-absorbing agent. More specifically, the present invention relates to a water-absorbing agent containing a polyacrylic acid (salt)-based water-absorbing resin as a main component, the water-absorbing agent being for use in absorbent articles and the like such as disposable diapers and sanitary napkins, the water-absorbing agent having excellent water absorption performance. The present invention also relates to a method for producing such a water-absorbing agent. The present invention also relates to a method for evaluating liquid release performance of a water-absorbing agent and a method for measuring space between gel particles.

BACKGROUND ART

Water-absorbing resin (super absorbent polymer or SAP) is a water-swellable, water-insoluble polymer gelling agent. Water-absorbing resin is widely used in various fields, including use in absorbent articles such as disposable diapers and sanitary napkins, agricultural and horticultural water retaining agents, industrial waterproofing agents and the like.

Many monomers and/or hydrophilic polymers are used as raw materials for water-absorbing resin. A polyacrylic acid (salt)-based water-absorbing resin containing acrylic acid and/or a salt thereof as a monomer is industrially produced in the largest amount, due to its water absorption performance.

Disposable diapers, which are one of the main applications of water-absorbing resin, have undergone advances in terms of performance. Along with these advances have come requirements for various functions (enhanced physical properties) of water-absorbing resin. Specifically, the water-absorbing resin is required to have, in addition to basic physical properties such as fluid retention capacity without pressure and fluid retention capacity under pressure, a variety of physical properties such as gel strength, water-soluble component, moisture content, water absorption speed, liquid permeability, particle size distribution, urine resistance, antibacterial property, damage resistance, powder fluidity, deodorant property, low coloring property, low dustiness, and low monomer residue.

Of the physical properties mentioned above, the liquid permeability is becoming a more important in view of an increase in the amount of water-absorbing resin used per disposable diaper. Proposed techniques for enhancing the liquid permeability include, for example, a technique of adding a spacer (Patent Literature 1) and a technique of using polyamine and either a polyvalent metal cation or polyvalent anion (Patent Literature 2). Proposed parameters relating to liquid permeability include, for example, pressurized void average radius index (Patent Literature 3) and wet porosity (Patent Literature 4).

Water absorption speed is also an important physical property of water-absorbing resin. Methods for increasing the water absorption speed include, for example, increasing the specific surface area of a water-absorbing resin. Specifically, proposed techniques include, for example, a technique of setting the particle diameter of a water-absorbing resin to be minute (Patent Literature 5) and a technique of foaming polymerization (Patent Literatures 6 and 7).

Note that liquid permeability and water absorption speed are physical properties having an inverse relationship. If one is improved, the other is impaired. In recent years, however, there have been proposed techniques for improving one without impairing the other, or for improving both. Specifically, proposed techniques include, for example, improved techniques for use in foaming polymerization (Patent Literatures 8 to 10) and improved techniques for use during gel-crushing (Patent Literature 11).

CITATION LIST

Patent Literature

[Patent Literature 1]
  Specification of U.S. Patent Application Publication No. 2002/0128618
[Patent Literature 2]
  Pamphlet of International Publication No. WO 2006/082197
[Patent Literature 3]
  Pamphlet of International Publication No. WO 2008/026783
[Patent Literature 4]
  Pamphlet of International Publication No. WO 2005/097313
[Patent Literature 5]
  Pamphlet of International Publication No. WO 92/018171
[Patent Literature 6]
  Specification of U.S. Pat. No. 5,154,713
[Patent Literature 7]
  Specification of U.S. Pat. No. 6,107,358
[Patent Literature 8]
  Pamphlet of International Publication No. WO 2010/095427
[Patent Literature 9]
  Pamphlet of International Publication No. WO 2011/078298
[Patent Literature 10]
  Pamphlet of International Publication No. WO 2013/072268
[Patent Literature 11]
  Pamphlet of International Publication No. WO 2011/126079

SUMMARY OF INVENTION

Technical Problem

As described above, to date there have been numerous improved techniques proposed for the purpose of improving the performance of water-absorbing resin. Liquid permeability in particular is important as a physical property of water-absorbing resin, and there have been a great number of improved techniques proposed for enhancing this physical property other than the techniques described above.

Using such water-absorbing resins having improved liquid permeability in an absorbent article such as a disposable diaper or the like makes it possible to improve a diffusion property and an absorption speed of the disposable diaper. Such water-absorbing resins have not, however, improved "re-wet," another important function.

Functions required of absorbent articles such as disposable diapers are many and varied, and are becoming more advanced. As such, there is now the demand for techniques to maintain a certain degree of liquid permeability while also reducing re-wet in a disposable diaper.

An object of the present invention lies in providing a water-absorbing agent which maintains a certain degree of liquid permeability and water absorption speed while also reducing re-wet in a disposable diaper, without the use of costly raw materials or costly apparatuses.

Solution to Problem

In order to attain the above object, the inventors conducted diligent research and were the first to focus on the fact that a gap fluid retention property in a swollen gel particle layer under pressure (hereinafter referred to as "gap fluid retention property under pressure"), which is a parameter which had heretofore been overlooked, contributes to reduction of re-wet in a disposable diaper. As a result, the inventors were able to arrive at the present invention upon discovering that controlling the gap fluid retention property under pressure of a water-absorbing agent to be within a certain range makes it possible to attain the above object.

A water-absorbing agent in accordance with the present invention is a water-absorbing agent including: a polyacrylic acid (salt)-based water-absorbing resin as a main component, the water-absorbing agent satisfying (A) to (C) below: (A) a saline flow conductivity (SFC) is not less than $20 \times 10^{-7} \cdot cm^3 \cdot s \cdot g^{-1}$; (B) a gap fluid retention property under pressure is not less than 9 g/g; and (C) a proportion of particles having a particle diameter of not less than 150 µm and less than 710 µm is less than 90 weight %, (where, in (B), when a water-absorbing resin is swollen in a 0.69 weight % aqueous sodium chloride solution, the gap fluid retention property under pressure is a weight of the aqueous sodium chloride solution per gram of the absorbing agent, the sodium chloride solution being retained in gaps within the water-absorbing agent under a load of 2.07 kPa).

A first method for producing the above water-absorbing agent is a method for producing a water-absorbing agent containing a polyacrylic acid (salt)-based water-absorbing resin as a main component, including the steps of: (1) preparing an aqueous monomer solution containing acrylic acid (salt) as a main monomer component, the step (1) including at least one of the following steps: (a) introducing, into the aqueous monomer solution, a gas in an amount of not less than 0.0015 ml of the gas per gram of the aqueous monomer solution; (b) causing gas bubbles to be created and contained in the aqueous monomer solution by decreasing a solubility of dissolved gas in the aqueous monomer solution; and (c) adding, to the aqueous monomer solution, a foaming agent in an amount of not more than 5 weight % relative to solid content of a below-mentioned water-absorbing resin powder; (2) subjecting the aqueous monomer solution obtained in the step (1) to foaming polymerization in the presence of a foaming agent and/or gas bubbles so that a crosslinked hydrogel polymer is obtained; (3) grain-refining the crosslinked hydrogel polymer during or after the foaming polymerization by use of a motive power having a gel-grinding energy 2 (GGE2) of 7 J/g to 40 J/g; (4) drying the crosslinked hydrogel polymer after the foaming polymerization so that a dried polymer is obtained; (5) pulverizing and classifying the dried polymer after drying so that a water-absorbing resin powder is obtained; and (6) surface-crosslinking the water-absorbing resin powder.

A second method for producing the above water-absorbing agent is a method for producing a water-absorbing agent containing a polyacrylic acid (salt)-based water-absorbing resin as a main component, including the steps of: (1) preparing an aqueous monomer solution containing acrylic acid (salt) as a main monomer component, the step (1) including at least one of the following steps: (a) introducing, into the aqueous monomer solution, a gas in an amount of not less than 0.0015 ml of the gas per gram of the aqueous monomer solution; (b) causing gas bubbles to be created and contained in the aqueous monomer solution by decreasing a solubility of dissolved gas in the aqueous monomer solution; and (c) adding, to the aqueous monomer solution, a foaming agent in an amount of not more than 5 weight % relative to solid content of a below-mentioned water-absorbing resin powder; (2) subjecting the aqueous monomer solution obtained in the step (1) to foaming polymerization in the presence of a foaming agent and/or gas bubbles so that a crosslinked hydrogel polymer is obtained; (3') grain-refining the crosslinked hydrogel polymer during or after the step (2) by use of a motive power having a gel-grinding energy 2 (GGE2) of not less than 7 J/g and less than 18 J/g; (4) drying a grain-refined crosslinked hydrogel polymer obtained in the step (3') so that a dried polymer is obtained; (5) pulverizing and classifying the dried polymer obtained in the step (4) so that a water-absorbing resin powder is obtained; (6) surface-crosslinking the water-absorbing resin powder, obtained through the steps (1) through (5) and having a BET specific surface area of not less than 0.0270 $m^2$/g and less than 0.0310 $m^2$/g, so that water-absorbing resin particles are obtained; and (7) adding, to the water-absorbing resin particles obtained in the step (6), a liquid permeability improving agent in the amounts of (I) through (III) below: (I) in a case where the liquid permeability improving agent is a polyvalent metal cation, an amount such that an amount of polyvalent metal atoms is less than $1.40 \times 10^{-5}$ mol/g; (II) less than 2.0 weight %, in a case where the liquid permeability improving agent is a cationic polymer; and (III) (IIIa) less than 0.3 weight %, in a case where the liquid permeability improving agent is inorganic fine particles having a primary particle diameter of less than 20 nm, and (IIIb) less than 1.0 weight %, in a case where the liquid permeability improving agent is inorganic fine particles having a primary particle diameter of not less than 20 nm, each of the amounts of (I) through (III) being a proportion relative to the solid content of the water-absorbing resin powder.

A third method for producing the above water-absorbing agent is a method for producing a water-absorbing agent containing a polyacrylic acid (salt)-based water-absorbing resin as a main component, including the steps of: (1) preparing an aqueous monomer solution containing acrylic acid (salt) as a main monomer component, the step (1) including at least one of the following steps: (a) introducing, into the aqueous monomer solution, a gas in an amount of 0.0015 ml of the gas per gram of the aqueous monomer solution; (b) causing gas bubbles to be created and contained in the aqueous monomer solution by decreasing a solubility of dissolved gas in the aqueous monomer solution; and (c) adding, to the aqueous monomer solution, a foaming agent in an amount of not more than 5 weight % relative to solid content of a below-mentioned water-absorbing resin powder; (2) subjecting the aqueous monomer solution obtained in the step (1) to foaming polymerization in the presence of a foaming agent and/or gas bubbles so that a crosslinked hydrogel polymer is obtained; (3") grain-refining the crosslinked hydrogel polymer during or after the step (2) by use of a motive power having a gel-grinding energy 2 (GGE2) of not less than 18 J/g and not more than 40 J/g; (4) drying a grain-refined crosslinked hydrogel polymer obtained in the step (3") so that a dried polymer is obtained; (5) pulverizing and classifying the dried polymer obtained in the step (4) so that a water-absorbing resin powder is obtained; (6) surface-crosslinking the water-absorbing resin powder, obtained through the steps (1) through (5) and having a BET specific surface area of not less than 0.0310 $m^2/g$, so that water-absorbing resin particles are obtained; and (7) adding, to the water-absorbing resin particles obtained in the step (6), a liquid permeability improving agent in the amounts of (i) through (iii) below: (i) in a case where the liquid permeability improving agent is a polyvalent metal cation, an amount such that an amount of polyvalent metal atoms is less than $3.60 \times 10^{-5}$ mol/g; (ii) less than 2.5 weight %, in a case where the liquid permeability improving agent is a cationic polymer; and (iii) (iiia) less than 1.2 weight %, in a case where the liquid permeability improving agent is inorganic fine particles having a primary particle diameter of less than 20 nm, and (iiib) less than 2.0 weight %, in a case where the liquid permeability improving agent is inorganic fine particles having a primary particle diameter of not less than 20 nm, each of the amounts of (i) through (iii) being a proportion relative to the solid content of the water-absorbing resin powder.

Advantageous Effects of Invention

With the present invention, surface crosslinking is carried out after the BET specific surface area of a water-absorbing resin powder is controlled by foaming polymerization and gel-crushing. This makes it possible to produce a novel water-absorbing agent which is balanced in that it has a high liquid permeability and high water absorption speed while also being able to hold a large amount of liquid between gel particles while under pressure. Using this water-absorbing agent in a disposable diaper makes it possible to reduce re-wet in the disposable diaper.

DESCRIPTION OF EMBODIMENTS

Figure 1:
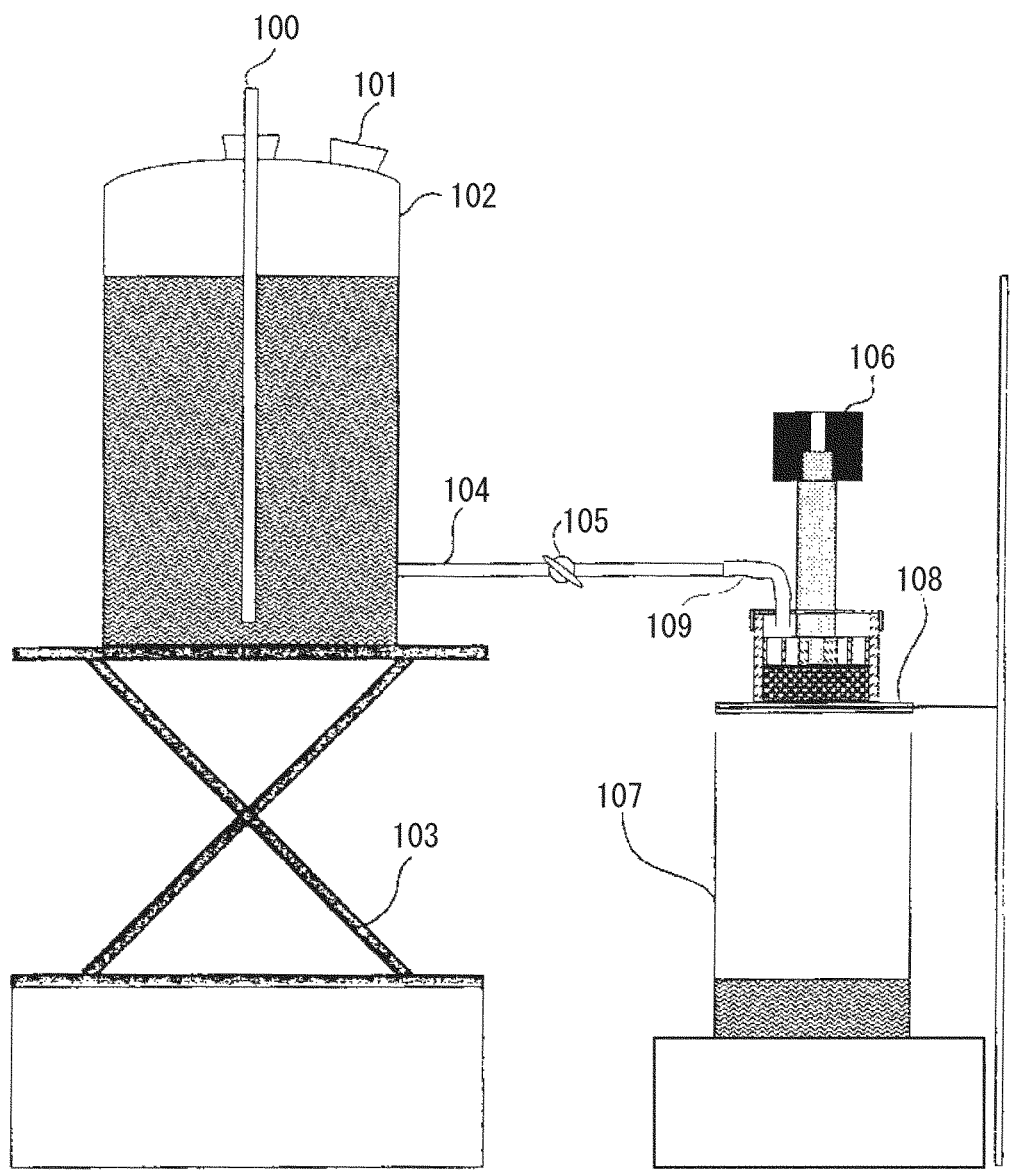
FIG. 1 is a schematic cross-sectional view of a measuring device used for measuring gap fluid retention property under pressure.

The following description will discuss the present invention in detail. The present invention is, however, not limited in scope to the description below, and may be altered from the examples below and practiced as appropriate as long as such alteration is not a departure from the scope of the present invention. The present invention is not limited to the following embodiments, but can be altered by a skilled person in the art within the scope of the claims. The present invention also encompasses, in its technical scope, any embodiment derived by combining technical means disclosed in differing embodiments.

[1] Definitions of Terms (1-1) "Water-Absorbing Resin"

The term "water-absorbing resin" as used herein means a water-swellable and water-insoluble polymer gelling agent that satisfies the following physical properties. Specifically, the term "water-absorbing resin" as used herein means a polymer gelling agent having a centrifuge retention capacity (CRC) of not less than 5 g/g, which is the prescribed definition of "water-swellable" in ERT 441.2-02, and having a water soluble component (Ext) of not more than 50 weight %, which is the prescribed definition of "water-insoluble" in ERT 470.2-02.

The water-absorbing resin can be designed according to its purpose of use and its object, and is not limited to a particular water-absorbing resin. The water-absorbing resin is preferably a hydrophilic crosslinked polymer which has been obtained by crosslinking and polymerizing unsaturated monomers each of which has a carboxyl group. Moreover, the water-absorbing resin does not need to be in a form in which the water-absorbing resin is wholly a crosslinked polymer, and can be a water-absorbing resin composition that contains, for example, an additive to the extent that the abovementioned value ranges of physical properties (CRC and Ext) are satisfied.

The term "water-absorbing resin" as used in the present invention may refer to not only a pre-shipment end product but also an intermediate produced during a process for producing the water-absorbing resin (e.g., a crosslinked hydrogel polymer after polymerization, a dry polymer after drying, a water-absorbing resin powder before surface crosslinking, or the like). All of these (including the above composition) are collectively referred to as the "water-absorbing resin".

Examples of forms the water-absorbing resin include a sheet form, a fiber form, a film form, a particulate form, and a gel form. The water-absorbing resin of the present invention is preferably in a particulate form.

(1-2) "Polyacrylic Acid (Salt)"

The term "polyacrylic acid (salt)" as used herein refers to polyacrylic acid and/or a salt thereof, and means a polymer that contains, as a main component, a repeating unit of acrylic acid and/or a salt thereof (hereinafter referred to as "acrylic acid (salt)") and that contains a graft component as an optional component.

The term "main component" means that the acrylic acid (salt) is used (contained) preferably in an amount of 50 mol %/n to 100 mol %, more preferably of 70 mol % to 100 mol %, even more preferably of 90 mol % to 100 mol %, and especially even more preferably of substantially 100 mol %, relative to a total amount of monomers for use in polymerization (excluding an internal crosslinking agent).

The polyacrylic acid (salt) which is used as a crosslinked polymer includes a water-soluble salt of the polyacrylic acid and preferably includes a monovalent salt, more preferably includes an alkali metal salt or ammonium salt, even more preferably includes an alkali metal salt, and especially even more preferably includes a sodium salt.

(1-3) "EDANA" and "ERT"

The term "EDANA" is an acronym for the European Disposables and Nonwovens Associations. The term "ERT" is an acronym for EDANA Recommended Test Methods, which are European standard (de facto international standard) methods for measuring physical properties of water-absorbing resin. For the present invention, physical properties of water-absorbing resin are measured in conformity with the ERT master copy (2002 revised version) unless otherwise specified.

(a) "CRC" (ERT 441.2-02)

The term "CRC" is an acronym for "centrifuge retention capacity", and refers to a fluid retention capacity without pressure (hereinafter referred to also as "fluid retention capacity") of a water-absorbing resin. Specifically, the CRC refers to a fluid retention capacity (unit; g/g) measured after 0.2 g of a water-absorbing resin contained in a nonwoven fabric bag is immersed in a large excess of a 0.9 weight % aqueous sodium chloride solution for 30 minutes so as to be allowed to freely swell, and then the water-absorbing resin is drained in a centrifuge (250 G) for 3 minutes.

(b) "AAP" (ERT 442.2-02)

The term "AAP" is an acronym for "absorption against pressure", and refers to a fluid retention capacity under pressure of water-absorbing resin. Specifically, "AAP" refers to a fluid retention capacity (unit: g/g) measured after 0.9 g of a water-absorbing resin has been swollen in a large excess of a 0.9 weight % aqueous sodium chloride solution for 1 hour under a load of 21 $g/cm^2$ (2.06 kPa). Note that in some cases the measurement may be carried out under a load of 49 $g/cm^2$ (4.81 kPa). Note also that ERT 442.2-02 uses the term "Absorption Under Pressure", which refers to substantially the same thing as "AAP".

(c) "Ext" (ERT 470.2-02)

The term "Ext" is an abbreviation for "Extractables", and refers to a water-soluble component (water-soluble component amount) of a water-absorbing resin. Specifically, the Ext refers to a dissolved amount (unit: weight %) of a material in an aqueous solution, the dissolved amount being obtained by adding 1.0 g of a water-absorbing resin to 200 ml of a 0.9 weight % aqueous sodium chloride solution and stirring a resultant mixture at 500 rpm for 16 hours. Note that the water-soluble component is measured by pH titration.

(d) "PSD" (ERT 420.2-02)

The term "PSD" is an acronym for "particle size distribution", and refers to a particle size distribution of a water-absorbing resin which particle size distribution is measured by sieve classification. Note that the weight average particle diameter (D50) and the logarithmic standard deviation ($\sigma\zeta$) of a particle size distribution are measured according to a method similar to "(3) Mass-Average Particle Diameter (D50) and Logarithmic Standard Deviation ($\sigma\zeta$) of Particle Diameter Distribution", which is a method disclosed in U.S. Pat. No. 7,638,570.

(e) "Moisture Content" (ERT 430.2-02)

The term "moisture content" refers to a moisture content of a water-absorbing resin. Specifically, a "moisture content" is a value (unit: weight %) calculated from a drying loss from drying 4.0 g of a water-absorbing resin at 105° C. for 3 hours. Note that in some cases, the amount of the water-absorbing resin may be changed to 1.0 g, and the drying temperature changed to 180° C.

(f) "Residual Monomers" (ERT410.2-02)

The term "residual monomers" means the amount of monomers left in a water-absorbing resin. Hereinafter, the amount of monomers left in a water-absorbing resin is referred to as "residual monomers." Specifically, the term "residual monomers" refers to a dissolved residual monomer amount (unit: ppm) in an aqueous solution. The dissolved residual monomer amount is obtained by adding 1.0 g of a water-absorbing resin to 200 ml of a 0.9 weight % aqueous sodium chloride solution and stirring a resultant mixture at 500 rpm for 1 hour. The residual monomer amount is measured by use of high-performance liquid chromatography (HPLC).

(1-4) "Liquid Permeability"

The term "Liquid permeability" as used herein refers to flowability a liquid passing through a space between respective particles of a swollen gel of a water-absorbing resin under load or without load. The "liquid permeability" is measured typically as a Saline Flow Conductivity (SFC) or Gel Bed Permeability (GBP).

The term "SFC" refers to liquid permeability of a 0.69 weight % aqueous sodium chloride solution in a water-absorbing resin under a load of 0.3 psi (2.07 kPa), and is measured according to the SFC test method disclosed in the specification of U.S. Pat. No. 5,669,894.

The term "GBP" refers to liquid permeability of a 0.9 weight % aqueous sodium chloride solution in a water-absorbing resin which is under load (0.3 psi) or is allowed to freely swell, and is measured according to the GBP test method disclosed in International Publication No. WO 2005/016393.

(1-5) "Water Absorption Speed"

The term "water absorption speed" as used herein is an index indicating water absorption performance of a water-absorbing resin and refers to a fluid retention capacity per unit of time (unit: g/g/s). One typical method for measuring water absorption speed is free swelling rate (FSR). A specific method of measurement is described in the Examples.

(1-6) "Gap Fluid Retention Property Under Pressure"

The term "gap fluid retention property under pressure" as used herein refers to a gap fluid per gram of a water-absorbing agent under a load of 0.3 psi (2.07 kPa).

Note that the term "gap fluid" above refers to a liquid retained between gel particles (in gaps between gel particles) of 1 g of a water-absorbing agent under a load of 0.3 psi (2.07 kPa), the gel particles being in a layer after having been swollen in a 0.69 weight % aqueous sodium chloride solution. In other words, when a water-absorbing resin is swollen in a 0.69 weight % aqueous sodium chloride solution, the gap fluid retention property under pressure is a weight of the aqueous sodium chloride solution per gram of said water-absorbing agent, the sodium chloride solution being retained in gaps within the water-absorbing agent under a load of 2.07 kPa (0.3 psi).

Similar measurement methods that have been proposed to date include pressurized void average radius index (Patent Literature 3) and wet porosity (Patent Literature 4).

The pressurized void average radius index, however, is a measurement of a radius of gaps between swollen gel particles. This measured parameter therefore differs from that of the gap fluid retention property under pressure of the present invention, which is a measurement of an amount of fluid in gaps. Further, results of studies done by the inventors have shown that wet porosity does not allow for accurate apprehension of physical properties of water-absorbing resin which affect the performance of a disposable diaper. This is due to the method for measuring wet porosity. During measurement of wet porosity, a water-absorbing resin layer is caused to absorb a liquid to be measured from a lower surface of the layer. With this method, however, updraw absorption properties (such as gel blocking) of the water-absorbing resin layer affect a gel layer that is formed and a measured value.

In contrast, in the method, in accordance with the present invention, for measuring gap fluid retention property under pressure, a water-absorbing resin layer is caused to absorb a large amount of liquid to be measured from an upper surface of the layer. This is similar to actual use of disposable diapers and absorbent body evaluation of disposable diapers. As such, physical properties (such as gel blocking) which are unnecessary for the measurement of a water-absorbing resin layer do not affect a measured value. This makes it possible to measure a physical property which is highly correlated to re-wet, an important indicator of the performance of a disposable diaper.

(1-7) "BET Specific Surface Area"

The term "BET specific surface area" as used herein refers to a specific surface area of a water-absorbing resin as measured by the BET method, which is a method for measuring the specific surface area of a particle. "Specific surface area" refers to a surface area per unit weight of an object (unit: $m^2/g$).

In a case where the object is a particle, a greater specific surface area typically correlates to a finer particle. However, since an increase in complexity of surface structure correlates to a greater value of specific surface area, the value of a specific surface area does not always reflect particle size.

The "BET method" refers to a method in which a solid particle is caused to adsorb molecules of a gas such as nitrogen, argon, krypton, or carbon oxide, and then the specific surface area of the solid particle is measured from an adsorbed amount of the gas molecules. A specific method of measurement is described in the Examples.

(1-8) "Gel-Crushing"

The term "gel-crushing" as used in the present invention means an operation in which a crosslinked hydrogel polymer obtained in a polymerization step is made smaller in size by use of a gel-crushing device so as to have a desired particle diameter and shape. Specifically, "gel-crushing" means a technique in which a crosslinked hydrogel polymer obtained in a polymerization step is subjected to gel-crushing by use of a gel-crushing device so as to have a weight average particle diameter (D50) preferably of 300 μm to 1,700 μm and more preferably of 350 μm to 1,000 μm, and a logarithmic standard deviation (σζ) of a particle size distribution preferably of 0.2 to 1.5 and more preferably of 0.2 to 1.2.

(1-9) "Gel-Grinding Energy"

The term "gel-grinding energy" as used in the present invention means mechanical energy per unit weight (unit weight of a crosslinked hydrogel polymer), which mechanical energy is necessary for a gel-crushing device to gel-crush a crosslinked hydrogel polymer. The gel-grinding energy does not include energy with which to heat or cool a jacket, or energy of water and steam to be introduced.

Note that "gel-grinding energy" is abbreviated as "GGE". In a case where the gel-crushing device is driven by a three-phase alternating current power supply, the GGE is calculated based on the following Equation (1).

[Math. 1]

$$GEE\ (J/g) = (\sqrt{3} \times voltage \times current \times power\ factor \times motor\ efficiency)/(weight\ of\ crosslinked\ hydrogel\ polymer\ to\ be\ introduced\ into\ gel\text{-}crushing\ device\ per\ second) \quad (1)$$

The "power factor" and the "motor efficiency" are each a value which is unique to the gel-crushing device and changes depending on, for example, an operation condition of the gel-crushing device and which ranges from 0 to 1. In a case where the gel-crushing device is driven by a single-phase alternating current power supply, the GGE can be calculated by replacing "3" with "1" in the above Equation (1). Note that a unit of a voltage is [V], a unit of a current is [A], and a unit of weight of a crosslinked hydrogel polymer is [g/s].

Note also that it is also possible to carry out gel-crushing with respect to a crosslinked hydrogel polymer by use of a plurality of gel-crushing devices. In such a case, it is only necessary to calculate GGE for each of the plurality of gel-crushing devices.

Since the mechanical energy to be applied to the crosslinked hydrogel polymer is one of the important factors, the gel-grinding energy is preferably calculated by subtracting a current value of the gel-crushing device during idling from a current value of the gel-crushing device during gel-crushing. In particular, gel-crushing that is carried out by use of a plurality of gel-crushing devices increases a sum of current values of the plurality of gel-crushing devices during idling. Thus, it is suitable to calculate the gel-grinding energy by subtracting the current values of the plurality of gel-crushing devices during idling from current values of the plurality of gel-crushing devices during gel-crushing. In this case, the gel-grinding energy is calculated based on the following Equation (2). Note that gel-grinding energy calculated based on Equation (2) is denoted as GGE2 so as to be distinguished from the GGE calculated based on Equation (1).

[Math. 2]

$$GGE2\ (J/g) = (\sqrt{3} \times voltage \times [current\ during\ gel\text{-}crushing - current\ during\ idling] \times power\ factor \times motor\ efficiency)/(weight\ of\ crosslinked\ hydrogel\ polymer\ to\ be\ introduced\ into\ gel\text{-}crushing\ device\ per\ second) \quad (2)$$

As the "power factor" and the "motor efficiency" in Equation (2), values thereof during gel-crushing are employed. Note that, since a current value during idling is small, the power factor and the motor efficiency during idling are approximately defined as in Equation (2). For example, in a case where an amount of the crosslinked hydrogel polymer to be continuously fed by a quantitative feeder is [t/hr], the "weight of crosslinked hydrogel polymer to be introduced into gel-crushing device per second [g/s]" in each of Equations (1) and (2) refers to a value obtained by converting [t/hr] into [g/s].

(1-10) Other

In the present specification, a range "X to Y" means "not less than X and not more than Y". Furthermore, unless otherwise specified, the unit of weight "t (ton)" means "metric ton," and "ppm" means "ppm by weight" or "ppm by mass."

Further, " . . . acid (salt)"means" . . . acid and/or salt thereof", and "(meth)acrylic" means "acrylic and/or methacrylic."

[2] Method for Producing Water-Absorbing Agent

A first method for producing a water-absorbing agent in accordance with the present invention is a method for producing a water-absorbing agent containing a polyacrylic acid (salt)-based water-absorbing resin as a main component, including the steps of: (1) preparing an aqueous monomer solution containing acrylic acid (salt) as a main monomer component, the step (1) including at least one of the following steps: (a) introducing, into the aqueous monomer solution, a gas in an amount of not less than 0.0015 ml of the gas per gram of the aqueous monomer solution; (b) causing gas bubbles to be created and contained in the aqueous monomer solution by decreasing a solubility of dissolved gas in the aqueous monomer solution; and (c) adding, to the aqueous monomer solution, a foaming agent in an amount of not more than 5 weight % relative to solid content of a below-mentioned water-absorbing resin powder; (2) subjecting the aqueous monomer solution obtained in the step (1) to foaming polymerization in the presence of a foaming agent and/or gas bubbles so that a crosslinked hydrogel polymer is obtained; (3) grain-refining the crosslinked hydrogel polymer during or after the foaming polymerization by use of a motive power having a gel-grinding energy 2 (GGE2) of 7 J/g to 40 J/g; (4) drying the crosslinked hydrogel polymer after the foaming polymerization so that a dried polymer is obtained; (5) pulverizing and classifying the dried polymer after drying so that a water-absorbing resin powder is obtained; and (6) surface-crosslinking the water-absorbing resin powder.

A second method for producing the above water-absorbing agent is a method for producing a water-absorbing agent containing a polyacrylic acid (salt)-based water-absorbing resin as a main component, including the steps of: (1) preparing an aqueous monomer solution containing acrylic acid (salt) as a main monomer component, the step (1) including at least one of the following steps: (a) introducing, into the aqueous monomer solution, a gas in an amount of not less than 0.0015 ml of the gas per gram of the aqueous monomer solution; (b) causing gas bubbles to be created and contained in the aqueous monomer solution by decreasing a solubility of dissolved gas in the aqueous monomer solution; and (c) adding, to the aqueous monomer solution, a foaming agent in an amount of not more than 5 weight % relative to solid content of a below-mentioned water-absorbing resin powder; (2) subjecting the aqueous monomer solution obtained in the step (1) to foaming polymerization in the presence of a foaming agent and/or gas bubbles so that a crosslinked hydrogel polymer is obtained; (3') grain-refining the crosslinked hydrogel polymer during or after the step (2) by use of a motive power having a gel-grinding energy 2 (GGE2) of not less than 7 J/g and less than 18 J/g; (4) drying a grain-refined crosslinked hydrogel polymer obtained in the step (3') so that a dried polymer is obtained; (5) pulverizing and classifying the dried polymer obtained in the step (4) so that a water-absorbing resin powder is obtained; (6) surface-crosslinking the water-absorbing resin powder, obtained through the steps (1) through (5) and having a BET specific surface area of not less than 0.0270 m$^2$/g and less than 0.0310 m$^2$/g, so that water-absorbing resin particles are obtained; and (7) adding, to the water-absorbing resin particles obtained in the step (6), a liquid permeability improving agent in the amounts of (I) through (III) below: (I) in a case where the liquid permeability improving agent is a polyvalent metal cation, an amount such that an amount of polyvalent metal atoms is less than $1.40 \times 10^{-5}$ mol/g; (II) less than 2.0 weight %, in a case where the liquid permeability improving agent is a cationic polymer; and (III) (IIIa) less than 0.3 weight %, in a case where the liquid permeability improving agent is inorganic fine particles having a primary particle diameter of less than 20 nm, and (IIIb) less than 1.0 weight %, in a case where the liquid permeability improving agent is inorganic fine particles having a primary particle diameter of not less than 20 nm, each of the amounts of (I) through (III) being a proportion relative to the solid content of the water-absorbing resin powder.

A third method for producing the above water-absorbing agent is a method for producing a water-absorbing agent containing a polyacrylic acid (salt)-based water-absorbing resin as a main component, including the steps of: (1) preparing an aqueous monomer solution containing acrylic acid (salt) as a main monomer component, the step (1) including at least one of the following steps: (a) introducing, into the aqueous monomer solution, a gas in an amount of 0.0015 ml of the gas per gram of the aqueous monomer solution; (b) causing gas bubbles to be created and contained in the aqueous monomer solution by decreasing a solubility of dissolved gas in the aqueous monomer solution; and (c) adding, to the aqueous monomer solution, a foaming agent in an amount of not more than 5 weight % relative to solid content of a below-mentioned water-absorbing resin powder; (2) subjecting the aqueous monomer solution obtained in the step (1) to foaming polymerization in the presence of a foaming agent and/or gas bubbles so that a crosslinked hydrogel polymer is obtained; (3") grain-refining the crosslinked hydrogel polymer during or after the step (2) by use of a motive power having a gel-grinding energy 2 (GGE2) of not less than 18 J/g and not more than 40 J/g; (4) drying a grain-refined crosslinked hydrogel polymer obtained in the step (3") so that a dried polymer is obtained; (5) pulverizing and classifying the dried polymer obtained in the step (4) so that a water-absorbing resin powder is obtained; (6) surface-crosslinking the water-absorbing resin powder, obtained through the steps (1) through (5) and having a BET specific surface area of not less than 0.0310 m$^2$/g, so that water-absorbing resin particles are obtained; and (7) adding, to the water-absorbing resin particles obtained in the step (6), a liquid permeability improving agent in the amounts of (i) through (iii) below: (i) in a case where the liquid permeability improving agent is a polyvalent metal cation, an amount such that an amount of polyvalent metal atoms is less than $3.60 \times 10^{-5}$ mol/g; (ii) less than 2.5 weight %, in a case where the liquid permeability improving agent is a cationic polymer; and (iii) (iiia) less than 1.2 weight %, in a case where the liquid permeability improving agent is inorganic fine particles having a primary particle diameter of less than 20 nm, and (iiib) less than 2.0 weight %, in a case where the liquid permeability improving agent is inorganic fine particles having a primary particle diameter of not less than 20 nm, each of the amounts of (i) through (iii) being a proportion relative to the solid content of the water-absorbing resin powder.

The following description will discuss a method for producing a water-absorbing agent in accordance with the present invention.

(2-1) Step of Preparing Aqueous Monomer Solution
(Step 1)

Step 1 is a step of preparing an aqueous solution containing, as a main component, acrylic acid (salt) (this aqueous solution hereinafter referred to as an "aqueous monomer solution"). Note that the term "main component" means that the acrylic acid (salt) is used (contained) preferably in an amount of not less than 50 mol %, more preferably of not less than 70 mol %, and even more preferably of not less than 90 mol % (an upper limit being 100 mol %) relative to an amount of monomers to be used for a polymerization reaction of a water-absorbing resin (excluding an internal crosslinking agent). It is also possible to use a monomer slurry liquid to the extent that a water-absorbing resin to be produced will not have degraded water absorption performance. For convenience of description, however, this section describes an aqueous monomer solution.

(Acrylic Acid (Salt))

In the present invention, an acrylic acid and/or a salt thereof (hereinafter referred to as "acrylic acid (salt)") is used as a monomer from the viewpoint of physical properties of a water-absorbing resin to be obtained and from the viewpoint of productivity. The acrylic acid may be a publicly known acrylic acid containing a trace component(s) such as a polymerization inhibitor and/or an impurity.

The polymerization inhibitor is not limited to any particular one, but is preferably a phenol, more preferably a methoxyphenol, and even more preferably a p-methoxyphenol. A concentration of the polymerization inhibitor in the acrylic acid is preferably not more than 200 ppm, more preferably 10 ppm to 160 ppm, and even more preferably 20 ppm to 100 ppm, from the viewpoint of, for example, polymerizability of the acrylic acid and the color of a water-absorbing resin to be produced.

The impurity in the acrylic acid for the present invention may be, for example, a compound disclosed in U.S. Patent Application No. 2008/0161512.

The acrylic acid salt is one obtained by neutralizing the abovementioned acrylic acid by use of the below-mentioned basic composition. The acrylic acid salt may be a commercially available acrylic acid salt (for example, sodium acrylate) or may be an acrylic acid salt obtained by carrying out a neutralization process on an acrylic acid in a plant where a water-absorbing resin is produced.

(Basic Composition)

In the present invention, "basic composition" refers to a composition containing a basic compound, such as a commercially available aqueous sodium hydroxide solution.

Specific examples of the basic compound encompass a carbonate of alkali metal, a bicarbonate of alkali metal, a hydroxide of alkali metal, ammonia, and organic amine. Among these, the basic compound preferably has strong basicity from the viewpoint of physical properties of a water-absorbing resin to be obtained. That is, the basic compound is more preferably a hydroxide of alkali metal, such as sodium hydroxide, potassium hydroxide, or lithium hydroxide, and is even more preferably sodium hydroxide.

(Neutralization)

In the present invention, an acrylic acid can be neutralized with the use of a basic composition so that an acrylic acid salt can be obtained. Note that the neutralization can be neutralization of an acrylic acid (neutralization before polymerization), neutralization of a crosslinked hydrogel polymer to be obtained by crosslinking and polymerizing an acrylic acid (neutralization after polymerization) (hereinafter referred to as "later neutralization"), or a combination of the neutralization of an acrylic acid and the neutralization of a crosslinked hydrogel polymer to be obtained by crosslinking and polymerizing an acrylic acid.

The neutralization can be of a continuous type or a batch type. From the viewpoint of production efficiency, however, the neutralization is preferably of the continuous type. Note that with regard to conditions such as a neutralization apparatus, a neutralization temperature, and a retention time, the conditions disclosed in International Publication No. 2009/123197 and U.S. Patent Application Publication No. 2008/0194863 can be applied to the present invention.

A neutralization rate in the present invention is preferably 10 mol % to 90 mol %, more preferably 40 mol % to 85 mol %, even more preferably 50 mol % to 80 mol %, and particularly preferably 60 mol % to 75 mol % per an acid group of a monomer.

A neutralization rate of not less than 10 mol % is preferable because, with such a neutralization rate, a fluid retention capacity will not be lowered significantly. A neutralization rate of not more than 90 mol % is preferable because, with such a neutralization rate, it is easy to obtain a water-absorbing resin having a high fluid retention capacity under pressure.

The neutralization rate can also apply to the later neutralization. The neutralization rate can also apply to a neutralization rate for a water-absorbing resin which is an end product.

(Other Monomer(s))

In the present invention, a water-absorbing resin can be produced by using, as "other monomer(s)", a compound disclosed in U.S. Patent Application Publication No. 2005/0215734 (except for an acrylic acid) in combination with the acrylic acid (salt). Note that examples of a water-absorbing resin to be obtained by the production method in accordance with the present invention encompass a water-absorbing resin in which a hydrophilic or hydrophobic unsaturated monomer is a copolymerization component.

(Internal Crosslinking Agent)

The compounds disclosed in U.S. Pat. No. 6,241,928 can be used as an internal crosslinking agent usable in the present invention. One of the compounds or two or more of the compounds is/are to be selected in view of reactivity.

From the viewpoint of water absorption performance and the like of a water-absorbing resin to be obtained, it is preferable to use, as an internal crosslinking agent, a compound having two or more polymerizable unsaturated groups, more preferable to use a compound which is pyrolytic at a drying temperature of a later described drying step, and even more preferable to use a compound having a (poly)alkylene glycol structural unit and two or more polymerizable unsaturated groups.

Preferable examples of the polymerizable unsaturated group encompass an allyl group and a (meth)acrylate group. More preferable examples of the polymerizable unsaturated group encompass a (meth)acrylate group. The polyalkylene glycol structural unit is preferably polyethylene glycol. An n number of 1 to 100 is preferable, and an n number of 6 to 50 is more preferable.

As such, in the present invention, the internal crosslinking agent is preferably (poly)alkylene glycol di(meth)acrylate or (poly)alkylene glycol tri(meth)acrylate, and more preferably (poly)ethylene glycol di(meth)acrylate.

An amount of the internal crosslinking agent used is preferably 0.0001 mol % to 10 mol %, and more preferably 0.001 mol % to 1 mol % relative to a total amount of monomers. In a case where the amount used falls within the above ranges, a desired water-absorbing resin can be obtained. Note that in a case where the amount used is excessively small, gel strength tends to be lowered and consequently there tends to be an increase in water-soluble component. In a case where the used amount is excessively large, fluid retention capacity tends to be lowered. Therefore, the amount used that is excessively large is not preferable.

In the present invention, the following method is preferably used: An aqueous monomer solution, to which a certain amount of internal crosslinking agent has been added in advance, is prepared. Then, the aqueous monomer solution is simultaneously subjected to polymerization and to a crosslinking reaction. Alternatively, other than the above method, examples of a possible method encompass a method in which an internal crosslinking agent is added during or after polymerization, so that postcrosslinking is carried out, a method in which radical crosslinking is carried out with the use of a radical polymerization initiator, and a method in which radiation crosslinking is carried out with the use of active energy rays such as an electron ray or an ultraviolet ray. Alternatively, these methods can be used in combination.

(Gas Bubble)

In the present invention, the aqueous monomer solution is subjected to foaming polymerization in the presence of gas bubbles. The gas bubbles can be dispersed by the following methods. Method for dispersing gas bubbles include, for example, a method of decreasing the solubility of dissolved gas, a method of introducing a gas from an external source, and a method of adding a foaming agent to an aqueous monomer solution. A plurality of these methods may be used in conjunction with each other in accordance with a desired physical property of the water-absorbing resin. Examples of a gas constituting the gas bubbles to be dispersed in the aqueous monomer solution include oxygen, air, nitrogen, carbonic acid gas, ozone, and a compound of any of these. An inert gas such as nitrogen or carbonic acid gas is preferably used. From the viewpoint of polymerizability and cost, the gas is more preferably air or nitrogen. The pressure of the gas during and after introduction is decided as necessary and can be atmospheric pressure, an increased pressure, or a reduced pressure.

(Method of Decreasing Solubility of Dissolved Gas)

In the present invention, gas bubbles can be stably dispersed by using an aqueous monomer solution to which a surfactant and/or dispersant has been added and decreasing the solubility of dissolved gas in the aqueous monomer solution. A method of decreasing the solubility of the dissolved gas can be decided as necessary in accordance with, for example, desired physical properties and production cost.

Examples of specific methods for decreasing the solubility of the dissolved gas include a method of increasing the temperature of the aqueous monomer solution and a method of adding water-soluble organic matter. The method of increasing the temperature of the aqueous solution is most preferable. An amount of dissolved gas in the aqueous monomer solution can be controlled in advance in order to control an amount of introduced gas bubbles.

Further, by adjusting the type(s) and/or amount(s) of the surfactant and/or the dispersant as appropriate, it is possible to obtain water-absorbing resin powder having intended physical properties. The surfactant is preferably a non-polymeric surfactant, while the dispersant is preferably a polymeric dispersant. Further, it is preferable that the surfactant and/or the dispersant be added before the aqueous monomer solution prior to or during polymerization reaches a temperature of not lower than 50° C.

The type(s) of the surfactant and/or dispersant can be decided as appropriate in accordance with a desired physical property. As specific surfactants, surfactants shown as examples in International Publication No. 2011/078298 are suitably used. Among them, a nonionic surfactant is preferable, a nonionic surfactant having a polyoxyethylene chain in a molecule is more preferable, and polyoxyethylene sorbitan fatty acid ester is most preferable.

The amount of any of these surfactants to be used depends on the type of the surfactant to be used or intended physical properties (in particular, water absorption speed and/or surface tension). However, the amount used is typically within a range of more than 0 weight % and not more than 2 weight %, preferably more than 0 weight % and not more than 0.03 weight %, more preferably more than 0 weight % and not more than 0.015 weight %, even more preferably more than 0 weight % and not more than 0.01 weight %, and most preferably more than 0 weight % and not more than 0.008 weight %, relative to the amount of a monomer(s) to be used. The amount of the surfactant to be used is applicable to a base water-absorbing resin after polymerization, and is further applicable, if necessary, to water-absorbing resin powder as an end product obtained after coating with a surfactant described above in "(2-6) Surface-crosslinking step".

(Method for Introducing Gas from External Source)

In the present invention, gas bubbles can be introduced into the aqueous monomer solution by introducing a gas from an external source. Gases that can be used are as described above. The gas introduced from the external source need only be mixed with the aqueous monomer solution. A publicly known method, such as a static mixer method, a cavitation method, or a venturi method can be used. These methods can be used in combination.

An introduced amount of gas per gram of aqueous monomer solution is normally not less than 0.0015 ml/g, preferably not less than 0.0035 ml/g, and more preferably not less than 0.005 ml/g. An introduced amount of gas that is too low is not preferable as it may result in failure to obtain a desired physical property of the water-absorbing resin. Note that the abovementioned introduced amounts of gas are values at 20° C. and 1 atm.

(Method for Adding Foaming Agent to Aqueous Monomer Solution)

In the present invention, foaming polymerization can be carried out by adding a foaming agent to the aqueous monomer solution. The foaming agent can be, for example, a carbonate or an azo compound which creates gas when heated. An added amount of the foaming agent is preferably not more than 5 weight %, more preferably not more than 1 weight %, and even more preferably not more than 0.5 weight % (with the lower limit of 0 weight %), relative to solid content of water-absorbing resin powder.

(Other Materials Added to Aqueous Monomer Solution)

An embodiment of the present invention may include adding any material below to the aqueous monomer solution during the preparation thereof from the viewpoint of improved physical properties for a water-absorbing resin to be produced.

Specifically, a hydrophilic polymer such as starch, a starch derivative, cellulose, a cellulose derivative, polyvinyl alcohol, polyacrylic acid (salt), and/or crosslinked polyacrylic acid (salt) can be added to the aqueous monomer solution in an amount of preferably not more than 50 weight %, more preferably not more than 20 weight %, even more preferably not more than 10 weight %, and especially even more preferably not more than 5 weight % (with the lower limit of 0 weight %). A chelating agent, a chain transfer agent, and/or the like can be added to the aqueous monomer solution in an amount of preferably not more than 5 weight %, more preferably not more than 1 weight %, and even more preferably not more than 0.5 weight % (with the lower limit of 0 weight %).

The above materials can be added to the aqueous monomer solution or can be added during polymerization. Alternatively, the above materials can be added both to the aqueous monomer solution and during polymerization.

In a case where the water-soluble resin or a water-absorbing resin is used as the hydrophilic polymer, a graft polymer or a water-absorbing resin composition (e.g. a polymer produced from starch and an acrylic acid, a polymer produced from PVA and an acrylic acid, and the like) can be obtained. These polymers and water-absorbing resin compositions are also encompassed in the scope of the present invention.

(Monomer Component Concentration)

In the present invention, the above various materials are added during preparation of the aqueous monomer solution. A monomer component concentration in the aqueous monomer solution (this concentration hereinafter also referred to as "monomer concentration") is not particularly limited, but is preferably 10 weight % to 80 weight %, more preferably 20 weight % to 75 weight %, and even more preferably 30 weight % to 70 weight %, from the viewpoint of physical properties of a water-absorbing resin and from the viewpoint of productivity.

In a case where the form of polymerization employed is aqueous solution polymerization or reversed phase suspension polymerization, solvents other than water can be used in combination as necessary. In such a case, a type of the solvent used is not limited to any particular one.

Note that the "monomer component concentration" is a value that can be obtained by the following Equation (3). A weight of an aqueous monomer solution does not include a weight of a graft component, a weight of water-absorbing resin, or a weight of a hydrophobic solvent used in reversed phase suspension polymerization.

[Math. 3]

Monomer component concentration (weight %)= (weight of monomer component)/(weight of aqueous monomer solution)×100     (3)

(2-2) Polymerization Step (Step (2))

This step is a step of polymerizing an acrylic acid (salt)-based aqueous monomer solution obtained in the step of preparing the aqueous monomer solution, so that a crosslinked hydrogel polymer (hereinafter referred to as "hydrogel") is obtained. In other words, this step (step (2)) is a step of subjecting the aqueous monomer solution obtained in the step (1) to foaming polymerization in the presence of a foaming agent and/or gas bubbles so that a crosslinked hydrogel polymer is obtained.

(Polymerization Initiator)

The polymerization initiator for use in the present invention is selected as appropriate in accordance with a form of polymerization or the like and is not limited to any particular one. Examples of the polymerization initiator include a pyrolytic radical polymerization initiator, a photolytic radical polymerization initiator, and a redox-type polymerization initiator that contains a reducing agent for facilitating decomposition of any of those polymerization initiators. Specifically, used as the polymerization initiator is one of the polymerization initiators disclosed in U.S. Pat. No. 7,265,190, or a compound of two or more of the polymerization initiators disclosed in U.S. Pat. No. 7,265,190. Further, the polymerization initiator is preferably a peroxide or an azo compound, more preferably a peroxide, and even more preferably a persulfate, from the viewpoint of, for example, the handleability of the polymerization initiator and the physical properties of the water-absorbing resin.

The amount of the polymerization initiator to be used ranges from preferably 0.001 mol % to 1 mol %, and more preferably 0.001 mol % to 0.5 mol %, relative to the amount of monomers. The amount of the reducing agent to be used ranges from preferably 0.0001 mol % to 0.02 mol %, relative to the amount of monomers. Using the polymerization initiator and the reducing agent in amounts falling within the above ranges makes it possible to obtain a desired water-absorbing resin.

A polymerization reaction can be carried out by, instead of using the polymerization initiator, irradiating a monomer with an active energy ray such as a radial ray, an electron ray, or an ultraviolet ray. Alternatively, any of these active energy rays can be used in combination with a polymerization initiator.

(Form of Polymerization)

Polymerization to be applied to the present invention is not limited to any particular form. From the viewpoint of a water absorbent property, ease of control of polymerization, and the like, preferable examples of the polymerization encompass vapor phase spray polymerization, vapor phase droplet polymerization, aqueous solution polymerization, and reversed phase suspension polymerization, more preferable examples of the polymerization encompass aqueous solution polymerization and reverse phase suspension polymerization, and even more preferable examples of the polymerization encompass aqueous solution polymerization. Among these, continuous aqueous solution polymerization is particularly preferable. The continuous aqueous solution polymerization can be any one of continuous belt polymerization and continuous kneader polymerization.

Specific examples of the form of continuous belt polymerization encompass those disclosed in U.S. Pat. Nos. 4,893,999, 6,241,928, and U.S. Patent Application Publication No. 2005/0215734. Specific examples of the form of continuous kneader polymerization encompass those disclosed in U.S. Pat. Nos. 6,987,151 and 6,710,141. In a case where these forms of continuous aqueous solution polymerization are employed, it is possible to improve efficiency with which a water-absorbing resin is produced.

Preferable examples of the form of the continuous aqueous solution polymerization encompass "high-temperature-initiating polymerization" and "high-concentration polymerization". The "high-temperature-initiating polymerization" is a form of polymerization in which polymerization is started while a temperature of an aqueous monomer solution is preferably not less than 30° C., more preferably not less than 35° C., even more preferably not less than 40° C., and especially even more preferably not less than 50° C. (upper limit: boiling point). The "high-concentration polymerization" is a form of polymerization in which polymerization is carried out while a monomer concentration in an aqueous monomer solution is preferably not less than 30 weight %, more preferably not less than 35 weight %, even more preferably not less than 40 weight %, and especially even more preferably not less than weight % (upper limit: saturating concentration). Alternatively, it is possible to use these forms of polymerization in combination.

In the present invention, polymerization can be carried out in an air atmosphere. From the viewpoint of color of a water-absorbing resin to be obtained, polymerization is to be carried out preferably in an atmosphere of inert gas such as nitrogen or argon. In such a case, an oxygen concentration is preferably controlled to be, for example, not more than 1 volume %. Note that dissolved oxygen in an aqueous monomer solution is also preferably substituted with inert gas (e.g. dissolved oxygen: less than 1 mg/l).

In the present invention, alternatively, it is possible to increase a solid content concentration during polymerization. A degree of increase in solid content as an index of an increase in such a solid content concentration can be defined by the following Equation (4). Note that the degree of increase in solid content concentration is preferably not less than 1 weight % and more preferably not less than 2 weight %.

[Math. 4]

$$\text{Degree (weight \%) of increase in solid content} = \text{(solid content concentration in hydrogel after polymerization)} - \text{(solid content concentration in aqueous monomer solution)} \quad (4)$$

Where the solid content concentration in an aqueous monomer solution is a value that can be obtained by the following Equation (5) and where components in a polymerization system are an aqueous monomer solution, a graft component, a water-absorbing resin and other solid matters (e.g., inorganic fine particles and the like), and therefore exclude a hydrophobic solvent in reversed phase suspension polymerization.

[Math. 5]

$$\text{Solid content concentration (weight \%) in aqueous monomer solution} = \text{(weight of [monomer component+graft component+water-absorbing resin+other solid matters])}/\text{(weight of components in polymerization system)} \times 100 \quad (5)$$

(2-3) Gel-Crushing Step (Step (3))

This step is a step of gel-crushing a hydrogel, which has been obtained by the polymerization step, with use of, for example, a kneader, a screw extruder such as a meat chopper, or a gel-crusher such as a cutter mill in order to obtain a hydrogel in the form of particles (hereinafter referred to as "particulate hydrogel"). In other words, this step (step 3) is a step of grain-refining a crosslinked hydrogel polymer during or after the foaming polymerization by use of a motive power having a gel-grinding energy 2 (GGE2) of 7 J/g to 40 J/g. That is, this step is a step of grain-refining a crosslinked hydrogel polymer during or after the step (2) by use of a motive power having a gel-grinding energy 2 (GGE2) within a specific range.

In a case where the polymerization step is carried out through kneader polymerization, such a step is equivalent to a combination of the polymerization step and the gel-crushing step which are carried out simultaneously. In a case where a particulate hydrogel is directly obtained through a polymerization process, such as a case where the polymerization step employs reversed phase suspension polymerization, the gel-crushing step may be skipped.

The gel-crushing step not only increases drying efficiency by decreasing the size of a hydrogel and increasing the surface area of the hydrogel, but also makes it possible to obtain a hydrogel having a desired shape through gel-crushing at a specific gel-grinding energy.

(Gel-Grinding Energy)

In the present invention, gel-grinding energy is preferably controlled to be within a certain range. In particular, with regards to gel-grinding energy 2 (GGE2), an upper limit value thereof is preferably not more than 40 J/g, more preferably not more than 32 J/g, and even more preferably not more than 25 J/g. A lower limit value of GGE2 is preferably not less than 7 J/g, more preferably not less than 8 J/g, and even more preferably not less than 9 J/g.

As such, a typical range of the gel-grinding energy 2 (GGE2) can be selected as appropriate within a range between the above upper limit values and lower limit value. However, the range is preferably 7 J/g to 40 J/g, more preferably 7 J/g to 32 J/g, and even more preferably 8 J/g to 25 J/g. A range such as 9 J/g to 40 J/g, for example, can also be selected.

Controlling the GGE2 to be within a range as above makes it possible to apply an appropriate shearing force and compressive force to the hydrogel during gel-crushing.

Note that in a second production method, the GGE2 is in a range of not less than 7 J/g to less than 18 J/g (corresponding to the step 3'). In a third production method, the GGE2 is in a range of not less than 18 J/g to not more than 40 J/g (corresponding to the step 3"). Controlling the GGE2 to be in such ranges makes it possible to control the BET specific surface area of a water-absorbing resin powder to be obtained.

(Particle Size of Hydrogel after Gel-Crushing)

A hydrogel obtained through the polymerization step is in the form of a particulate after being crushed in the gel-crushing step. Note that a particle diameter of a particulate hydrogel can be controlled by classification, blending and/or the like, but in the present invention, the particle diameter is preferably controlled by foaming polymerization and/or by the gel-crushing step.

In the present invention, a weight average particle diameter (D50) (specified by sieve classification) of the particulate hydrogel after gel-crushing is preferably 300 µm to 1,700 µm and more preferably 350 µm to 1,000 µm.

The weight average particle diameter (D50) of not more than 1,700 µm is preferable in that it prevents the particulate hydrogel from being subjected to, for example, uneven or insufficient shearing force and uneven or insufficient compressive force. Furthermore, drying of the particulate hydrogel progresses from a surface layer part toward an internal part. As such, in a case where the weight average particle diameter (D50) is too large, the particulate hydrogel will be crushed in a state where the surface layer part and the internal part have been dried to differing degrees, thereby causing the creation of particles having non-uniform physical properties. This is undesirable as it results in a deterioration in the physical properties of the obtained water-absorbing agent as a whole.

In a case where the weight average particle diameter (D50) is not less than 300 µm, a surface area of the particulate hydrogel becomes smaller, and the particulate hydrogel becomes less likely to dry. This results in residual monomers being reduced, since monomers become less likely to remain in the hydrogel. Furthermore, such a weight average particle diameter (D50) is preferable because a large amount of fine powder is not produced in crushing after drying, which makes it easy to control particle size and prevents a deterioration in physical properties such as liquid permeability (SFC).

In the present invention, a logarithmic standard deviation ($\sigma\zeta$) of a particle size distribution of the particulate hydrogel after gel-crushing is preferably 0.2 to 1.5 and more preferably 0.2 to 1.2.

The logarithmic standard deviation ($\sigma\zeta$) of the particle size distribution preferably has as small a value as possible, because a smaller value correlates to a sharper particle size distribution, which allows for even drying. However, setting the $\sigma\zeta$ to be less than 0.2 would require a special operation such as classification of the hydrogel after crushing or controlling particle size during polymerization prior to gel-crushing.

Therefore, from the viewpoint of productivity and cost, it is preferable for the particulate hydrogel to substantially have a logarithmic standard deviation (σζ) of a particle size distribution of not less than 0.2. Examples of methods for controlling the particle size include the foaming polymerization and the gel-crushing of the present invention.

(2-4) Drying Step (Step (4))

This step is a step of drying the particulate hydrogel, which has been obtained by the polymerization step and/or the gel-crushing step, until a predetermined solid content is attained, so as to obtain a dried polymer. In other words, this step (step (4)) is a step of drying the crosslinked hydrogel polymer after the foaming polymerization so that a dried polymer is obtained. That is, this step is a step of drying a grain-refined crosslinked hydrogel polymer which has been obtained in the step (3), the step (3'), or the step (3"), so that a dried polymer is obtained.

A value of solid content after drying is calculated from drying loss (a change in weight after heating 1 g of the water-absorbing resin at 180° C. for three hours). The solid content is preferably not less than 80 weight %, more preferably in a range of 85 weight % to 99 weight %, even more preferably in a range of 90 weight % to 98 weight %, and especially even more preferably in a range of 92 weight %/o to 97 weight %.

A drying method employed in the present invention is not particularly limited. Example methods include thermal drying, hot air drying, drying under reduced pressure, fluidized bed drying, infrared drying, microwave drying, drum dryer drying, drying by azeotropic dehydration with a hydrophobic organic solvent, and high humidity drying by use of high temperature water vapor. The drying method is, among others, preferably hot air drying, more preferably band drying, in which hot air drying is performed on a through-flow belt, from the viewpoint of drying efficiency.

In the present invention, a drying temperature (in the case of hot air drying, specified as a temperature of hot air) is preferably 100° C. to 300° C., more preferably 120° C. to 250° C., and even more preferably 150° C. to 200° C., from the viewpoint of a color of the water-absorbing resin to be obtained and from the viewpoint of drying efficiency. A drying time is decided as necessary in accordance with desired physical properties of the water-absorbing resin. However, the drying time ranges from preferably 1 minute to 10 hours, more preferably 5 minutes to 3 hours, and even more preferably 10 minutes to 1 hour. In the case of hot air drying, air velocity of the hot air is preferably not more than 3.0 m/s, and more preferably 0.5 m/s to 2.0 m/s. Note that other drying conditions can be set as appropriate in accordance with, for example, moisture content of the particulate hydrogel to be dried, total weight of the particulate hydrogel to be dried, and a desired solid content.

Controlling the above various drying conditions to be within the above ranges makes it less likely for the dried polymer to have variations in its physical properties and makes it possible to control the solid content to be within a predetermined range. Controlling the above various drying conditions to be within the above ranges further makes it possible to prevent coloration of the water-absorbing resin to be obtained and a deterioration in the water absorption performance of the water-absorbing resin to be obtained. In the case of band drying, the various conditions disclosed in, for example, International Publication No. 2006/100300, International Publication No. 2011/025012, International Publication No. 2011/025013, and International Publication No. 2011/111657 can be applied as necessary.

(2-5) Pulverization Step and Classification Step (Step (5))

This step is a step of pulverizing (pulverization step) the dried polymer obtained in the drying step and adjusting (classification step) the particle size of a resulting pulverized polymer to be a particle size within a range so that a water-absorbing resin powder is obtained (for convenience, water-absorbing resin in a powder form before being subjected to surface crosslinking is herein referred to as "water-absorbing resin powder"). In other words, this step (step (5)) is a step of pulverizing and classifying the dried polymer after drying so that a water-absorbing resin powder is obtained. That is, this step is a step of pulverizing and classifying the dried polymer obtained in the step (4) so that a water-absorbing resin powder is obtained. This step can also be a step of pulverizing and classifying the dried polymer after drying so that a water-absorbing resin powder is obtained, the water-absorbing resin powder having a BET specific surface area of not less than 0.027 m$^2$/g, a proportion of particles of the water-absorbing resin powder which have a particle diameter of not less than 150 μm and less than 710 μm being not less than 90 weight %.

An apparatus used in the pulverization step of the present invention is not limited to a particular one and can be, for example, a high-speed crusher such as a roll mill, a hammer mill, a screw mill, and a pin mill; a vibrating mill; a knuckle-type crusher; a cylindrical mixer; and the like. These apparatuses can be used in combination according to need.

A particle size adjusting method in the classification step of the present invention is not limited to a particular one and can be, for example, sieve classification with use of a JIS standard sieve (JIS Z8801-1 (2000)), airflow classification, or the like. The JIS standard sieve has a mesh size ranging preferably from 150 μm to 710 μm. Using a JIS standard sieve having a mesh size in the above range makes it possible to adjust the particle diameter of a water-absorbing resin powder so as to be in a range of not less than 150 μm to less than 710 μm. Note that the particle size of water-absorbing resin is not limited to being adjusted during the pulverization step and classification step, but may alternatively be adjusted as appropriate during the polymerization step (in particular, in reversed phase suspension polymerization, spray polymerization, or droplet polymerization) or other steps (for example, a granulation step or a fine powder recycling step).

Physical Properties of Water-Absorbing Resin Powder (Solid Content)

The water-absorbing resin powder obtained in this step has a solid content which is preferably not less than 90 weight %, more preferably not less than 93 weight %, and even more preferably not less than 95 weight/o %. With regards to an upper limit, the solid content is preferably not more than 98 weight % and more preferably not more than 97 weight %, from the viewpoint of pulverization efficiency.

(BET Specific Surface Area)

The water-absorbing resin powder obtained in this step has a BET specific surface area which is preferably not less than 0.027 m$^2$/g, more preferably not less than 0.029 m$^2$/g, and even more preferably not less than 0.031 m$^2$/g.

In a case where the BET specific surface area is not less than 0.027 m$^2$/g, a gap fluid retention property under pressure of the water-absorbing agent of the present invention takes on a more favorable value. This reduces re-wet under pressure in a disposable diaper and therefore enables more favorable performance for an absorbent body of an absorbent article. Note that the BET specific surface area can be controlled by the foaming polymerization, the gel-crushing, and the particle size adjustment of the present invention.

(Particle Size)

The water-absorbing resin powder obtained in this step has a weight average particle diameter (D50) which ranges preferably from 200 µm to 600 µm, more preferably 200 µm to 550 µm, even more preferably 250 µm to 500 µm, and especially even more preferably 300 µm to 450 µm. A proportion of particles having a particle diameter of not less than 150 µm and less than 710 µm is preferably not less than 90 weight %, more preferably not less than 95 weight/n %, even more preferably not less than 97 weight %, and especially even more preferably not less than 98 weight %. Note that an upper limit value of the proportion of particles having the above particle diameter is 100 weight %. Particles having a particle diameter of less than 150 µm are contained at a proportion which is preferably not more than 10 weight %, more preferably not more than 5 weight %, and even more preferably not more than 1 weight %. Particles having a particle diameter of not less than 710 µm are contained at a proportion which is preferably not more than 5 weight %, more preferably not more than 3 weight %, and even more preferably not more than 1 weight %. A lower limit value of each of the proportions of such particles is preferably as low as possible and is desirably 0 weight %. Note, however, that a lower limit of each of the proportions of such particles can be approximately 0.1 weight %. Further, a logarithmic standard deviation (σζ) of the particle size distribution is preferably 0.20 to 0.50, more preferably 0.25 to 0.45, and even more preferably 0.30 to 0.40. Note that each of these particle sizes is measured with use of a standard sieve in conformity to a measurement method disclosed in U.S. Pat. No. 7,638,570 or ERT420.2-02.

The above particle sizes apply not only to water-absorbing resin after surface crosslinking, but also to the water-absorbing resin as a final product. Therefore, it is preferable to carry out surface crosslinking so that the particle size falling within the above described range is maintained, and it is more preferable to carry out particle size adjustment by carrying out a sizing step subsequent to the surface-crosslinking step. Note that, for convenience, the water-absorbing resin subsequent to the surface crosslinking is referred to as "water-absorbing resin particle(s)." Furthermore, the water-absorbing resin particles may also be referred to as a "water-absorbing agent" when being referred to as a final product.

In the present invention, it is important to control particle size distribution in order to improve the gap fluid retention property under pressure, that is, in order to reduce re-wet. In particular, a proportion of particles having a particle diameter of not less than 710 µm is preferably not more than 5 weight % because, with such a proportion, the gap fluid retention property under pressure will not decrease excessively. The particle size distribution can be controlled by the pulverization step and the classification step.

(2-6) Surface-Crosslinking Step (Step (6))

This step is carried out in order to improve liquid permeability and water absorption speed in the water-absorbing resin (water-absorbing resin powder) after drying and classification. This step is a step of causing a part of a surface layer of water-absorbing resin powder obtained through the above steps (i.e., a part up to several tens of micrometers deep from a surface of the water-absorbing resin powder) to have a higher crosslinking density.

The surface-crosslinking step is constituted by a mixing step, a heat treatment step, and a cooling step (optional). In a case where particle size is controlled during polymerization, as is the case with reversed phase suspension polymerization, vapor phase polymerization, spray polymerization, and droplet polymerization, the pulverization and classification steps prior to the surface-crosslinking step are unnecessary, and the below-described heat treatment step can be carried out simultaneously with the drying step.

In the surface-crosslinking step, a water-absorbing resin (water-absorbing resin particles) can be obtained which has been surface-crosslinked by radical crosslinking on the surface of the water-absorbing resin powder, surface polymerization on the surface of the water-absorbing resin powder, cross-linking reaction with a surface-crosslinking agent, or the like.

The surface-crosslinking step can be a step of surface-crosslinking the water-absorbing resin powder, obtained through the steps (1) through (5) and having a BET specific surface area of not less than 0.0270 $m^2/g$ and less than 0.0310 $m^2/g$, so that water-absorbing resin particles are obtained. The surface-crosslinking step can be a step of surface-crosslinking the water-absorbing resin powder, obtained through the steps (1) through (5) and having a BET specific surface area of not less than 0.0310 $m^2/g$, so that water-absorbing resin particles are obtained.

(Surface-Crosslinking Agent)

A surface-crosslinking agent used in the present invention is not limited to a particular one. Examples of the surface-crosslinking agent include an organic surface-crosslinking agent and an inorganic surface-crosslinking agent. Among others, an organic surface-crosslinking agent that is reactive with a carboxyl group is preferable, from the viewpoint of the physical properties of a water-absorbing resin and the handleability of the surface-crosslinking agent. For example, one of the surface-crosslinking agents disclosed in U.S. Pat. No. 7,183,456 can be used, or two or more of the surface-crosslinking agents disclosed in U.S. Pat. No. 7,183,456 can be used. Specifically, examples of the surface-crosslinking agent encompass a polyhydric alcohol compound, an epoxy compound, a haloepoxy compound, a polyamine compound, a condensed product with a haloepoxy compound of the polyamine compound, an oxazoline compound, an oxazolidinone compound, a polyvalent metal salt, an alkylene carbonate compound, a cyclic urea compound, and the like.

An amount of the surface-crosslinking agent used (or a total amount used in a case where a plurality of surface-crosslinking agents are used) is preferably 0.01 parts by weight to 10 parts by weight, more preferably 0.01 parts by weight to 5 parts by weight, per 100 parts by weight of the water-absorbing resin powder. The surface-crosslinking agent is preferably added as an aqueous solution. In such a case, an amount of water used is preferably 0.1 parts by weight to 20 parts by weight, more preferably 0.5 parts by weight to 10 parts by weight per 100 parts by weight of the water-absorbing resin powder. In a case where a hydrophilic organic solvent is used according to need, an amount of the hydrophilic organic solvent used is preferably equal to or less than 10 parts by weight, and more preferably equal to or less than 5 parts by weight per 100 parts by weight of the water-absorbing resin powder.

It is possible to mix liquid permeability improving agents, which are added in a "step of adding liquid permeability improving agent" described below, with the surface-crosslinking agent (aqueous solution) by adding each of the additives in a range of equal to or less than 5 parts by weight. Alternatively, it is possible to add the additives to the water-absorbing resin powder and the surface-crosslinking agent in a different mixing step described below.

(Mixing Step)

This step is a step of mixing the water-absorbing resin powder and the surface-crosslinking agent. A method of mixing the surface-crosslinking agent is not limited to a particular one and can be a method in which a surface-crosslinking agent solution is prepared in advance, and the surface-crosslinking agent solution is mixed with the water-absorbing resin powder preferably by spraying or dropping the surface-crosslinking agent solution onto the water-absorbing resin powder, more preferably by spraying the surface-crosslinking agent solution onto the water-absorbing resin powder.

The above mixing may be performed with use of any device. The device is preferably a high-speed stirring mixer, more preferably a high-speed stirring continuous mixer.

(Heat Treatment Step)

This step is a step of heating a mixture, which has been obtained in the mixing step, so as to cause cross-linking reaction on a surface of the water-absorbing resin powder.

An apparatus for causing the cross-linking reaction is not limited to a particular one and can be preferably a paddle dryer. A reaction temperature in the cross-linking reaction is set as appropriate according to a type of a used surface-crosslinking agent, and is preferably 50° C. to 300° C., and more preferably 100° C. to 200° C.

(Cooling Step)

This step is an optional step which is carried out after the heat treatment step if needed.

An apparatus for carrying out the cooling is not limited to a particular one and is preferably an apparatus whose specification is identical with that of an apparatus used in the heat treatment step, and more preferably a paddle dryer. This is because such an apparatus can be used as a cooling apparatus by changing a heating medium to a cooling medium. Note that, according to need, the water-absorbing resin particles obtained in the heat treatment step are force-cooled in the cooling step to a temperature preferably of 40° C. to 80° C., and more preferably of 50° C. to 70° C.

(2-7) Step of Adding Liquid Permeability Improving Agent (Step (7))

This step is a step of adding, to the water-absorbing resin particles obtained in the surface-crosslinking step, at least one liquid permeability improving agent selected from the group consisting of a polyvalent metal cation, a cationic polymer, and inorganic fine particles, each of which are described below. Note that, normally, a water-absorbing resin obtained through the step (7) is a final product. This final product, which is a water-absorbing resin, is herein referred to as a "water-absorbing agent." The term "water-absorbing agent" is also used to refer to a final product obtained without adding the above liquid permeability improving agent(s), specifically, a final product which is water-absorbing resin particles obtained in the surface-crosslinking step.

Adding the liquid permeability improving agent(s) to the water-absorbing resin particles improves the liquid permeability of a water-absorbing agent to be obtained. The gap fluid retention property under pressure, however, will deteriorate. The liquid permeability and the gap fluid retention property under pressure are also affected by the BET specific surface area of a water-absorbing resin powder. As such, it is possible to adjust the liquid permeability and gap fluid retention property under pressure of a water-absorbing agent to be obtained by adjusting an added amount of the liquid permeability improving agent(s) and by adjusting the BET specific surface area.

Note that the liquid permeability improving agent(s) is added in the form of aqueous solution or slurry liquid, and therefore the water-absorbing resin particles are swollen by water again. Therefore, this step is also referred to as "remoistening step". Moreover, as described earlier, the liquid permeability improving agent(s) can be mixed with the water-absorbing resin powder simultaneously with the surface-crosslinking agent (aqueous solution).

Two or more of the above-described liquid permeability improving agents can be used together, in accordance with the desired water absorption performance of a water-absorbing agent to be obtained. In such a case, the added amount of the liquid permeability improving agents is not particularly limited, but it is preferable that each of the liquid permeability improving agents does not exceed the respective ranges indicated below, and more preferable that each of the liquid permeability improving agents does not exceed a value which is 80% of the respective ranges indicated below.

Note that the term "liquid permeability improving agent" refers to a compound, which increases (improves) saline flow conductivity SFC of a water-absorbing resin as observed before and after this step (step of adding liquid permeability improving agent). Each compound will be discussed below.

(Polyvalent Metal Cation)

The polyvalent metal cation used in the present invention is has a valence of preferably two or more, more preferably two to four, and even more preferably three or four. Specific examples of the polyvalent metal to be used include aluminum and zirconium. Examples of a compound (for example, polyvalent metal salt) used as a raw material of the polyvalent metal cation include aluminum lactate, aluminum sulfate, and zirconium sulfate. Of these, aluminum sulfate is preferable from the viewpoint of handleability and the like.

With regards to a used amount (added amount) of the polyvalent metal cation, in a case where the BET specific surface area of the water-absorbing resin powder is not less than 0.027 m$^2$/g and less than 0.031 m$^2$/g, an amount of polyvalent metal atoms is preferably less than $1.40 \times 10^{-5}$ mol/g and more preferably less than $1.00 \times 10^{-5}$ mol/g. In a case where the BET specific surface area of the water-absorbing resin powder is not less than 0.031 m$^2$/g, an amount of polyvalent metal atoms is preferably less than $3.60 \times 10^{-5}$ mol/g, more preferably less than $1.40 \times 10^{-5}$ mol/g, and even more preferably less than $1.00 \times 10^{-5}$ mol/g.

Note that the above used amounts are relative to 1 g of the water-absorbing resin powder. Furthermore, in a case where, for example, the compound used as the raw material of the polyvalent metal cation is an aluminum salt of aluminum sulfate or the like, the term "polyvalent metal atoms" refers to aluminum atoms.

(Cationic Polymer)

The cationic polymer used in the present invention is not limited to a particular one and can be one disclosed in, for example, U.S. Pat. Nos. 5,382,610, 7,098,284, International Publication No. 2009/110645, International Publication No. 2009/041731, and International Publication No. 2009/041727. Among others, polyethylene imine, polyvinyl amine, polyallylamine, or a condensate of dimethylamine, ammonia, and epichlorohydrin (a dimethylamine-ammonia-epichlorohydrin resin) is preferable.

A weight average molecular weight of the cationic polymer is preferably 1,000 to 5,000,000, more preferably 2,000 to 1,000,000, and even more preferably 10,000 to 500,000. Furthermore, the cationic polymer is preferably water-soluble. Here, "water-soluble" means that 1 g or more will dissolve in 100 g of water at 25° C.

A used amount (added amount) of the cationic polymer, in a case where the BET specific surface area of the water-absorbing resin powder is not less than 0.027 m$^2$/g and less than 0.031 m$^2$/g, is preferably less than 2.0 weight % and more preferably less than 1.0 weight %, relative to solid content of the water-absorbing resin powder. In a case where the BET specific surface area of the water-absorbing resin powder is not less than 0.031 m$^2$/g, the used amount of the cationic polymer is preferably less than 2.5 weight %, more preferably less than 2.0 weight %, and even more preferably less than 1.0 weight %, relative to solid content of the water-absorbing resin powder.

Adding the cationic polymer to the water-absorbing resin particle improves the liquid permeability of the water-absorbing agent to be obtained. The cationic polymer may be mixed directly with the water-absorbing resin particles. Alternatively, a solution (particularly an aqueous solution) of the cationic polymer may be mixed with the water-absorbing resin particles, or the cationic polymer may first be dissolved into a surface-crosslinking agent or a solution of a surface-crosslinking agent before being mixed with the water-absorbing resin particles.

(Inorganic Fine Particles)

Preferable examples of inorganic fine particles used in the present invention include silicon dioxide and the like. Specific examples include the inorganic fine particles disclosed in U.S. Pat. No. 7,638,570 and the like. Examples of such inorganic fine particles include the dry silica and the hydrophilic fumed silica which are disclosed in the Examples.

A used amount (added amount) of the inorganic fine particles, in a case where the BET specific surface area of the water-absorbing resin powder is not less than 0.027 m$^2$/g and less than 0.031 m$^2$/g and the inorganic fine particles have a primary particle diameter of less than 20 nm, is preferably less than 0.3 weight % and more preferably less than 0.2 weight/n %, relative to solid content of the water-absorbing resin powder. The used amount (added amount) of the inorganic fine particles, in a case where the BET specific surface area of the water-absorbing resin powder is in the above range and the inorganic fine particles have a primary particle diameter of not less than 20 nm, is preferably less than 1.0 weight % and more preferably less than 0.5 weight %, relative to solid content of the water-absorbing resin powder.

The used amount (added amount) of the inorganic fine particles, in a case where the BET specific surface area of the water-absorbing resin powder is not less than 0.031 m$^2$/g and the inorganic fine particles have a primary particle diameter of less than 20 nm, is preferably less than 1.2 weight %, more preferably less than 1.0 weight %, and even more preferably less than 0.5 weight %, relative to solid content of the water-absorbing resin powder. The used amount (added amount) of the inorganic fine particles, in a case where the BET specific surface area of the water-absorbing resin powder is in the above range and the inorganic fine particles have a primary particle diameter of not less than 20 nm, is preferably less than 2.0 weight %, more preferably less than 1.5 weight %, and even more preferably less than 1.0 weight %, relative to solid content of the water-absorbing resin powder.

Adding the inorganic fine particles to the water-absorbing resin particles improves the liquid permeability of the water-absorbing agent to be obtained.

(2-8) Step of Adding Other Additive

In the present invention, an additive other than the above described additives (hereinafter, "other additive") can be added in order to give various functions to the water-absorbing agent to be obtained.

Specific examples of the other additive include a chelating agent, an inorganic reducing agent, an α-hydroxycarboxylic acid compound, a surfactant, a compound having a phosphorus atom, an oxidizer, an organic reducing agent, organic powder such as metallic soap, a deodorant agent, an antibacterial agent, pulp, and thermoplastic fibers. The other additive can be mixed with the water-absorbing resin powder or the water-absorbing resin particles simultaneously with the surface-crosslinking agent or the liquid permeability improving agent. The other additive can alternatively be added during any step of producing a polyacrylic acid (salt)-based water-absorbing resin.

(Chelating Agent)

In the present invention, from the viewpoint of color (coloring prevention), deterioration prevention, and the like in the water-absorbing agent to be obtained, it is preferable to add a chelating agent. Specifically, a compound and an amount used thereof disclosed in "[2] Chelating agent" of International Publication No. 2011/040530 can be applied to the present invention.

(Inorganic Reducing Agent)

In the present invention, from the viewpoint of color (coloring prevention), deterioration prevention, reduction in residual monomer, and the like in the water-absorbing agent to be obtained, it is preferable to add an inorganic reducing agent. Specifically, a compound and an amount used thereof disclosed in "[3] Inorganic reducing agent" of International Publication No. 2011/040530 can be applied to the present invention.

(α-Hydroxycarboxylic Acid Compound)

In the present invention, from the viewpoint of color (coloring prevention) and the like in the water-absorbing agent to be obtained, it is preferable to add α-hydroxycarboxylic acid. Note that the "α-hydroxycarboxylic acid compound" is carboxylic acid having a hydroxyl group in a molecule or is a salt thereof, and is hydroxycarboxylic acid having a hydroxyl group at an alpha position. Specifically, a compound and an amount used thereof disclosed in "[6] α-hydroxycarboxylic acid compound" of International Publication No. 2011/040530 can be applied to the present invention.

(Surfactant)

In the present invention, from the viewpoint of, for example, reducing process damage during a production process, it is preferable to add a surfactant. Specifically, a compound and an amount used thereof disclosed in International Publication No. 2005/075070 can be applied to the present invention. More specific details are as disclosed in "(2-1) Step of preparing aqueous monomer solution" above.

(Compound Having a Phosphorus Atom, Other)

In the present invention, additives such as a compound having a phosphorus atom, an oxidizer, an organic reducing agent, an organic powder such as metallic soap, a deodorant agent, an antibacterial agent, pulp, and thermoplastic fibers can be added as appropriate in accordance with the performance of the water-absorbing agent to be obtained. As such, a used amount (added amount) of such an additive is determined as appropriate according to a purpose of use of the water-absorbing agent to be obtained and is therefore not limited to a particular one. The used amount (added amount) of such an additive is preferably not more than 3 parts by weight, and more preferably not more than 1 part by weight, per 100 parts by weight of the water-absorbing resin powder.

(2-9) Other Steps

In the present invention, in addition to the above described steps, it is possible to carry out a granulation step, a sizing step, a fine powder removal step, a fine powder recycling step, and the like according to need. Moreover, it is possible to further carry out one or more of a transportation step, a storing step, a packing step, a reserving step, and the like. Note that the "sizing step" encompasses a fine powder removal step subsequent to the surface-crosslinking step and a step of carrying out classification and pulverization in a case where a water-absorbing resin is aggregated to have a size larger than an intended size. The "fine powder recycling step" encompasses an aspect in which fine powder is added as is, and also a step of adding the fine powder, in the form of a large hydrogel, during any of the steps for producing the water-absorbing resin.

[3] Physical Properties of Water-Absorbing Agent (Novel Water-Absorbing Agent)

A water-absorbing agent in accordance with the present invention is a water-absorbing agent including: a polyacrylic acid (salt)-based water-absorbing resin as a main component, the water-absorbing agent satisfying (A) to (C) below: (A) a saline flow conductivity (SFC) is not less than $20 \times 10^{-7} \cdot cm^3 \cdot s \cdot g^{-1}$; (B) a gap fluid retention property under pressure is not less than 9 g/g; and (C) a proportion of particles having a particle diameter of not less than 150 μm and less than 710 μm is less than 90 weight %. The gap fluid retention property under pressure of (B) is a weight of a gap fluid within a gel swollen in a 0.69 weight % aqueous sodium chloride solution under a load of 0.3 psi (2.07 kPa) per gram of the water-absorbing agent. In other words, when a water-absorbing resin is swollen in a 0.69 weight % aqueous sodium chloride solution, the gap fluid retention property under pressure is a weight of the aqueous sodium chloride solution per gram of the water-absorbing agent, the sodium chloride solution being retained in gaps within the water-absorbing agent under a load of 2.07 kPa (0.3 psi).

It was found that, by satisfying all of the physical properties of (A) through (C) above, the water-absorbing agent in accordance with the present invention reduces re-wet in an absorbent article such as a disposable diaper when used for an absorbent body thereof.

In general, in a case where there is a large amount of gap fluid, applying pressure will cause the gap fluid to be expelled, thus presumably causing an increase in re-wet. However, this phenomenon occurs in a case when there is a large amount of gap fluid when no load is applied. The water-absorbing agent in accordance with the present invention, however, can hold a large amount of gap fluid while under pressure. That is, even when under a load, the water-absorbing agent in accordance with the present invention can hold liquid in gaps between swollen gel particles of the water-absorbing agent. As such, in addition to the amount of liquid absorbed by the water-absorbing agent itself, liquid is also retained in gaps between gel particles of the water-absorbing agent, thereby making it possible to reduce re-wet. With regards to re-wet of the water-absorbing agent in accordance with the present invention, a preferable value of re-wet under pressure is described in "(I) Re-wet under pressure" below.

Note that the water-absorbing agent in accordance with the present invention preferably contains a liquid permeability improving agent disclosed in section (2-7) above. In a case where the liquid permeability improving agent is a polyvalent metal cation, content of polyvalent metal atoms per gram of water-absorbing agent is preferably less than $3.60 \times 10^{-5}$ mol/g. In a case where the liquid permeability improving agent is a cationic polymer, content thereof is preferably less than 2.5 weight %. In a case where the liquid permeability improving agent is inorganic fine particles having a primary particle diameter of less than 20 nm, content thereof is preferably less than 1.2 weight %. In a case where the liquid permeability improving agent is inorganic fine particles having a primary particle diameter of not less than 20 nm, content thereof is preferably less than 2.0 weight %. Note that the above content values are relative to solid content of the water-absorbing resin powder.

The water-absorbing agent in accordance with the present invention can further contain a surfactant and/or dispersant disclosed in section (2-1) above.

(Further Preferable Physical Properties)

The water-absorbing agent in accordance with the present invention preferably further satisfies (D) to (H) below: (D) a centrifuge retention capacity (CRC) is not less than 25 g/g; (E) a fluid retention capacity under pressure (AAP) is not less than 20 g/g; (F) a water absorption speed (FSR) is not less than 0.25 g/g/s; (G) a weight average particle diameter (D50) is 300 μm to 450 μm; and (H) a logarithmic standard deviation (σζ) of a particle size distribution is 0.25 to 0.45.

Note that the water-absorbing agent in accordance with the present invention need only satisfy all of (A) to (C) above. However, in a case where the water-absorbing agent is used for an absorbent body of an absorbent article such as a disposable diaper, it is desirable to control, in addition to (A) to (C) above, at least one of the physical properties of (D) to (H), preferably not less than two of the physical properties, including the AAP, of (D) to (H); more preferably not less than three of the physical properties, including the AAP, of (D) to (H); even more preferably not less than four of the physical properties, including the AAP, of (D) to (H); and especially even more preferably all five of the physical properties, such that the physical properties each fall within a desired range. Specifically, it is preferable to control each of the physical properties of (A) through (H) so as to fall within the below preferable ranges.

Having physical properties which satisfy the below ranges allows the water-absorbing agent in accordance with the present invention to achieve effects of the present invention and to achieve sufficient performance in a high-concentration disposable diaper (i.e., a disposable diaper having a high amount of water-absorbing agent used per disposable diaper). The following description will discuss preferable ranges of each physical property and the like.

(A) Saline Flow Conductivity (SFC)

The water-absorbing agent in accordance with the present invention has a saline flow conductivity (SFC) of not less than 20, preferably not less than 50, more preferably not less than 70, and even more preferably not less than 80. An upper limit value is not particularly limited, but is preferably not more than 3,000 and more preferably not more than 2,000. As such, a typical range of the saline flow conductivity (SFC) can be selected as appropriate within a range expressed by the above upper and lower limit values. For example, the range of the saline flow conductivity (SFC) can be a discretionarily selected range, such as 20 to 3,000, 50 to 3,000, or 80 to 2,000. Note that a unit of the saline flow conductivity (SFC) is $\times 10^{-7} \cdot cm^3 \cdot s \cdot g^{-1}$.

A water-absorbing agent having a saline flow conductivity (SFC) of less than $20 \times 10^{-7} \cdot cm^3 \cdot s \cdot g^{-1}$ has a low liquid permeability with respect to, for example, bodily fluids such as urine or blood, and is therefore not suitable for an absorbent body of an absorbent article such as a disposable diaper. With a water-absorbing agent having a saline flow conductivity (SFC) of not more than $3,000\times10^{-7}\cdot cm^3\cdot s\cdot g^{-1}$, however, there is no risk of liquid leakage being caused by insufficient absorption of, for example, bodily fluids such as urine or blood. Such a water-absorbing agent is therefore suitable for an absorbent body of an absorbent article such as a disposable diaper. Note that saline flow conductivity (SFC) is generally controlled by, for example, particle size, surface crosslinking, and a liquid permeability improving agent.

(B) Gap Fluid Retention Property Under Pressure

The water-absorbing agent in accordance with the present invention has a gap fluid retention property under pressure of not less than 9 g/g, and preferably of not less than 10 g/g. An upper limit value is not particularly limited, but is preferably not more than 19 g/g. As such, a typical range of the gap fluid under pressure can be selected as appropriate within a range expressed by the above upper and lower limit values. For example, the range of the gap fluid retention property under pressure can be a discretionarily selected range, such as 9 g/g to 19 g/g, or 10 g/g to 19 g/g.

In a case where a water-absorbing agent having a gap fluid retention property under pressure of less than 9 g/g is used for an absorbent body of an absorbent article such as a disposable diaper, when the water-absorbing agent is under pressure, there is a risk of liquid leakage due to insufficient absorption of, for example, bodily fluids such as urine or blood. Such a water-absorbing agent is therefore not suitable for an absorbent body of an absorbent article such as a disposable diaper (C) Proportion of Particles with Particle Diameters of not Less than 150 μm and Less than 710 μm In the water-absorbing agent in accordance with the present invention, a proportion of particles having a particle diameter of not less than 150 μm and less than 710 μm is not less than 90 weight %, preferably not less than 95 weight %, more preferably not less than 97 weight %, and even more preferably not less than 98 weight %.

In a water-absorbing agent in which a proportion of such particles is less than 90 weight %, there is an excessive amount of fine particles and coarse particles. This causes not only a decrease in the amount of liquid absorbed by the water-absorbing agent itself, but also a decrease in the amount of liquid which can be retained in gaps between gel particles. As a result there is an increase in re-wet. Such a water-absorbing agent is therefore not suitable for an absorbent body of an absorbent article such as a disposable diaper.

In order to increase the gap fluid retention property under pressure, it is important to control particle size distribution. In particular, in a case where particles having a particle diameter of not less than 710 μm are contained at a proportion of not more than 5 weight %, the gap fluid retention property under pressure will not decrease excessively. The particle size distribution can be controlled by the pulverization step and the classification step.

(D) Centrifuge Retention Capacity (CRC)

The water-absorbing agent in accordance with the present invention has a centrifuge retention capacity (CRC) of normally not less than 5 g/g, preferably not less than 15 g/g, and more preferably not less than 25 g/g. An upper limit value of the CRC is not limited and is preferably as high as possible. However, from the viewpoint of the balance between the CRC and other physical properties, the upper limit is preferably not more than not more than 70 g/g, more preferably not more than 50 g/g, and even more preferably not more than 40 g/g. As such, a typical range of the centrifuge retention capacity (CRC) can be selected as appropriate within a range expressed by the above upper and lower limit values. For example, the range of the centrifuge retention capacity (CRC) can be a discretionarily selected range, such as 5 g/g to 70 g/g, 15 g/g to 50 g/g, or 25 g/g to 40 g/g.

A water-absorbing agent having a centrifuge retention capacity (CRC) of not less than 5 g/g can absorb a sufficient amount of liquid and is therefore suitable for an absorbent body of an absorbent article such as a disposable diaper. Furthermore, with a water-absorbing agent having a centrifuge retention capacity (CRC) of not more than 70 g/g, there will not be a decrease in a rate of absorbing a body fluid or the like such as urine or blood. Such a water-absorbing agent is therefore suitably used in a high-speed water absorbing disposable diaper or the like. Note that the centrifuge retention capacity (CRC) can be controlled with use of an internal crosslinking agent, a surface-crosslinking agent, and the like.

(E) Fluid Retention Capacity Under Pressure (AAP)

The water-absorbing agent in accordance with the present invention has a fluid retention capacity under pressure (AAP) of preferably not less than 20 g/g, more preferably not less than 22 g/g, even more preferably not less than 23 g/g, especially even more preferably not less than 24 g/g, and most preferably not less than 25 g/g. An upper limit value of the fluid retention capacity under pressure (AAP) is not particularly limited but is preferably not more than 30 g/g. As such, a typical range of the fluid retention capacity under pressure (AAP) can be selected as appropriate within a range expressed by the above upper and lower limit values. For example, the range of the fluid retention capacity under pressure (AAP) can be a discretionarily selected range, such as 20 g/g to 30 g/g, 22 g/g to 30 g/g, or 25 g/g to 30 g/g.

In a case where a water-absorbing agent has a fluid retention capacity under pressure (AAP) of not less than 20 g/g, there will not be a decrease in an amount of absorbed liquid when pressure is applied during actual use of the water-absorbing agent for an absorbent body of a disposable diaper or the like. Such a water-absorbing agent is therefore suitable for an absorbent body of an absorbent article such as a disposable diaper. Note that the fluid retention capacity under pressure (AAP) can be controlled with use of particle size, surface-crosslinking agent, and the like.

(F) Water Absorption Speed (FSR)

The water-absorbing agent in accordance with the present invention has a water absorption speed (FSR) of preferably not less than 0.10 g/g/s, more preferably not less than 0.15 g/g/s, even more preferably not less than 0.20 g/g/s, and especially even more preferably not less than 0.25 g/g/s. An upper limit value of the water absorption speed (FSR) is not particularly limited but is preferably not more than 5.0 g/g/s, and more preferably not more than 3.0 g/g/s. As such, a typical range of the water absorption speed (FSR) can be selected as appropriate within a range expressed by the above upper and lower limit values. For example, the range of the water absorption speed (FSR) can be a discretionarily selected range, such as 0.10 g/g/s to 5.0 g/g/s, 0.15 g/g/s to 5.0 g/g/s, or 0.20 g/g/s to 3.0 g/g/s.

With a water-absorbing agent having a water absorption speed (FSR) of not less than 0.10 g/g/s, there is no risk of liquid leakage being caused by insufficient absorption of, for example, bodily fluids such as urine or blood. Such a water-absorbing agent is therefore suitable for an absorbent body of an absorbent article such as a disposable diaper. Note that the water absorption speed (FSR) can be controlled by use of foaming polymerization, particle size, and the like.

(G) Weight Average Particle Diameter (D50)

The water-absorbing agent in accordance with the present invention has a weight average particle diameter (D50) which falls in a range of preferably 200 μm to 600 μm, more preferably 200 μm to 550 μm, even more preferably 250 μm to 500 μm, and especially even more preferably 300 μm to 450 μm.

As mentioned above, in order to increase the gap fluid retention property under pressure, it is important to control particle size distribution. Setting the weight average particle diameter (D50) to fall in a range of 200 μm to 600 μm makes it possible to achieve a gap fluid retention property under pressure within a desired range. The weight average particle diameter (D50) can be controlled by the pulverization step and the classification step.

(H) Logarithmic Standard Deviation (σζ) of Particle Size Distribution

The water-absorbing agent in accordance with the present invention has a logarithmic standard deviation (σζ) of a particle size distribution which falls in a range of preferably 0.20 to 0.50, more preferably 0.25 to 0.45, and even more preferably 0.27 to 0.35.

As mentioned above, in order to increase the gap fluid retention property under pressure, it is important to control particle size distribution. Setting the logarithmic standard deviation (σζ) of the particle size distribution to fall in a range of 0.20 to 0.50 makes it possible to achieve a gap fluid retention property under pressure within a desired range. The logarithmic standard deviation (σζ) of the particle size distribution can be controlled by the pulverization step and the classification step.

(I) Re-Wet Under Pressure

The water-absorbing agent in accordance with the present invention has a re-wet under pressure which is preferably as small as possible. A water-absorbing agent having re-wet under pressure of not more than 3 g is sufficient for use for an absorbent body of an absorbent article such as a disposable diaper.

In a case where a water-absorbing agent having a re-wet under pressure of not more than 3 g is used for an absorbent body of an absorbent article such as a disposable diaper, bodily fluids or the like such as urine or blood which have been absorbed will not be expelled when the water-absorbing agent is under pressure, and thus there is little risk of liquid leakage. Such a water-absorbing agent is therefore suitable for an absorbent body of an absorbent article such as a disposable diaper.

Note that in conventional measurements, load conditions are changed so as to differ at the time of absorption of an absorption liquid and at the time of measuring re-wet, such that load at the time of measuring re-wet is larger. This is because it was thought that using such load conditions would make it possible to also measure an amount of absorption liquid which is not absorbed by a water-absorbing agent but which remains on an absorbent body. However, it has been found that such load conditions do not allow for correct evaluation. This is because such load conditions cause problems such as an increase in re-wet due to seeping out of absorption liquid which had been absorbed, and a decrease in re-wet due to gel blocking occurring in a case where the water-absorbing agent has a low gel strength. In the present invention, load conditions are the same at the time of absorption of an absorption liquid and at the time of measuring re-wet. This remedies the above problems and makes it possible to carry out measurements in a state similar to that of actual use. The load conditions used for the present invention also make it possible to easily measure re-wet under pressure by using only a water-absorbing agent, without the need to create an absorbent body.

(J) Water-Soluble Component (Ext)

The water-absorbing agent in accordance with the present invention has a water-soluble component (Ext) of normally not more than 50 weight %, preferably not more than 35 weight %, more preferably not more than 25 weight %, and even more preferably not more than 15 weight %. A lower limit value of the water-soluble component (Ext) is not particularly limited but is preferably 0 weight %, and more preferably approximately 0.1 weight %. As such, a typical range of the water-soluble component (Ext) can be selected as appropriate within a range expressed by the above upper and lower limit values. For example, the range of the water-soluble component (Ext) can be a discretionarily selected range, such as 0 weight % to 50 weight %, 0.1 weight % to 50 weight %, or 0.1 weight % to 35 weight %.

A water-absorbing agent having a water-soluble component (Ext) of not more than 50 weight % has a high gel strength and is likely to have a superior liquid permeability. Such a water-absorbing agent also has less re-wet and is therefore suitable for an absorbent body of an absorbent article such as a disposable diaper. Note that the water-soluble component (Ext) can be controlled by use of an internal crosslinking agent or the like.

(K) Moisture Content

The water-absorbing agent in accordance with the present invention has a moisture content which is preferably greater than 0 weight % and not more than 15 weight %, more preferably 1 weight % to 13 weight %, even more preferably 2 weight % to 10 weight %, and especially even more preferably 2 weight % to 9 weight %.

Controlling the moisture content to fall within the above ranges makes it possible to obtain a water-absorbing agent having superior powder characteristics (e.g., fluidity, transportability, damage resistance, and the like).

(L) Residual Monomers

From the viewpoint of safety, the water-absorbing agent in accordance with the present invention contains residual monomers in an amount of preferably not more than 500 ppm, more preferably not more than 400 ppm, and even more preferably not more than 300 ppm. A lower limit value of the residual monomers is not particularly limited but is preferably 0 ppm, and more preferably approximately 10 ppm. As such, a typical range of the residual monomers can be selected as appropriate within a range expressed by the above upper and lower limit values. For example, the range of the residual monomers can be a discretionarily selected range, such as 0 ppm to 500 ppm, 0 ppm to 300 ppm, or 10 ppm to 400 ppm.

Controlling the residual monomers to fall within the above ranges makes it possible to obtain a water-absorbing agent which causes less irritation to, for example, skin of a human body.

(M) Re-Wet of Model Absorbent Body

A model absorbent body using the water-absorbing agent in accordance with the present invention has re-wet which is preferably as small as possible. A model absorbent body having a re-wet of not more than 1.5 g has sufficient performance for use for an absorbent body of an absorbent article such as a disposable diaper.

In a case where a model absorbent body having a re-wet of greater than 1.5 g is used for an absorbent body of an absorbent article such as a disposable diaper, there is the risk that, similarly to a case where re-wet under pressure exceeds 3 g, bodily fluids or the like such as urine or blood which have been absorbed will be expelled, causing liquid leakage.

As such, such a model absorbent body tends not to be suitable for an absorbent body of an absorbent article such as a disposable diaper. The re-wet of a model absorbent body can be measured by, for example, a method as described in the Examples.

[4] Application of Water-Absorbing Agent

Applications of the water-absorbing agent of the present invention are not particularly limited. However, the water-absorbing agent is preferably used in an absorbent body of absorbent articles such as disposable diapers, sanitary napkins, and incontinence pads. In particular, the water-absorbing agent of the present invention can be used for an absorbent body in high-concentration disposable diapers (i.e., disposable diapers each of which contains a large amount of the water-absorbing resin), which have heretofore had problems such as odor, caused by a raw material, and coloring. Further, in a case where the water-absorbing agent of the present invention is used as an upper layer part of the absorbent body, a significant effect can be expected.

Alternatively, for the absorbent body, it is possible to use an absorbent material such as a pulp fiber, in addition to the water-absorbing resin. In such a case, an amount (core concentration) of the water-absorbing resin contained in the absorbent body preferably falls into a range of 30 weight % to 100 weight %, more preferably 40 weight % to 100 weight %, even more preferably 50 weight % to 100 weight %, further still more preferably 60 weight % to 100 weight %, especially even more preferably 70 weight % to 100 weight/n %, and most preferably 75 weight % to 95 weight %.

In a case where the core concentration falls within the above ranges and the absorbent body is used as an upper layer part of an absorbent article, the absorbent article can maintain cleanness, i.e., a state of being white. Further, in such a case, the absorbent article is excellent in diffusion property with respect to a body fluid or the like such as urine or blood, and therefore improvement in absorption amount can be expected based on efficient liquid distribution.

[5] Method for Evaluating Water-Absorbing Agent

A method for evaluating a water-absorbing agent in accordance with the present invention is, for gel particles obtained by swelling a water-absorbing agent, a method for evaluating liquid release performance of a water-absorbing agent, including a step of: measuring space between gel particles having been swollen, the space occurring in a gel layer constituted by the gel particles. Note that "liquid release performance" as used herein refers to performance relating to release of liquid in a case where a load is applied to a water-absorbing agent which has absorbed liquid. "Liquid release performance" includes, for example, the abovementioned re-wet.

Furthermore, a method, in accordance with the present invention, for measuring the space between gel particles, the method being used for the above method for evaluating, is a method including the steps of: swelling a water-absorbing agent to be subjected to the measuring by causing an aqueous medium under a load to flow on the water-absorbing agent, in an amount that is excess relative to an absorption amount at which the water-absorbing agent becomes saturated, so as to obtain the gel particles; and measuring a weight of the aqueous medium retained in the space between the gel particles and calculating space per unit weight of the water-absorbing agent.

The following description will discuss the above measurement method.

A physical property, of a water-absorbing agent, measured by the above measurement method is gap fluid retention property under pressure. That is, the "calculating space per unit weight of the water-absorbing agent" refers to calculating the gap fluid retention property under pressure. With regards to conditions during measurement of the gap fluid retention property under pressure, an amount of the water-absorbing agent subjected to the measuring is preferably 0.035 g/cm$^2$ to 0.071 g/cm$^2$, more preferably 0.040 g/cm$^2$ to 0.065 g/cm$^2$, and even more preferably 0.045 g/cm$^2$ to 0.060 g/cm$^2$. The amount of the water-absorbing agent is preferably not more than 0.071 g/cm$^2$ because such an amount makes it possible to carry out measurements without a gel layer height exceeding 5 cm. The amount of the water-absorbing agent is preferably not less than 0.035 g/cm$^2$ because such an amount reduces measurement deviations and enables accurate measurements.

A load applied when causing the aqueous medium to flow falls within a range of preferably 1.5 kPa to 4.9 kPa, more preferably 1.8 kPa to 4.0 kPa, and even more preferably 2.0 kPa to 3.0 kPa. The load is preferably not more than 4.9 kPa because with such a load, the aqueous medium is absorbed in a sufficient amount, thus making it easy to discern differences in the gap fluid retention property under pressure. The load is preferably not less than 1.5 kPa because such a load makes it possible to carry out measurements without a gel layer height exceeding 5 cm.

The aqueous medium is preferably an aqueous solution containing a monovalent metal ion. The monovalent metal ion is preferably a sodium ion or a potassium ion, and more preferably a sodium ion. A concentration of the monovalent metal ion contained in the aqueous medium is preferably 0.085 mol/l to 0.256 mol/l, more preferably 0.093 mol/l to 0.175 mol/l, and even more preferably 0.100 mol/l to 0.150 mol/l. The concentration of the metal ion is preferably not more than 0.256 mol/l because with such a concentration, the aqueous medium is absorbed in a sufficient amount, thus making it easy to discern differences in the gap fluid retention property under pressure. The concentration of the metal ion is preferably not less than 0.085 mol/l because such a concentration makes it possible to carry out measurements without a gel layer height exceeding 5 cm.

(Measuring Device and Procedure)

The method for measuring can be carried out using, for example, a measuring device including: a cylinder having mesh at a bottom surface thereof; a loading body which has a weight such that a load applied to the bottom surface of the cylinder is 2.07 kPa and which has holes for causing the aqueous medium to flow in a direction parallel to a direction of movement of the cylinder; and an aqueous medium supplying section for supplying the aqueous medium to the cylinder.

Examples of materials of the mesh include metal, resin, and fiber. The mesh is preferably a stainless steel wire mesh. A mesh size of the mesh is not limited, provided that it is a mesh size such that the water-absorbing agent cannot pass through, but the aqueous medium can pass through. However, the mesh size is preferably 0.01 mm to 0.1 mm, more preferably 0.030 mm to 0.050 mm, and even more preferably 0.038 mm.

The cylinder can be made from metal or resin, but is preferably acrylic. An inner diameter of the cylinder is not limited to a particular one but is preferably 5.0 cm to 10.0 cm, and is more preferably 6.0 cm.

The loading body includes, for example, a piston whose piston head has holes, and a weight. An inner diameter of each of the holes is preferably 1.0 mm to 10.0 mm, more preferably 5.0 mm to 10.0 mm, and even more preferably 9.0 mm. The number of the holes is, for example, preferably 5 to 30, more preferably 10 to 25, and even more preferably 21.

The aqueous medium is most preferably a 0.69 weight % aqueous sodium chloride solution, but a 0.90 weight % aqueous sodium chloride solution can be used. A concentration of not more than 0.50 weight % is not preferable in some cases, as such a concentration could cause an increase in a thickness of a gel layer during measurement, thereby making it impossible to carry out stable measurements.

More specifically, the gap fluid retention property under pressure of the present invention can be measured using a measuring device as below, and by the procedure as below.

Specifically, a measuring device to be used includes: a cylinder (A) having, at a bottom surface thereof, a stainless steel wire mesh whose mesh size is 0.038 mm, the cylinder (A) having an inner diameter of 6.0 cm; a loading body (B) which has a weight such that a load applied to the bottom surface of the cylinder (A) is 2.07 kPa and which has 21 holes through which an aqueous medium (C) can flow from an upper portion of the loading body to a lower portion of the loading body, each of the holes having an inner diameter of 9.0 mm; and an aqueous medium supplying section for supplying, to the cylinder (A), a 0.69 weight % aqueous sodium chloride solution as the aqueous medium (C). The loading body (B), in other words, includes 21 holes for causing the aqueous medium (C) to flow in the direction of gravity, each of the holes having an inner diameter of 9.0 mm.

The measuring device is used to carry out the operations of steps (8) to (13) below, and weights W1, W2, and W3 are obtained. These weights are then used in Equation 6 below to calculate the gap fluid retention property under pressure.

[Math. 6]

$$\text{Gap fluid retention property under pressure (g/g)} = (W2-W3)/W1 \qquad (6)$$

The steps (8) through (13) are: (8) spreading evenly, inside the cylinder (A) and on the stainless steel wire mesh, the water-absorbing agent, a weight (W1; unit: g) of the water-absorbing agent being 1.500 g±0.005 g; (9) placing the loading body (B) onto the water-absorbing agent having been spread; (10) supplying, from the aqueous medium supplying section and into the cylinder (A) onto which the loading body (B) has been placed, a 0.69 weight % aqueous sodium chloride solution as the aqueous medium (C), such that the aqueous medium (C) is caused to permeate the water-absorbing agent for 10 minutes starting from a point in time at which a hydrostatic height measured from a top of the stainless steel wire mesh reaches 5 cm, the hydrostatic height being maintained for the 10 minutes; (11) stopping the supplying of the aqueous medium (C) after the aqueous medium (C) is caused to permeate the water-absorbing agent for the 10 minutes, and then leaving the aqueous medium (C) to sit; (12) measuring a weight (W2; unit: g) of the cylinder (A), without removing the loading body (B) or the gel particles, subsequent to commencement of leaving the aqueous medium (C) to sit, and after the aqueous medium (C) has ceased to fall from the bottom surface of the cylinder (A) for a period of not less than 30 seconds; and (13) measuring a weight (W3; unit: g) of the cylinder (A) after causing filter paper to absorb the aqueous medium (C) retained in gaps between the gel particles by leaving the cylinder (A) on the filter paper for 16 hours±1 hour, without removing the loading body (B) or the gel particles.

Note that in the Examples below, conditions used in measurement of gap fluid retention property under pressure are as follows. Load applied to the water-absorbing agent: 2.07 kPa; concentration of metal ions in the aqueous medium: 0.118 mol/l; and amount of the water-absorbing agent: 0.053 g/cm$^2$.

The aqueous medium supplying section can have, for example, a structure including a storage tank for storing the aqueous medium and a tube (a glass and/or a flexible tube) which connects the storage tank to the cylinder (A).

Note that instruments and the device used for measuring SFC can be used in measuring gap fluid retention property under pressure.

The present invention is not limited to the embodiments, but can be altered by a skilled person in the art within the scope of the claims. The present invention also encompasses, in its technical scope, any embodiment derived by combining technical means disclosed in differing embodiments. Further, it is possible to form a new technical feature by combining the technical means disclosed in the respective embodiments.

EXAMPLES

The following description will discuss the present invention in greater detail on the basis of Production Examples, Examples, and Comparative Examples. Note, however, that the present invention is not limited to the descriptions thereof and that the present invention also encompasses in its scope any Example derived from an appropriate combination of technical means disclosed in different Examples.

The electric devices (including devices used to measure physical properties of a water-absorbing agent) in the Examples and the like each used a 200-V or 100-V electric power supply, unless otherwise specified. Further, the physical properties of a water-absorbing agent were carried out at room temperature (20° C. to 25° C.) and at a relative humidity of 50% RH, unless otherwise specified. The description below may use the symbol "l" or "L" to mean "liter" (indicative of a volume) and the expression "wt %" to mean "weight/n %" for convenience.

[Measurements of Physical Properties of Water-Absorbing Agent]

The following description will discuss physical properties of a water-absorbing agent in accordance with the present invention. In a case where the measurement target is, for example, water-absorbing resin powder, the term "water-absorbing agent" in the description should be replaced with "water-absorbing resin powder", unless otherwise specified.

(A) Saline Flow Conductivity (SFC)

The saline flow conductivity (SFC) of a water-absorbing agent in accordance with the present invention was measured in conformity with a measurement method described in U.S. Pat. No. 5,669,894.

(B) Gap Fluid Retention Property Under Pressure

The gap fluid retention property under pressure of a water-absorbing agent in accordance with the present invention was determined by measuring, under a load of 2.07 kPa (0.3 psi) with use of the measuring device below, an space between gel particles swollen in a physiological saline.

(Device for Measuring Gap Fluid Retention Property Under Pressure)

FIG. 1 illustrates a device suitable for this measurement. FIG. 1 is a schematic cross-sectional view of a measuring device used for measuring gap fluid retention property under pressure. The measuring device included a storage tank 102 having a capacity of approximately 10 L and placed on a laboratory jack 103. The storage tank 102 was equipped with a glass tube 100 having an open lower end and a rubber stopper section 101 both for a function of maintaining a hydrostatic height. With the rubber stopper section 101 removed, the storage tank 102 was capable of being supplied with an additional amount of a liquid to be measured. The storage tank 102 had a liquid outlet. In a case where the storage tank 102 contained a liquid to be measured, the liquid outlet was below the liquid level of the liquid to be measured. The storage tank 102 was also equipped with a glass tube 104 that had a valve 105 and that was connected to the storage tank 102 at the liquid outlet. The liquid to be measured was delivered under control carried out by opening and closing the valve 105. The glass tube 104 was connected to one end of a flexible tube 109, and the other end of the flexible tube 109 was connected to a gap fluid retention property under pressure measuring instrument 106 (which is illustrated in detail in FIG. 2). The gap fluid retention property under pressure measuring instrument 106 was set for delivery of a liquid to be measured. During the measurement, the gap fluid retention property under pressure measuring instrument 106 was placed on a support 108 provided with a stainless-steel wire mesh with a mesh size of 1 mm. The measuring device further included, below the support 108, a collection tank 107 for collecting a liquid to be measured.

The storage tank 102 was positioned at a height adjusted by the laboratory jack 103 so that the lower end of the glass tube 100 was at a height 5 cm above the front surface of the stainless-steel wire mesh on the support 108. Before the gap fluid retention property under pressure measuring instrument 106 was set, the following operation was carried out for adjustment of the hydrostatic height of the liquid to be measured. On the support 108, a 120-mL polypropylene container was placed that had a mark at a height 5 cm above the height at which the polypropylene container was in contact with the support 108. Then, the flexible tube 109 was placed in the polypropylene container. The valve 105 was opened so that a liquid to be measured was poured into the polypropylene container. Then, the laboratory jack 103 was adjusted finely so that the liquid to be measured would stop flowing when the liquid to be measured had a height of 5 cm. The height adjustment may be carried out by means of not the laboratory jack 103 but the glass tube 100.

The flexible tube 109 had an inner diameter that would allow a liquid to be measured to flow to a position above the support 108 at a flow rate of 12 g/s.

FIG. 1 shows the unit on the right (namely, the gap fluid retention property under pressure measuring instrument 106, the collection tank 107, the support 108, and the like) on an increased scale over the unit on the left (namely, the storage tank 102, the laboratory jack 103, and the like) for the drawing to be understood easily.

Figure 2:
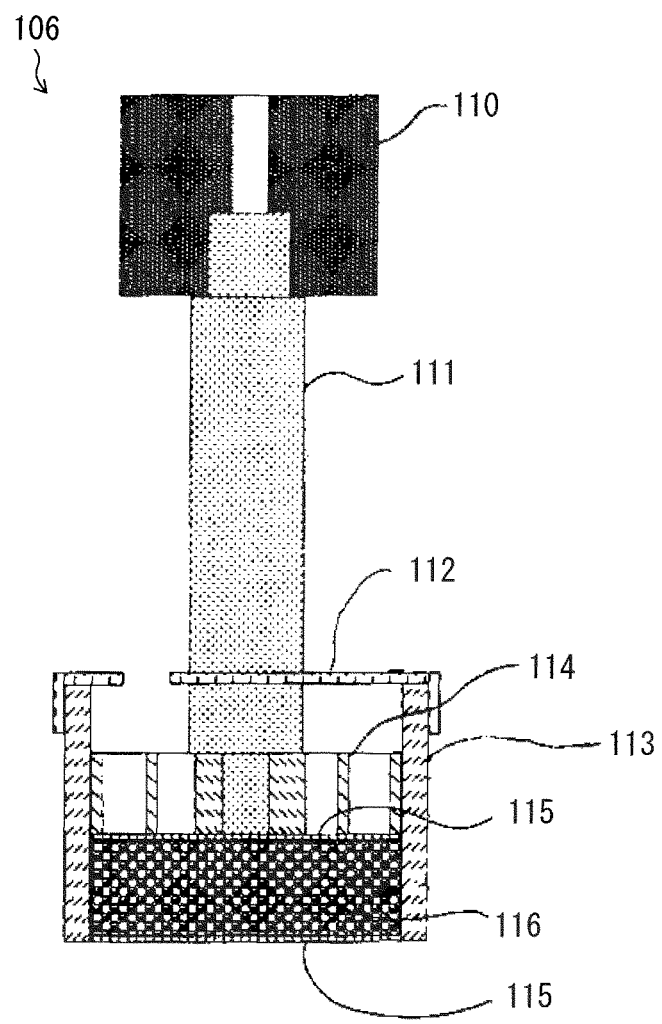
FIG. 2 is a schematic cross-sectional view of a part (gap fluid retention property under pressure measuring instrument) of a measuring device used for measuring gap fluid retention property under pressure.
Figure 3:
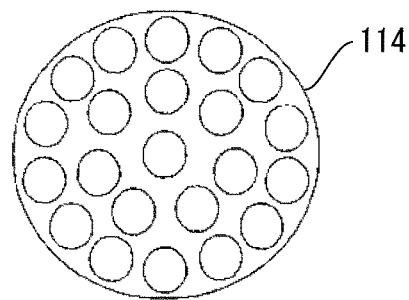
FIG. 3 is a schematic cross-sectional view of a piston head of a measuring device used for measuring gap fluid retention property under pressure.

FIG. 2 is a schematic cross-sectional view of a portion (gap fluid retention property under pressure measuring instrument 106) of a measuring device used for measuring gap fluid retention property under pressure. The gap fluid under pressure measuring instrument 106 basically includes an acrylic cylinder 113 provided with a stainless-steel wire mesh at a lower portion thereof, an acrylic piston 111, an acrylic cover 112 having an opening for insertion of a liquid delivery tube (flexible tube 109), and a weight 110. The acrylic piston 111 includes a piston head 114 having holes as illustrated in FIG. 2. FIG. 3 is a schematic cross-sectional view of a piston head 114 of a measuring device used for measuring gap fluid retention property under pressure. FIG. 3 shows a cross section in the direction perpendicular to the cross section shown in FIG. 2. The holes in the piston head 114 are each in the shape of a cylinder extending through the piston head 114 in its up-down direction (that is, the direction parallel to the direction in which the piston 111 is moved) as illustrated in FIGS. 2 and 3. The piston head 114 has a lower surface to which is bonded a 400-mesh (with a mesh size of 38 µm) wire mesh (available from Weisse & Eschrich; material: SUS304; mesh width: 0.038 mm; wire width: 0.025 mm) 115. The piston head 114 has a diameter slightly smaller than the inner diameter of the acrylic cylinder 113. The piston head 114 is sized such that it is slidable up and down inside the acrylic cylinder 113 without being blocked. The acrylic piston 111 includes a shaft having an upper portion processed so that the weight 110 can be fitted thereon. The acrylic cylinder 113 has an inner diameter of 6.00 cm (with a bottom surface area of 28.27 cm), a wall thickness of 0.5 cm, and a height of 6.0 cm. The acrylic cylinder 113 has a bottom surface to which is bonded a 400-mesh (with a mesh size of 38 µm) wire mesh (available from Weisse & Eschrich; material: SUS304; mesh width: 0.038 mm; wire width: 0.025 mm) 115. During the measurement, the cylinder 113 holds a swollen water-absorbing agent 116 inside itself. The acrylic cover 112 has a hole slightly larger than the outer diameter of the shaft of the acrylic piston 111. The acrylic cover 112 is sized such that the shaft of the acrylic piston 111 is slidable up and down without being blocked. The acrylic cover 112 has an opening for insertion of a liquid delivery tube. The combined weight of the weight 110 and the acrylic piston 111 is adjusted so that a load of 2.07 kPa (0.3 psi) is imposed on the bottom surface of the acrylic cylinder 113.

(Method for Measuring Gap Fluid Retention Property Under Pressure)

For measurement of the gap fluid retention property under pressure of a water-absorbing agent in accordance with the present invention, a 0.69 weight % aqueous sodium chloride solution was prepared as an aqueous medium for use in the measurement. For each measurement, a storage tank 102 having a capacity of approximately 10 L was filled with the above aqueous solution.

First, 1.500±0.005 g of water-absorbing agent was weighed out. The water-absorbing agent had a weight W1 (unit: g; four significant digits). The water-absorbing agent weighed out was spread carefully and uniformly over the entire lower surface of the acrylic cylinder 113. After the water-absorbing agent was spread, the acrylic piston 111, the acrylic cover 112, and the weight 110 were set.

Subsequently, the gap fluid under pressure measuring instrument 106 was placed on the support 108 of the measuring device, and the flexible tube 109 was then inserted into the insertion opening. Next, the valve 105 was opened, which started delivery of a liquid to be measured.

Figure 4:
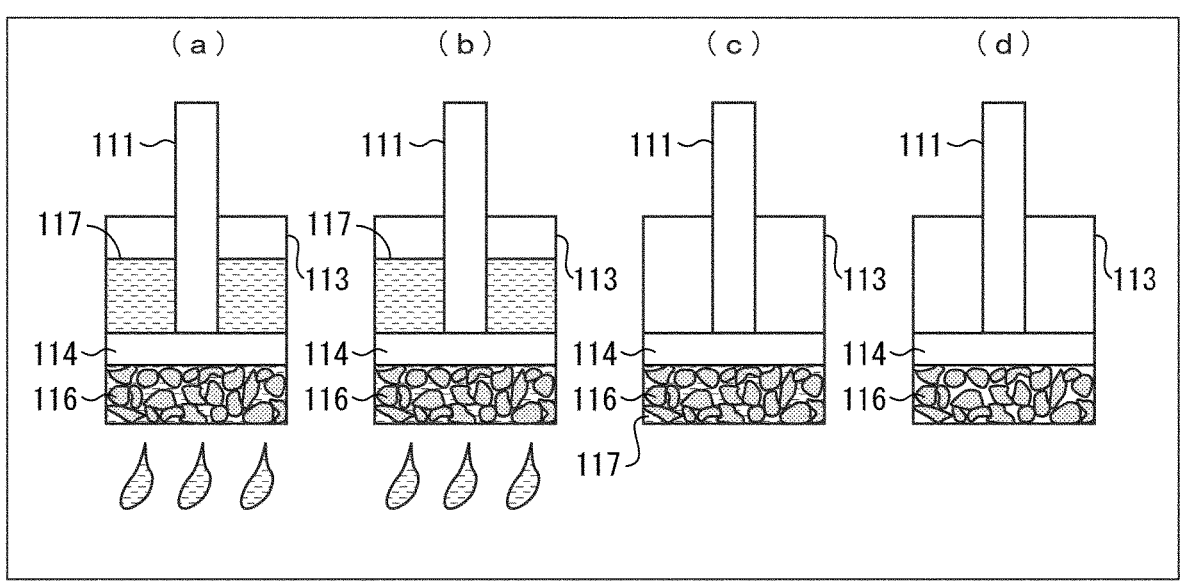
FIG. 4 provides schematic diagrams illustrating a procedure of measuring gap fluid retention property under pressure

FIG. 4 provides schematic diagrams illustrating a procedure of measuring gap fluid retention property under pressure. As illustrated in (a) of FIG. 4, a measurement was started of a liquid permeation time period at a time point at which the hydrostatic height (that is, the height of the liquid 117 to be measured) inside the acrylic cylinder 113 reached 5 cm.

After 10 minutes of liquid permeation, the valve 105 was closed immediately, which achieved the state illustrated in (b) of FIG. 4. After the valve 105 was closed, the liquid to be measured flowed down from the acrylic cylinder 113 of the gap fluid under pressure measuring instrument 106. As illustrated in (c) of FIG. 4, the gap fluid under pressure measuring instrument 106 was weighed at a time point at which no single drop flowed down from the acrylic cylinder 113 over a period of 30 seconds (that is, a time point at which the hydrostatic height inside the acrylic cylinder 113 became equal to the height of a gel layer formed by the swollen water-absorbing agent 116). The gap fluid under pressure measuring instrument 106 had a weight W2 (unit: g; four significant digits). The swollen water-absorbing agent 116 had gaps containing the remainder of the liquid 117 to be measured. The remainder in the gaps was gap water.

Subsequently, five sheets of filter paper (grade: 989; size: 10 cm×10 cm; Ahlstrom) were placed on a horizontal testing bench on top of one another, and the gap fluid under pressure measuring instrument 106 was then placed on the sheets.

After 10 minutes, the gap fluid under pressure measuring instrument 106 was removed and placed on a separate set of five new sheets of filter paper similar to the above that were placed on top of one another. After 16±1 hours, the gap fluid under pressure measuring instrument 106 was weighed. The gap fluid under pressure measuring instrument 106 had a weight W3 (unit: g; four significant digits). The weight W3 is of a gap fluid under pressure measuring instrument containing no gap water as illustrated in (d) of FIG. 4. The above filter paper had specifications described in the EDANA strikethrough test. The gap fluid retention property under pressure was calculated based on Equation (6) below.

[Math. 7]

$$\text{Gap fluid retention property under pressure (g/g)} = (W2-W3)/W1 \quad (6)$$

(C) Proportion of Particles with Particle Diameters of not Less than 150 μm and Less than 710 μm The proportion of particles in a water-absorbing agent in accordance with the present invention which particles each have a particle diameter of not less than 150 μm and less than 710 μm was measured in conformity with an EDANA method (ERT 420.2-02). The proportion of particles each having a particle diameter of not less than 150 μm and less than 710 μm was determined on the basis of a particle size distribution obtained as a result.

(D) Centrifuge Retention Capacity (CRC)

The centrifuge retention capacity (CRC) of a water-absorbing agent in accordance with the present invention was measured in conformity with an EDANA method (ERT 441.2-02).

(E) Fluid Retention Capacity Under Pressure (AAP)

The fluid retention capacity under pressure (AAP) of a water-absorbing agent in accordance with the present invention was measured in conformity with an EDANA method (ERT 442.2-02). Note that the measurement was carried out under a changed load of 49 g/cm² (4.81 kPa).

(F) Water Absorption Speed (FSR)

The water absorption speed (FSR) of a water-absorbing agent in accordance with the present invention was measured in conformity with a measurement method described in International Publication No. 2009/016055.

(G) Weight Average Particle Diameter (D50)

The weight average particle diameter (D50) of a water-absorbing agent in accordance with the present invention was measured in conformity with a measurement method described in U.S. Pat. No. 7,638,570.

The weight average particle diameter (D50) of a particulate crosslinked hydrogel polymer was measured in accordance with the following method.

First, 500 g of a 20 weight % aqueous sodium chloride solution (hereinafter referred to as "EMAL aqueous solution") containing 0.08 weight % EMAL 20C (surfactant, manufactured by Kao Corporation) was introduced into a cylindrical 1-L polypropylene container (with a diameter of 8 cm and a height of 21 cm). Then, 20 g of a particulate hydrogel having a solid content of a weight % (with a temperature of 20° C. to 25° C.) was added to the aqueous solution.

Subsequently, the EMAL aqueous solution was stirred with use of a stirrer tip (with a diameter of 7 mm and a length of 50 mm) at 300 rpm for 60 minutes for preparation of a dispersion liquid.

After the above stirring ended, the dispersion liquid was poured onto a central portion of JIS standard sieves (each with a diameter of 21 cm and a mesh size of 8 mm/4 mm/2 mm/1 mm/0.60 mm/0.30 mm/0.15 mm/0.075 mm) placed on a rotary table. Then, the entire remainder of the particulate hydrogel in the cylindrical container was washed out onto the sieves with use of 100 g of the EMAL aqueous solution.

Subsequently, while the sieves were being rotated manually (at 20 rpm), 6000 g of the EMAL aqueous solution was poured from a height of 30 cm onto the sieves thoroughly with use of a shower nozzle (with 72 holes; liquid amount: 6.0 L/min) in such a manner that the EMAL aqueous solution was poured onto the entire sieves (50 cm²) for classification of the particulate hydrogel.

After the above operation, the particulate hydrogel remaining on each sieve was drained for approximately 2 minutes, and was then weighed. Subsequently, the percentage by weight of the particulate hydrogel remaining on each sieve was calculated from the weight of the particulate hydrogel based on Equations (7) and (8) below.

[Math. 8]

$$X\ (\%) = (w/W) \times 100 \quad (7)$$

[Math. 9]

$$R(\alpha)\ (\text{mm}) = (20/W)^{(1/3)} \times r \quad (8)$$

In Equations (7) and (8) above,

X represents the percentage by weight (unit: weight %) of a particulate hydrogel remaining on each sieve after classification and draining, w represents the weight (unit: g) of a particulate hydrogel remaining on each sieve after classification and draining, W represents the total weight (unit: g) of particulate hydrogels remaining on the respective sieves after classification and draining, R(α) represents the mesh size (unit: mm) of a sieve on the assumption that the particulate hydrogel has a solid content of a weight %, and r represents the mesh size (unit: mm) of a sieve with which a particulate hydrogel swollen in a 20 weight % aqueous sodium chloride solution is classified.

(H) σζ (Logarithmic Standard Deviation of Particle Size Distribution)

The σζ of a water-absorbing agent in accordance with the present invention was measured in conformity with a measurement method described in U.S. Pat. No. 7,638,570.

The σζ of a particulate crosslinked hydrogel polymer was measured in accordance with a method similar to the method described under "(G) Weight average particle diameter (D50)", and the particle size distribution of the particulate hydrogel was plotted on log probability paper.

The particle diameter for a case of cumulative sieve % R=84.1 weight % (referred to as X1) and the particle diameter for a case of cumulative sieve % R=15.9 weight % (referred to as X2) were determined from the above plot, and the logarithmic standard deviation ($\sigma\zeta$) was determined based on Equation (9) below. A smaller $\sigma\zeta$ value means a narrower particle size distribution.

[Math. 10]

$$\sigma\zeta = 0.5 \times \ln(X2/X1) \qquad (9)$$

In Equation (9) above, X1 represents the particle diameter for the case of R=84.1 weight %, and X2 represents the particle diameter for the case of R=15.9 weight %.

(I) Re-Wet Under Pressure

The re-wet under pressure was measured for determining the effect of a particular gap fluid retention property under pressure. The measurement is of a re-wet under a pressure of 2.07 kPa on a 0.9 weight % aqueous sodium chloride solution.

A polyethylene terephthalate sheet having a thickness of 0.3 mm was fused to the bottom of a plastic cylindrical support having an inner diameter of 60 mm. Then, 1.50 g±0.005 g of water-absorbing agent was uniformly dispersed onto this sheet.

On the water-absorbing agent, a metal gauze (cutout of product code: SV-34/30tw; mesh size: 0.034 mm; mesh number: 400; wire diameter: 0.030 mm; available from Asada Mesh Co., Ltd.) having a diameter of 60 mm was placed. Then, a piston and weights as SFC instruments were set.

Next, 35.0 g of a 0.9 weight % aqueous sodium chloride solution was poured onto the piston, and the water-absorbing agent was left to stand still for 5 minutes to be swollen. Subsequently, 10 sheets of filter paper (cutouts of φ 300 mm; available from Toyo Roshi Kaisha, Ltd. of the ADVANTEC group) each having a diameter of 60 mm and a weight (W4, unit: g) measured in advance were inserted between the piston and the metal gauze. The piston and the weights were set again. Then, the water-absorbing agent was left to stand still for 5 minutes so that the re-wet liquid was absorbed by the filter paper.

After 5 minutes, the filter paper was taken out. The gel adhering to the filter paper was removed with use of tweezers, and the filter paper was weighed (W5; unit: g). The re-wet under pressure was calculated based on Equation (10) below.

[Math. 11]

$$\text{Re-wet under pressure (g)} = W5 - W4 \qquad (10)$$

(J) Water-Soluble Component (Ext)

The water-soluble component (Ext) of a water-absorbing agent in accordance with the present invention was measured in conformity with an EDANA method (ERT 470.2-02).

(K) Moisture Content

The moisture content of a water-absorbing agent in accordance with the present invention was measured in conformity with an EDANA method (ERT 430.2-02). For the present invention, the amount of a sample was changed to 1.0 g, and the drying temperature was changed to 180° C. for the measurement. The solid content (unit: weight %) was defined as (100−moisture content).

(L) Residual Monomer

The residual monomer of a water-absorbing agent in accordance with the present invention was measured in conformity with an EDANA method (ERT 410.2-02).

(M) BET Specific Surface Area

The BET specific surface area of water-absorbing resin powder produced by crushing and classifying a dry polymer was measured on the basis of JIS Z 8830. The measurement of the BET specific surface area used a high-accuracy gas/vapor adsorption amount measuring apparatus (BELSORP-max; available from BEL Japan, Inc.), whereas a pre-treatment used an adsorption measuring pre-treatment apparatus (BELSORP-vacII; available from BEL Japan, Inc.). The measurement was made with use of krypton gas as an adsorbate at a temperature of liquid nitrogen. The specific surface area was determined by a BET multipoint method.

(N) Wet Porosity

The wet porosity of a water-absorbing agent in accordance with the present invention was measured in conformity with a measurement method described in International Publication No. 2005/097313.

(O) Re-Wet of Model Absorbent Body

The re-wet of a model absorbent body was measured for determining the effect of using a water-absorbing agent in accordance with the present invention for an absorbent article such as a disposable diaper. The measurement is, similarly to the measurement of the re-wet under pressure, of a re-wet under a pressure of 2.07 kPa on a 0.9 weight % aqueous sodium chloride solution.

Figure 5:
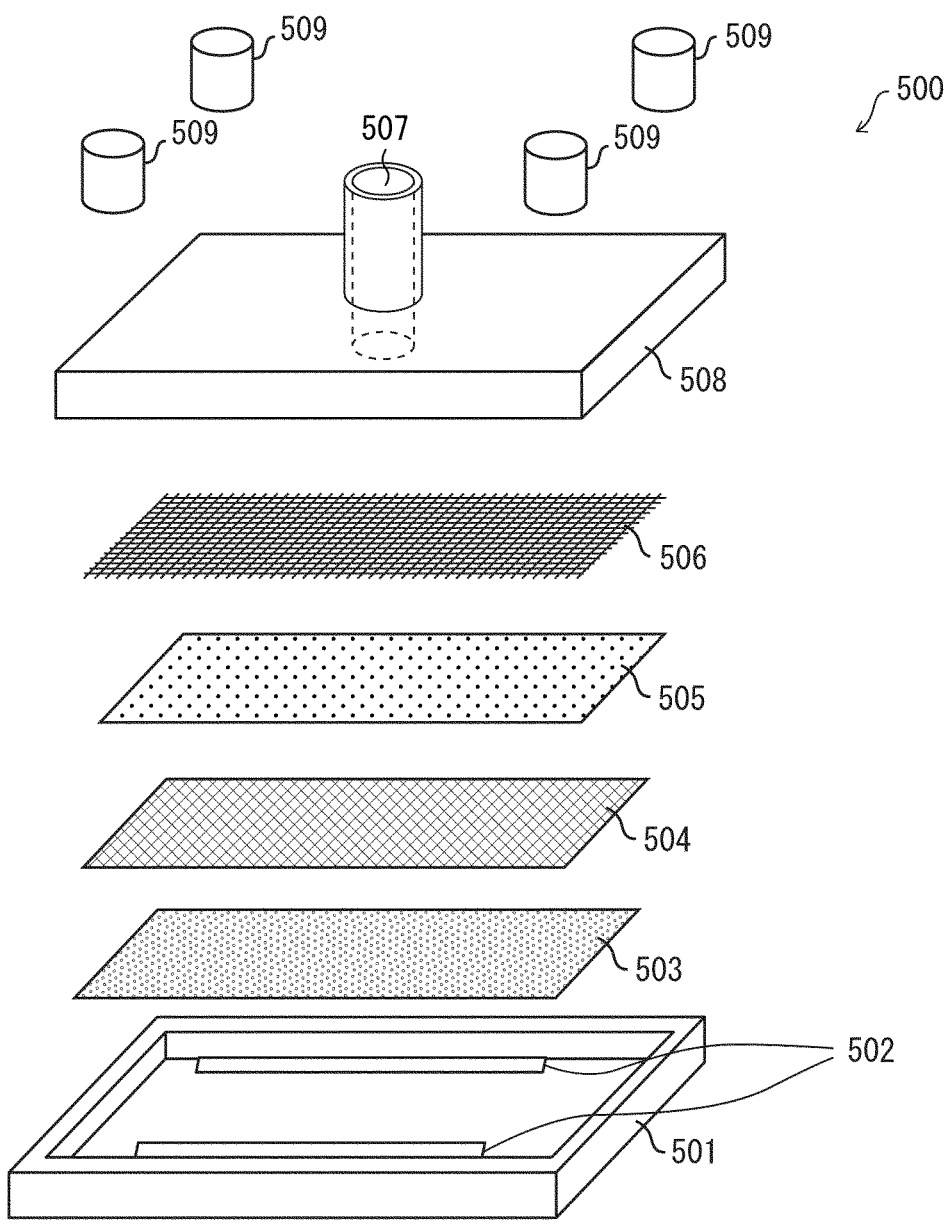
FIG. 5 is a schematic diagram illustrating a configuration of a measuring device used for measuring re-wet of a model absorbent body.

FIG. 5 is a schematic diagram illustrating a configuration of a measuring device 500 used for measuring re-wet of a model absorbent body.

First, to a central portion of an acrylic resin tray 501 having internal dimensions of 401 mm (width)×151 mm (length)×30 mm (height) and external dimensions of 411 mm (width)×161 mm (length)×35 mm (height), two strips of double-side tape (available from Nichiban Co., Ltd.; double-side tape NICETACK NW-10) 502 each having a width of 10 mm and a length of 300 mm were attached in such a pattern as to extend along respective corresponding widthwise inner walls and to be separated from respective widthwise ends by 50 mm. To the double-side tape 502, a water-absorbing sheet 503 that had a thickness of 0.1 mm, a density of 0.14 g/cm³, a width of 300 mm, and a length of 150 mm was attached in such a manner that the water-absorbing sheet 503 was not wrinkled. Then, 13.5 g of a water-absorbing agent 504 was dispersed uniformly (basis weight: 375 g/m²) to an area 15 mm inward of each widthwise inner wall of the acrylic resin tray 501. Before the dispersing, a treatment such as applying an antistatic agent or blowing to the wall surface of the acrylic resin tray 501 was carried out for prevention of static electricity.

A top sheet 505 was placed on the dispersed water-absorbing agent 504. The top sheet 505 was positioned so as to be separated from each lengthwise inner wall of the acrylic resin tray 501 by an equivalent distance and from each widthwise inner wall thereof by an equivalent distance.

The top sheet 505 was a sheet taken out from a Mamy Poko (product name) tape type (size L, purchased in Japan in June 2014; number on the package bottom surface: 404088043) available from Unicharm Corporation. The sheet taken out had a length of 14 cm, a width of 39 cm, and a weight of 3.3 g to 3.6 g. Pulp and the like in the disposable diaper that had adhered to the sheet with an adhesive were sufficiently removed before the use.

A metal gauze 506 (JIS metal gauze; made of stainless steel; 20-mesh) having a width of 390 mm, a length of 90 mm, and a thickness of 0.63 mm was placed on the top sheet 505. Further, an acrylic resin lid 508 (with a width of 400 mm, a length of 150 mm, and a thickness of 20 mm) having, at a central portion thereof, a cylindrical inlet 507 (with a cylindrical portion having a height of 100 mm) having a diameter of 30 mm was placed on the metal gauze 506.

Figure 6:
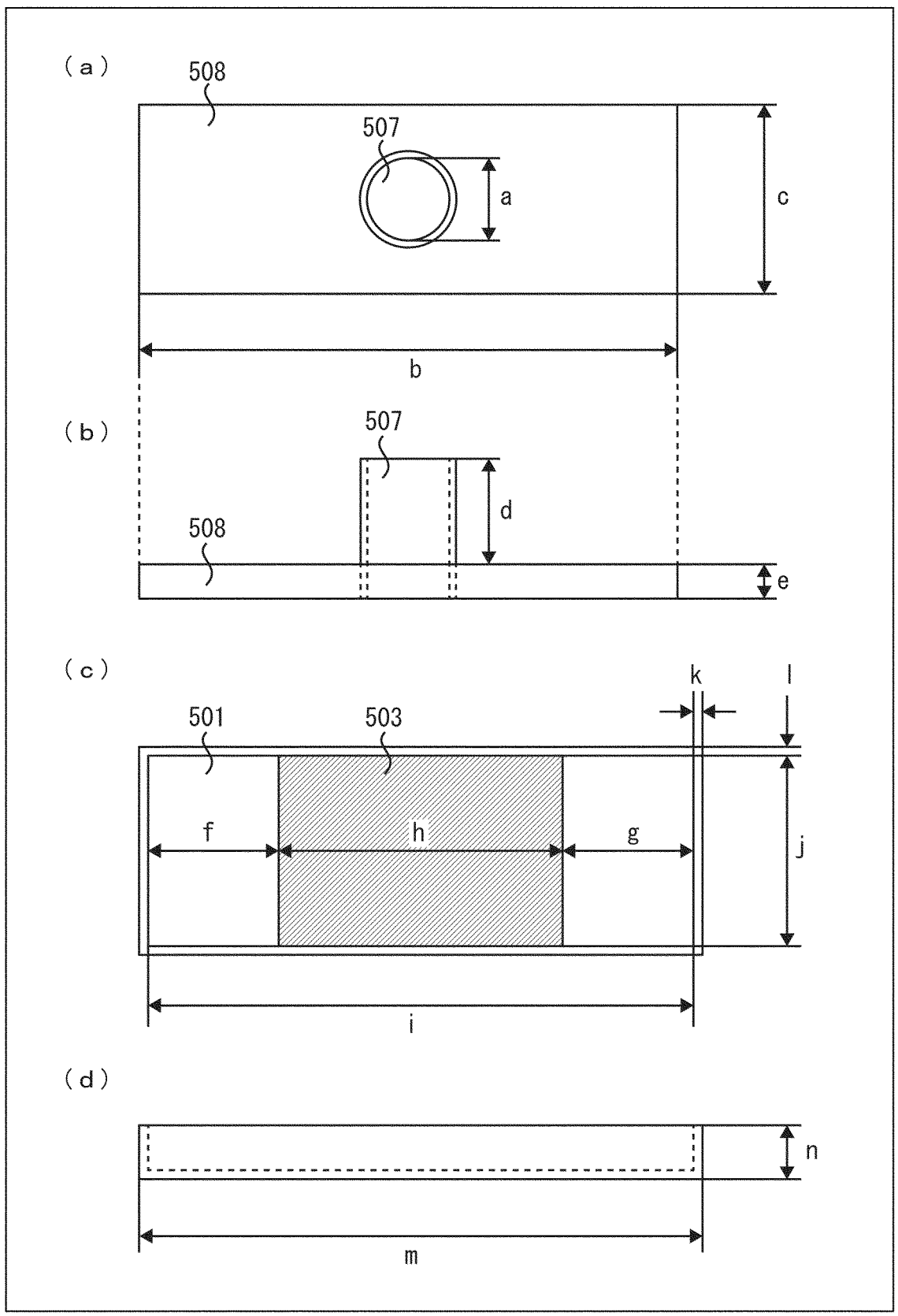
FIG. 6 provides diagrams illustrating respective appearances of a lid and a tray of a measuring device used for measuring re-wet of a model absorbent body. (a) of FIG. 6 is a top view of the lid. (b) of FIG. 6 is a side view of the lid. (c) of FIG. 6 is a top view of the tray. (d) of FIG. 6 is a side view of the tray.

FIG. 6 provides diagrams illustrating respective appearances of a lid and a tray of a measuring device used for measuring re-wet of a model absorbent body. (a) of FIG. 6 is a top view of the lid. (b) of FIG. 6 is a side view of the lid. (c) of FIG. 6 is a top view of the tray. (d) of FIG. 6 is a side view of the tray.

(a) of FIG. 6 shows the symbol "a" to indicate the diameter of the inlet 507, the symbol "b" to indicate the width of the lid 508, and the symbol "c" to indicate the length of the lid 508. (b) of FIG. 6 shows the symbol "d" to indicate the height of the cylindrical portion of the inlet 507 and the symbol "e" to indicate the thickness of the lid 508.

(c) of FIG. 6 shows how the water-absorbing sheet 503 is positioned on the acrylic resin tray 501. (c) of FIG. 6 shows the symbols "f" and "g" to indicate that the water-absorbing sheet 503 is 50.5 mm apart inward from the lengthwise inner walls, the symbol "h" to indicate the width (300 mm) of the water-absorbing sheet 503, the symbol "i" to indicate the widthwise internal dimension (401 mm) of the acrylic resin tray 501, the symbol "j" to indicate the internal length (151 mm) of the acrylic resin tray 501 and the length (151 mm) of the water-absorbing sheet 503, the symbol "k" to indicate the widthwise difference (5 mm) between the internal dimension and external dimension of the acrylic resin tray 501, and the symbol "l" to indicate the lengthwise difference (5 mm) between the internal dimension and external dimension of the acrylic resin tray 501.

(d) of FIG. 6 shows the symbol "m" to indicate the external width (411 mm) of the acrylic resin tray 501 and the symbol "n" to indicate the height (35 mm) of the acrylic resin tray 501.

Weights 509 (material: stainless steel) were placed on the lid 508 for an even load on the water-absorbing agent 504. The respective weights and the like of the weights 509 were adjusted so that the total weight of the metal gauze 506, the acrylic resin lid 508, and the weights 509 was 7578 g (the load applied a pressure of 2.07 kPa to the area in which the water-absorbing resin powder was dispersed).

Then, 75 g of a 0.9 weight % aqueous sodium chloride solution (preferably colored with 0.04 g of blue No. 1 with respect to 1000 g of the aqueous solution) having a temperature adjusted to 37° C.±0.5° C. was introduced over a period of 5 seconds through the inlet 507 into the measuring device 500 for measuring re-wet of a model absorbent body. The aqueous sodium chloride solution introduced was diffused on the metal gauze 506 while passing through the metal gauze 506, and was thereafter absorbed by the water-absorbing agent 504.

Figure 7:
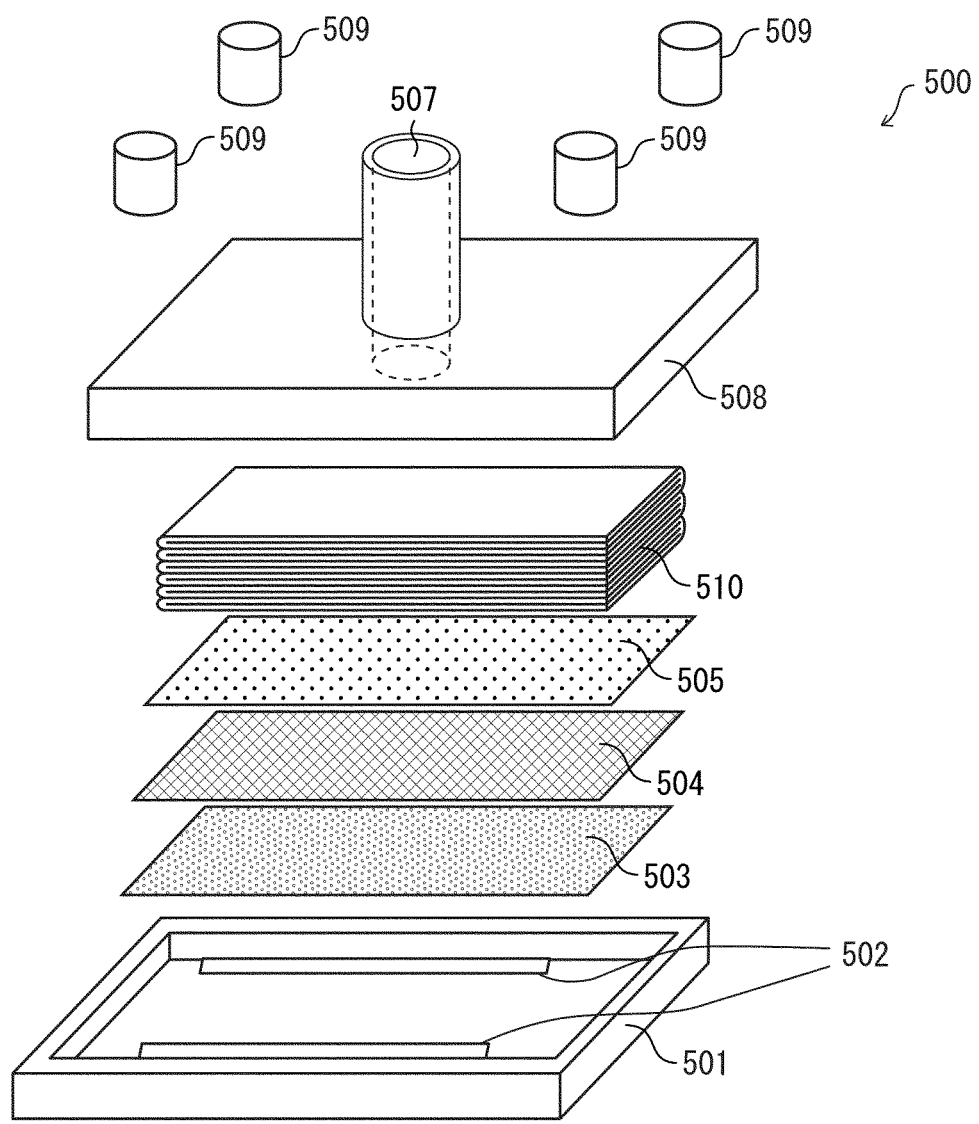
FIG. 7 is a schematic diagram illustrating a configuration of a measuring device used for measuring re-wet of a model absorbent body.

Subsequently, 10 minutes after the start of the first-time introduction of the above aqueous solution, the aqueous solution was introduced for the second time. The aqueous solution retained in the mesh openings of the metal gauze 506 was all absorbed. Similarly, 10 minutes after the start of the second-time introduction, the aqueous solution was introduced for the third time, and was all absorbed as well. FIG. 7 is a schematic diagram illustrating a configuration of a measuring device used for measuring re-wet of a model absorbent body. As illustrated in FIG. 7, 3 minutes after the start of the third-time introduction of the above aqueous solution, the weights 509, the lid 508, and the metal gauze 506 were removed. Then, three sets of a combination of five kitchen towels 510 each two-folded on the short sides (220 mm) (available from Oji Nepia Co., Ltd.; 228 mm×220 mm; two-layered) were weighed to two decimal places so that the weight (W6; unit: g) was recorded. The kitchen towels 510 were placed on a model absorbent body at its center. The metal gauze 506 was not placed on the kitchen towels 510. The weights 509 and the lid 508 were placed on the kitchen towels 510. After 1 minute of standing still, the weights 509, the lid 508, and the kitchen towels 510 were removed from the model absorbent body. The weight (W7; unit: g) of the kitchen towels 510 was recorded to two decimal places. The amount of liquid that the kitchen towels 510 absorbed was calculated from the change in the weight of the kitchen towels 510 in accordance with Equation (11) below. The calculation result was used as re-wet (unit: g) of the model absorbent body.

[Math. 12]

$$\text{Rewet (g) of model absorbent body} = W7 - W6 \qquad (11)$$

Production Example 1

First, 421.7 g of acrylic acid, 2.4 g of polyethyleneglycol diacrylate (molecular weight: 523) as an internal crosslinking agent, 11.3 g of a 1.0 weight % aqueous diethylenetriamine pentaacetic acid/trisodium solution, 140.4 g of a 48.5 weight % aqueous sodium hydroxide solution, and 394.7 g of deionized water (ion-exchange water) were introduced into a 2-liter polypropylene container, and were mixed with one another for preparation of an aqueous monomer solution (a'). The temperature of the aqueous monomer solution (a') rose to 62.5° C. due to heat of neutralization at a first stage immediately after the preparation.

Next, the aqueous monomer solution (a') was cooled while being stirred. At a time point at which the liquid temperature reached 38° C., 211.9 g of a 48.5 weight % aqueous sodium hydroxide solution having a temperature adjusted to 40° C. was added to the aqueous monomer solution (a'), and was mixed therewith for preparation of an aqueous monomer solution (a). At the time of the preparation, the temperature of the aqueous monomer solution (a) rose to 81.0° C. due to heat of neutralization at a second stage immediately after the preparation. While a deposit was observed immediately after the start of the mixing of the 48.5 weight % aqueous sodium hydroxide solution, the deposit was then gradually dissolved, with the result of a transparent uniform solution.

Next, 17.6 g of a 4.0 weight % aqueous sodium persulfate solution was added to the aqueous monomer solution (a) being stirred. Immediately after that, the resulting solution was poured in an atmospheric air open system into a stainless-steel butt vessel (with a bottom surface of 340 mm×340 mm and a height of 25 mm; inner surface: Teflon (registered trademark) coating). The aqueous monomer solution (a) started being poured into the butt vessel 55 seconds after the start of the second-stage neutralization. The butt vessel was heated with use of a hot plate (NEO HOTPLATE HI-1000; available from Iuchi Seiei Do Ltd.) until the surface temperature of the butt vessel reached 40° C.

Then, 60 seconds after the aqueous monomer solution (a) was poured into the butt vessel, a polymerization reaction started. This polymerization reaction proceeded with water vapor being generated and the mixture swelling and foaming in various directions. The mixture was then shrunk to a size slightly larger than the size of the butt vessel. Then, 3 minutes after the start of the polymerization reaction, the resulting crosslinked hydrogel polymer (hereinafter referred to as "hydrogel") (1) was taken out. This series of operations were carried out in an atmospheric air open system. The polymerization had a peak temperature of 109° C.

The hydrogel (1) prepared through the above polymerization reaction was subjected to gel-crushing with use of a meat chopper (HL-3225N; plate pore diameter: 10.0 mm; available from Remacom Co., Ltd.) for preparation of a particulate hydrogel (1).

The above hydrogel (1) was introduced in an amount of 230 g/min. The gel-crushing was carried out while deionized water having a temperature adjusted to 90° C. was being added in an amount of 50 g/min simultaneously with the introduction of the hydrogel (1). In Production Example 1, the gel-grinding energy 2 (GGE2) was 3 J/g, D50 (weight average particle diameter) of the particulate hydrogel (1) was 1950 μm, and σζ (logarithmic standard deviation of a particle size distribution) was 2.43.

The particulate hydrogel (1) prepared through the above operation was spread on a stainless-steel metal gauze having a mesh size of 850 μm, and was dried by letting through 180° C. hot air for 30 minutes. Subsequently, the dry polymer (1) prepared through the drying operation was crushed with use of a roll mill (WML-type roll crusher; available from Inoguchi Giken Ltd.), and was then classified with use of JIS standard sieves having respective mesh sizes of 710 μm and 45 μm.

The above series of operations produced water-absorbing resin powder (1) ground to have uneven shapes. Table 1 shows physical properties of the water-absorbing resin powder (1) produced.

Production Example 2

Operations similar to those of Production Example 1 were carried out except that before 17.6 g of a 4.0 weight % aqueous sodium persulfate solution was added to the aqueous monomer solution (a) being stirred, nitrogen gas was introduced into the aqueous monomer solution (a) at 0.1 L/min for 5 seconds with use of a Kinoshita glass ball filter (filter particle No. 4; available from Kinoshita Rika Kogyo Co., Ltd.) and that the plate pore diameter of the meat chopper used for gel-crushing was changed from 10.0 mm to 8.0 mm. The operations produced water-absorbing resin powder (2) ground to have uneven shapes. Table 1 shows physical properties of the water-absorbing resin powder (2) produced.

In Production Example 2, 57 seconds after the aqueous monomer solution was poured into the butt vessel, a polymerization reaction started. The polymerization had a peak temperature of 110° C. The gel-grinding energy 2 (GGE2) was 9 J/g, D50 (weight average particle diameter) of the particulate hydrogel (2) was 900 μm, and σζ (logarithmic standard deviation of a particle size distribution) was 1.10.

Production Example 3

Operations similar to those of Production Example 2 were carried out except that the amount of deionized water (ion-exchange water) was changed from 394.7 g to 390.3 g and that 4.4 g of a 1.0 weight % aqueous polyoxyethylene (20) sorbitane monostearate (available from Kao Corporation) solution was added before the second-stage neutralization. The operations produced water-absorbing resin powder (3) ground to have uneven shapes. Table 1 shows physical properties of the water-absorbing resin powder (3) produced.

In Production Example 3, the temperature of the aqueous monomer solution rose to 62.9° C. due to heat of neutralization at the first stage and to 81.7° C. due to heat of neutralization at the second stage. Further, 60 seconds after the aqueous monomer solution was poured into the butt vessel, a polymerization reaction started. The polymerization had a peak temperature of 108° C. The gel-grinding energy 2 (GGE2) was 15 J/g, D50 (weight average particle diameter) of the particulate hydrogel (3) was 780 μm, and σζ (logarithmic standard deviation of a particle size distribution) was 1.02.

Production Example 4

Operations similar to those of Production Example 3 were carried out except that the plate pore diameter of the meat chopper used for gel-crushing was changed from 8.0 mm to 6.0 mm. The operations produced water-absorbing resin powder (4) ground to have uneven shapes. Table 1 shows physical properties of the water-absorbing resin powder (4) produced.

In Production Example 4, the gel-grinding energy 2 (GGE2) was 17 J/g, D50 (weight average particle diameter) of the particulate hydrogel (4) was 600 μm, and σζ (logarithmic standard deviation of a particle size distribution) was 0.73.

Production Example 5

Operations similar to those of Production Example 4 were carried out except that the time length of the nitrogen gas introduction was changed from 5 seconds to 10 seconds. The operations produced water-absorbing resin powder (5) ground to have uneven shapes. Table 1 shows physical properties of the water-absorbing resin powder (5) produced.

In Production Example 5, 59 seconds after the aqueous monomer solution was poured into the butt vessel, a polymerization reaction started. The polymerization had a peak temperature of 112° C. The gel-grinding energy 2 (GGE2) was 23 J/g, D50 (weight average particle diameter) of the particulate hydrogel (5) was 350 μm, and of (logarithmic standard deviation of a particle size distribution) was 0.93.

Production Example 5-1

Operations similar to those of Production Example 1 were carried out except that 5.2 g of a 10.0 weight % aqueous polyoxyethylene (20) sorbitane monostearate (available from Kao Corporation) solution was added before the second-stage neutralization, that 17.6 g of a 4.0 weight % aqueous sodium persulfate solution was replaced with 12.5 g of a 5.6 weight % aqueous sodium persulfate solution, and that the plate pore diameter of the meat chopper used for gel-crushing was changed from 10.0 mm to 8.0 mm. The operations produced water-absorbing resin powder (5-1) ground to have uneven shapes. Table 1 shows physical properties of the water-absorbing resin powder (5-1) produced.

In Production Example 5-1, 68 seconds after the aqueous monomer solution was poured into the butt vessel, a polymerization reaction started. The polymerization had a peak temperature of 110° C. The gel-grinding energy 2 (GGE2) was 25 J/g, D50 (weight average particle diameter) of the particulate hydrogel (5-1) was 380 μm, and σζ (logarithmic standard deviation of a particle size distribution) was 0.86.

Production Example 5-2

Operations similar to those of Production Example 1 were carried out except that before 17.6 g of a 4.0 weight % aqueous sodium persulfate solution was added to the aqueous monomer solution (a) being stirred, 5.2 g of sodium bicarbonate (available from Wako Pure Chemical Industries, Ltd.) was added as a foaming agent and that the plate pore diameter of the meat chopper used for gel-crushing was changed from 10.0 mm to 6.0 mm. The operations produced water-absorbing resin powder (5-2) ground to have uneven shapes. Table 1 shows physical properties of the water-absorbing resin powder (5-2) produced.

In Production Example 5-2, 61 seconds after the aqueous monomer solution was poured into the butt vessel, a polymerization reaction started. The polymerization had a peak temperature of 107° C. The gel-grinding energy 2 (GGE2) was 15 J/g, D50 (weight average particle diameter) of the particulate hydrogel (5-2) was 830 μm, and σζ (logarithmic standard deviation of a particle size distribution) was 1.07.

Production Example 6

Operations similar to those of Production Example 1 were carried out except that the amount of polyethyleneglycol diacrylate (molecular weight: 523) was changed from 2.4 g to 1.8 g and that the amount of deionized water (ion-exchange water) was changed from 394.7 g to 395.3 g. The operations produced water-absorbing resin powder (6) ground to have uneven shapes. Table 1 shows physical properties of the water-absorbing resin powder (6) produced.

In Production Example 6, the temperature of the aqueous monomer solution rose to 61.3° C. due to heat of neutralization at the first stage and to 81.0° C. due to heat of neutralization at the second stage. Further, 56 seconds after the aqueous monomer solution was poured into the butt vessel, a polymerization reaction started. The polymerization had a peak temperature of 110° C. The gel-grinding energy 2 (GGE2) was 14 J/g, D50 (weight average particle diameter) of the particulate hydrogel (6) was 1800 μm, and σζ (logarithmic standard deviation of a particle size distribution) was 2.05.

Production Example 7

Operations similar to those of Production Example 6 were carried out except that the plate pore diameter of the meat chopper used for gel-crushing was changed from 10.0 mm to 8.0 mm. The operations produced water-absorbing resin powder (7) ground to have uneven shapes. Table 1 shows physical properties of the water-absorbing resin powder (7) produced.

In Production Example 7, the gel-grinding energy 2 (GGE2) was 18 J/g, D50 (weight average particle diameter) of the particulate hydrogel (7) was 1300 μm, and σζ (logarithmic standard deviation of a particle size distribution) was 1.17.

Production Example 8

Operations similar to those of Production Example 2 were carried out except that the JIS standard sieves having respective mesh sizes of 710 μm and 45 μm were replaced with JIS standard sieves having respective mesh sizes of 850 μm and 45 μm for classification. The operations produced water-absorbing resin powder (8) ground to have uneven shapes. Table 1 shows physical properties of the water-absorbing resin powder (8) produced.

TABLE 1

|  | Water-absorbing resin powder produced | Physical properties of water-absorbing resin powder | | | |
|---|---|---|---|---|---|
|  |  | Solid content [wt %] | D50 [μm] | σζ | BET specific surface area [m²/g] |
| Production Example 1 | Water-absorbing resin powder (1) | 96.0 | 435 | 0.39 | 0.0203 |
| Production Example 2 | Water-absorbing resin powder (2) | 96.0 | 421 | 0.37 | 0.0277 |
| Production Example 3 | Water-absorbing resin powder (3) | 96.2 | 403 | 0.39 | 0.0302 |
| Production Example 4 | Water-absorbing resin powder (4) | 96.5 | 427 | 0.38 | 0.0307 |
| Production Example 5 | Water-absorbing resin powder (5) | 96.6 | 440 | 0.37 | 0.0330 |
| Production Example 5-1 | Water-absorbing resin powder (5-1) | 96.5 | 431 | 0.39 | 0.0316 |
| Production Example 5-2 | Water-absorbing resin powder (5-2) | 96.3 | 419 | 0.37 | 0.0282 |
| Production Example 6 | Water-absorbing resin powder (6) | 95.7 | 392 | 0.42 | 0.0216 |
| Production Example 7 | Water-absorbing resin powder (7) | 95.8 | 405 | 0.40 | 0.0268 |
| Production Example 8 | Water-absorbing resin powder (8) | 96.0 | 450 | 0.45 | 0.0267 |

Comparative Example 1

To 100 parts by weight of the water-absorbing resin powder (1) produced in Production Example 1 above, a surface-crosslinking agent solution (1) containing 0.3 parts by weight of ethylene carbonate, 0.6 parts by weight of propylene glycol, 3.0 parts by weight of deionized water (ion-exchange water), and 0.001 parts by weight (10 ppm with respect to the water-absorbing resin powder (1)) of polyoxyethylene (20) sorbitane monostearate (available from Kao Corporation) was added, and was mixed therewith uniformly. Subsequently, the mixture was heat-treated at 208° C. for 40 minutes for surface-crosslinking.

After the heat treatment, the resulting comparative water-absorbing resin particles (1) were crushed until they passed through a JIS standard sieve having a mesh size of 850 μm. This prepared a comparative water-absorbing agent (1). Table 2 shows physical properties of the comparative water-absorbing agent (1) produced.

Example 1

Operations similar to those of Comparative Example 1 were carried out except that the water-absorbing resin powder (1) was replaced with the water-absorbing resin powder (2) produced in Production Example 2. The operations produced a water-absorbing agent (1). Table 2 shows physical properties of the water-absorbing agent (1) produced.

Example 2

Operations similar to those of Comparative Example 1 were carried out except that the water-absorbing resin powder (1) was replaced with the water-absorbing resin powder (3) produced in Production Example 3. The operations produced a water-absorbing agent (2). Table 2 shows physical properties of the water-absorbing agent (2) produced.

Example 3

Operations similar to those of Comparative Example 1 were carried out except that the water-absorbing resin powder (1) was replaced with the water-absorbing resin powder (4) produced in Production Example 4. The operations produced a water-absorbing agent (3). Table 2 shows physical properties of the water-absorbing agent (3) produced.

Example 4

Operations similar to those of Comparative Example 1 were carried out except that the water-absorbing resin powder (1) was replaced with the water-absorbing resin powder (5) produced in Production Example 5. The operations produced a water-absorbing agent (4). Table 2 shows physical properties of the water-absorbing agent (4) produced.

Example 4-1

Operations similar to those of Comparative Example 1 were carried out except that the water-absorbing resin powder (1) was replaced with the water-absorbing resin powder (5-1) produced in Production Example 5-1. The operations produced a water-absorbing agent (4-1). Table 2 shows physical properties of the water-absorbing agent (4-1) produced.

Example 4-2

Operations similar to those of Comparative Example 1 were carried out except that the water-absorbing resin powder (1) was replaced with the water-absorbing resin powder (5-2) produced in Production Example 5-2. The operations produced a water-absorbing agent (4-2). Table 2 shows physical properties of the water-absorbing agent (4-2) produced.

Comparative Example 2

To 100 parts by weight of the water-absorbing resin powder (6) produced in Production Example 6 above, a surface-crosslinking agent solution (2) containing 0.4 parts by weight of ethylene carbonate, 0.6 parts by weight of propylene glycol, and 2.5 parts by weight of deionized water (ion-exchange water) was added, and was mixed therewith uniformly. Subsequently, the mixture was heat-treated at 205° C. for 40 minutes for surface-crosslinking.

After the heat treatment, the resulting comparative water-absorbing resin particles (2) were crushed until they passed through a JIS standard sieve having a mesh size of 850 μm. This prepared a comparative water-absorbing agent (2). Table 2 shows physical properties of the comparative water-absorbing agent (2) produced.

Comparative Example 3

Operations similar to those of Comparative Example 2 were carried out except that the water-absorbing resin powder (6) was replaced with the water-absorbing resin powder (7) produced in Production Example 7. The operations produced a comparative water-absorbing agent (3). Table 2 shows physical properties of the comparative water-absorbing agent (3) produced.

Comparative Example 4

Operations similar to those of Comparative Example 1 were carried out except that the water-absorbing resin powder (1) was replaced with the water-absorbing resin powder (8) produced in Production Example 8. The operations produced a comparative water-absorbing agent (4). Table 2 shows physical properties of the comparative water-absorbing agent (4) produced.

In Tables 2 to 6 below, "150-710 μm particle proportion" refers to the proportion of particles each having a diameter of not less than 150 μm and less than 710 μm.

TABLE 2

| | Water-absorbing agent produced | CRC [g/g] | AAP [g/g] | SFC [×10$^{-7}$ · cm$^3$ · s · g$^{-1}$] | FSR [g/g/s] | D50 [μm] | σζ | 150-710 μm particle proportion [%] | Gap fluid retention property under pressure [g/g] | Re-wet under pressure [g] | Wet porosity [%] |
|---|---|---|---|---|---|---|---|---|---|---|---|
| Comparative Example 1 | Comparative water-absorbing agent (1) | 26.5 | 23.7 | 80 | 0.19 | 439 | 0.42 | 98.2 | 7.2 | 4.73 | 26.7 |
| Example 1 | Water-absorbing agent (1) | 27.0 | 24.9 | 80 | 0.33 | 440 | 0.39 | 98.0 | 10.2 | 1.46 | 28.4 |
| Example 2 | Water-absorbing agent (2) | 27.7 | 25.2 | 66 | 0.37 | 414 | 0.39 | 97.7 | 10.0 | 1.89 | 28.0 |

TABLE 2-continued

Physical properties of water-absorbing agent

|  | Water-absorbing agent produced | CRC [g/g] | AAP [g/g] | SFC [×10⁻⁷ · cm³ · s · g⁻¹] | FSR [g/g/s] | D50 [μm] | σζ | 150-710 μm particle proportion [%] | Gap fluid retention property under pressure [g/g] | Re-wet under pressure [g] | Wet porosity [%] |
|---|---|---|---|---|---|---|---|---|---|---|---|
| Example 3 | Water-absorbing agent (3) | 27.4 | 25.0 | 70 | 0.38 | 449 | 0.41 | 98.0 | 10.9 | 1.52 | 28.7 |
| Example 4 | Water-absorbing agent (4) | 27.0 | 24.4 | 77 | 0.41 | 438 | 0.40 | 97.4 | 11.0 | 0.51 | 28.5 |
| Example 4-1 | Water-absorbing agent (4-1) | 26.9 | 24.8 | 80 | 0.40 | 404 | 0.42 | 97.6 | 11.1 | 0.63 | 28.6 |
| Example 4-2 | Water-absorbing agent (4-2) | 27.5 | 24.5 | 71 | 0.33 | 428 | 0.40 | 97.9 | 10.1 | 1.67 | 28.2 |
| Comparative Example 2 | Comparative water-absorbing agent (2) | 29.5 | 24.9 | 45 | 0.20 | 413 | 0.45 | 97.9 | 7.8 | 4.67 | 27.0 |
| Comparative Example 3 | Comparative water-absorbing agent (3) | 28.7 | 24.9 | 47 | 0.28 | 425 | 0.42 | 97.7 | 8.6 | 3.48 | 27.9 |
| Comparative Example 4 | Comparative water-absorbing agent (4) | 27.5 | 25.1 | 89 | 0.32 | 463 | 0.49 | 85.7 | 8.9 | 3.43 | 27.7 |

Comparative Example 5

A mixed solution (5) was prepared that contained: 0.91 parts by weight of a 27 weight % aqueous aluminum sulfate solution (8 weight % based on aluminum oxide), the aluminum sulfate being a compound for use as a raw material of a polyvalent metal cation; 0.27 parts by weight of a 60 weight % aqueous sodium lactate solution; and 0.02 parts by weight of propylene glycol.

To 100 parts by weight of the comparative water-absorbing agent (1) produced in Comparative Example 1, 1.2 parts by weight of the above mixed solution (5) was added while being stirred, and was uniformly mixed for 1 minute. Subsequently, the mixture was dried windlessly at 60° C. for 30 minutes, and was then passed through a JIS standard sieve having a mesh size of 850 μm. This prepared a comparative water-absorbing agent (5). Table 3 shows physical properties of the comparative water-absorbing agent (5) produced.

Comparative Example 6

Operations similar to those of Comparative Example 5 were carried out except that the comparative water-absorbing agent (1) was replaced with the water-absorbing agent (1) produced in Example 1. The operations produced a comparative water-absorbing agent (6). Table 3 shows physical properties of the comparative water-absorbing agent (6) produced.

Comparative Example 7

Operations similar to those of Comparative Example 5 were carried out except that the comparative water-absorbing agent (1) was replaced with the water-absorbing agent (2) produced in Example 2. The operations produced a comparative water-absorbing agent (7). Table 3 shows physical properties of the comparative water-absorbing agent (7) produced.

Comparative Example 8

Operations similar to those of Comparative Example 5 were carried out except that the comparative water-absorbing agent (1) was replaced with the water-absorbing agent (3) produced in Example 3. The operations produced a comparative water-absorbing agent (8). Table 3 shows physical properties of the comparative water-absorbing agent (8) produced.

Example 5

Operations similar to those of Comparative Example 5 were carried out except that the comparative water-absorbing agent (1) was replaced with the water-absorbing agent (4) produced in Example 4. The operations produced a water-absorbing agent (5). Table 3 shows physical properties of the water-absorbing agent (5) produced.

Example 5-1

Operations similar to those of Comparative Example 5 were carried out except that the comparative water-absorbing agent (1) was replaced with the water-absorbing agent (4-1) produced in Example 4-1. The operations produced a water-absorbing agent (5-1). Table 3 shows physical properties of the water-absorbing agent (5-1) produced.

Comparative Example 8-1

Operations similar to those of Comparative Example 5 were carried out except that the comparative water-absorbing agent (1) was replaced with the water-absorbing agent (4-2) produced in Example 4-2. The operations produced a comparative water-absorbing agent (8-1). Table 3 shows physical properties of the comparative water-absorbing agent (8-1) produced.

Comparative Example 9

Operations similar to those of Comparative Example 5 were carried out except that the comparative water-absorbing agent (1) was replaced with the comparative water-absorbing agent (2) produced in Comparative Example 2. The operations produced a comparative water-absorbing agent (9). Table 3 shows physical properties of the comparative water-absorbing agent (9) produced.

Comparative Example 10

Operations similar to those of Comparative Example 5 were carried out except that the comparative water-absorbing agent (1) was replaced with the comparative water-absorbing agent (3) produced in Comparative Example 3. The operations produced a comparative water-absorbing agent (10). Table 3 shows physical properties of the comparative water-absorbing agent (10) produced.

Example 6

Operations similar to those of Comparative Example 6 were carried out except that the amount of the mixed solution (5) was changed from 1.2 parts by weight to 0.3 parts by weight. The operations produced a water-absorbing agent (6). Table 3 shows physical properties of the water-absorbing agent (6) produced.

Example 7

Operations similar to those of Comparative Example 6 were carried out except that the amount of the mixed solution (5) was changed from 1.2 parts by weight to 0.8 parts by weight. The operations produced a water-absorbing agent (7). Table 3 shows physical properties of the water-absorbing agent (7) produced.

Comparative Example 11

Operations similar to those of Comparative Example 6 were carried out except that the amount of the mixed solution (5) was changed from 1.2 parts by weight to 2.0 parts by weight. The operations produced a comparative water-absorbing agent (11). Table 3 shows physical properties of the comparative water-absorbing agent (11) produced.

Comparative Example 12

Operations similar to those of Example 5 were carried out except that the amount of the mixed solution (5) was changed from 1.2 parts by weight to 3.0 parts by weight. The operations produced a comparative water-absorbing agent (12). Table 3 shows physical properties of the comparative water-absorbing agent (12) produced.

In Table 3, each value under "[$\times 10^{-5} \cdot$mol/g]" as a unit of the amount of a liquid permeability improving agent added refers to the amount of polyvalent metal atoms added per 1 g of water-absorbing resin powder.

TABLE 3

|  |  | Liquid permeability improving agent | | | Physical properties of water-absorbing agent | | |
| --- | --- | --- | --- | --- | --- | --- | --- |
|  |  |  | Amount added | | | | SFC |
|  | Water-absorbing agent used | Type | [parts by weight] | [$\times 10^{-5} \cdot$ mol/g] | CRC [g/g] | AAP [g/g] | [$\times 10^{-7} \cdot$ cm$^3 \cdot$ s $\cdot$ g$^{-1}$] |
| Comparative Example 5 | Comparative water-absorbing agent (1) | Mixed solution (5) | 1.2 | 1.44 | 26.6 | 23.3 | 109 |
| Comparative Example 6 | Water-absorbing agent (1) | Mixed solution (5) | 1.2 | 1.44 | 27.0 | 24.3 | 110 |
| Comparative Example 7 | Water-absorbing agent (2) | Mixed solution (5) | 1.2 | 1.44 | 26.8 | 24.0 | 109 |
| Comparative Example 8 | Water-absorbing agent (3) | Mixed solution (5) | 1.2 | 1.44 | 26.3 | 23.8 | 118 |
| Example 5 | Water-absorbing agent (4) | Mixed solution (5) | 1.2 | 1.44 | 26.9 | 24.0 | 104 |
| Example 5-1 | Water-absorbing agent (4-1) | Mixed solution (5) | 1.2 | 1.44 | 26.5 | 24.2 | 125 |
| Comparative Example 8-1 | Water-absorbing agent (4-2) | Mixed solution (5) | 1.2 | 1.44 | 27.0 | 24.0 | 108 |
| Comparative Example 9 | Comparative water-absorbing agent (2) | Mixed solution (5) | 1.2 | 1.44 | 29.6 | 24.3 | 66 |
| Comparative Example 10 | Comparative water-absorbing agent (3) | Mixed solution (5) | 1.2 | 1.44 | 28.5 | 24.2 | 65 |
| Example 6 | Water-absorbing agent (1) | Mixed solution (5) | 0.3 | 0.36 | 27.1 | 24.6 | 75 |
| Example 7 | Water-absorbing agent (1) | Mixed solution (5) | 0.8 | 0.96 | 26.9 | 24.3 | 96 |
| Comparative Example 11 | Water-absorbing agent (1) | Mixed solution (5) | 2.0 | 2.40 | 26.6 | 23.6 | 104 |
| Comparative Example 12 | Water-absorbing agent (4) | Mixed solution (5) | 3.0 | 3.60 | 26.3 | 23.0 | 100 |

TABLE 3-continued

| | | | | | Physical properties of water-absorbing agent | | |
|---|---|---|---|---|---|---|---|
| | | FSR [g/g/s] | D50 [μm] | σζ | 150-710 μm particle proportion [%] | Gap fluid retention property under pressure [g/g] | Re-wet under pressure [g] | Wet porosity [%] |
| Comparative Example 5 | 0.27 | 430 | 0.37 | 99.1 | 7.0 | 4.89 | 27.5 |
| Comparative Example 6 | 0.35 | 417 | 0.37 | 99.0 | 8.6 | 3.75 | 30.0 |
| Comparative Example 7 | 0.38 | 398 | 0.40 | 98.9 | 8.4 | 3.35 | 29.9 |
| Comparative Example 8 | 0.37 | 419 | 0.38 | 99.3 | 8.9 | 3.02 | 29.3 |
| Example 5 | 0.42 | 438 | 0.36 | 98.7 | 9.2 | 2.74 | 30.3 |
| Example 5-1 | 0.40 | 415 | 0.37 | 98.9 | 9.2 | 2.99 | 29.8 |
| Comparative Example 8-1 | 0.36 | 420 | 0.39 | 99.1 | 8.0 | 3.86 | 29.3 |
| Comparative Example 9 | 0.21 | 398 | 0.44 | 98.9 | 7.0 | 4.74 | 28.2 |
| Comparative Example 10 | 0.31 | 401 | 0.40 | 98.5 | 8.0 | 4.20 | 29.8 |
| Example 6 | 0.36 | 425 | 0.39 | 99.3 | 9.7 | 2.82 | 30.7 |
| Example 7 | 0.37 | 405 | 0.36 | 99.0 | 9.4 | 2.76 | 30.3 |
| Comparative Example 11 | 0.36 | 400 | 0.36 | 98.8 | 8.5 | 3.32 | 29.1 |
| Comparative Example 12 | 0.43 | 403 | 0.38 | 98.5 | 8.9 | 3.11 | 30.1 |

Example 8

UNISENCE KHE102L (dimethylamine-ammonium-epichlorohydrin resin; average molecular weight: approximately 70,000 (reference); 50 weight % aqueous solution; available from SENKA Corporation) and methanol were mixed with each other for preparation of a 50 weight % methanol solution (8) (solid content: 25 weight %).

Operations similar to those of Comparative Example 6 were carried out except that 1.2 parts by weight of the mixed solution (5) was replaced with 1.0 part by weight of the methanol solution (8). The operations produced a water-absorbing agent (8). Table 4 shows physical properties of the water-absorbing agent (8) produced.

Example 9

Operations similar to those of Example 8 were carried out except that the amount of the methanol solution (8) was changed from 1.0 part by weight to 4.0 parts by weight. The operations produced a water-absorbing agent (9). Table 4 shows physical properties of the water-absorbing agent (9) produced.

Comparative Example 13

Operations similar to those of Example 8 were carried out except that the amount of the methanol solution (8) was changed from 1.0 part by weight to 8.0 parts by weight. The operations produced a comparative water-absorbing agent (13). Table 4 shows physical properties of the comparative water-absorbing agent (13) produced.

Example 10

Operations similar to those of Example 5 were carried out except that 1.2 parts by weight of the mixed solution (5) was replaced with 4.0 parts by weight of the methanol solution (8). The operations produced a water-absorbing agent (10). Table 4 shows physical properties of the water-absorbing agent (10) produced.

Example 11

Operations similar to those of Example 10 were carried out except that the amount of the methanol solution (8) was changed from 4.0 parts by weight to 8.0 parts by weight. The operations produced a water-absorbing agent (11). Table 4 shows physical properties of the water-absorbing agent (11) produced.

Comparative Example 14

Operations similar to those of Example 10 were carried out except that the amount of the methanol solution (8) was changed from 4.0 parts by weight to 10.0 parts by weight. The operations produced a comparative water-absorbing agent (14). Table 4 shows physical properties of the comparative water-absorbing agent (14) produced.

Example 12

With 100 parts by weight of the water-absorbing agent (1) produced in Example 1 above, 0.1 parts by weight of Reolosil QS-20 (dry silica; primary particle diameter: 12 nm; available from Tokuyama Corporation) was mixed. This mixing was carried out by putting the sample in a 225-ml mayonnaise bottle and shaking the bottle at room temperature for 3 minutes with use of a paint shaker (available from Toyo Seiki Seisaku-sho, Ltd.). The above series of operations produced a water-absorbing agent (12). Table 4 shows physical properties of the water-absorbing agent (12) produced.

Comparative Example 15

Operations similar to those of Example 12 were carried out except that the amount of Reolosil QS-20 was changed from 0.1 parts by weight to 0.3 parts by weight. The operations produced a comparative water-absorbing agent (15). Table 4 shows physical properties of the comparative water-absorbing agent (15) produced.

Example 13

With 100 parts by weight of the water-absorbing agent (4) produced in Example 4 above, 0.8 parts by weight of the above Reolosil QS-20 (dry silica; primary particle diameter: 12 nm; available from Tokuyama Corporation) was mixed. This mixing was carried out by putting the sample in a 225-ml mayonnaise bottle and shaking the bottle at room temperature for 3 minutes with use of a paint shaker (available from Toyo Seiki Seisaku-sho, Ltd.). The above series of operations produced a water-absorbing agent (13). Table 4 shows physical properties of the water-absorbing agent (13) produced.

Comparative Example 16

Operations similar to those of Example 13 were carried out except that the amount of Reolosil QS-20 was changed from 0.8 parts by weight to 1.2 parts by weight. The operations produced a comparative water-absorbing agent (16). Table 4 shows physical properties of the comparative water-absorbing agent (16) produced.

Example 14

With 100 parts by weight of the water-absorbing agent (1) produced in Example 1 above, 0.3 parts by weight of AEROSIL OX 50 (hydrophilic fumed silica; primary particle diameter: 40 nm; available from Nippon Aerosil Co., Ltd.) was mixed. This mixing was carried out by putting the sample in a 225-ml mayonnaise bottle and shaking the bottle at room temperature for 3 minutes with use of a paint shaker (available from Toyo Seiki Seisaku-sho, Ltd.). The above series of operations produced a water-absorbing agent (14). Table 4 shows physical properties of the water-absorbing agent (14) produced.

Comparative Example 17

Operations similar to those of Example 14 were carried out except that the amount of AEROSIL OX 50 was changed from 0.3 parts by weight to 1.0 part by weight. The operations produced a comparative water-absorbing agent (17). Table 4 shows physical properties of the comparative water-absorbing agent (17) produced.

Example 15

With 100 parts by weight of the water-absorbing agent (4) produced in Example 4 above, 1.0 part by weight of AEROSIL OX 50 (hydrophilic fumed silica; primary particle diameter: 40 nm; available from Nippon Aerosil Co., Ltd.) was mixed. This mixing was carried out by shaking at room temperature for 3 minutes with use of a paint shaker (available from Toyo Seiki Seisaku-sho, Ltd. The above series of operations produced a water-absorbing agent (15). Table 4 shows physical properties of the water-absorbing agent (15) produced.

Comparative Example 18

Operations similar to those of Example 15 were carried out except that the amount of AEROSIL OX 50 was changed from 1.0 part by weight to 2.0 parts by weight. The operations produced a comparative water-absorbing agent (18). Table 4 shows physical properties of the comparative water-absorbing agent (18) produced.

In Table 4, the item "Solid content addition amount" refers to the amount of a liquid permeability improving agent added with respect to the solid content of water-absorbing resin powder.

TABLE 4

| | | Liquid permeability improving agent | | Physical properties of water-absorbing agent | | | |
|---|---|---|---|---|---|---|---|
| | Water-absorbing agent used | Type | Solid content Amount added [parts by weight] | CRC [g/g] | AAP [g/g] | SFC [×10$^{-7}$ · cm$^3$ · s · g$^{-1}$] | FSR [g/g/s] |
| Example 8 | Water-absorbing agent (1) | UNISENCE KHE102L (solid content: 25 [wt %]) | 0.3 | 27.0 | 22.9 | 96 | 0.41 |
| Example 9 | Water-absorbing agent (1) | UNISENCE KHE102L (solid content: 25 [wt %]) | 1.0 | 26.8 | 21.9 | 117 | 0.42 |
| Comparative Example 13 | Water-absorbing agent (1) | UNISENCE KHE102L (solid content: 25 [wt %]) | 2.0 | 26.4 | 21.4 | 131 | 0.39 |
| Example 10 | Water-absorbing agent (4) | UNISENCE KHE102L (solid content: 25 [wt %]) | 1.0 | 26.6 | 21.8 | 120 | 0.48 |
| Example 11 | Water-absorbing agent (4) | UNISENCE KHE102L (solid content: 25 [wt %]) | 2.0 | 26.3 | 21.6 | 138 | 0.47 |
| Comparative Example 14 | Water-absorbing agent (4) | UNISENCE KHE102L (solid content: 25 [wt %]) | 2.5 | 26.2 | 21.3 | 139 | 0.45 |

TABLE 4-continued

| | | | | | | | |
|---|---|---|---|---|---|---|---|
| Example 12 | Water-absorbing agent (1) | Reolosil QS-20 | 0.1 | 27.4 | 22.9 | 83 | 0.36 |
| Comparative Example 15 | Water-absorbing agent (1) | Reolosil QS-20 | 0.3 | 26.8 | 21.9 | 94 | 0.40 |
| Example 13 | Water-absorbing agent (4) | Reolosil QS-20 | 0.8 | 26.6 | 21.6 | 91 | 0.45 |
| Comparative Example 16 | Water-absorbing agent (4) | Reolosil QS-20 | 1.2 | 26.4 | 21.4 | 93 | 0.47 |
| Example 14 | Water-absorbing agent (1) | AEROSIL OX 50 | 0.3 | 27.0 | 23.7 | 74 | 0.35 |
| Comparative Example 17 | Water-absorbing agent (1) | AEROSIL OX 50 | 1.0 | 26.7 | 23.4 | 80 | 0.37 |
| Example 15 | Water-absorbing agent (4) | AEROSIL OX 50 | 1.0 | 26.8 | 23.2 | 78 | 0.44 |
| Comparative Example 18 | Water-absorbing agent (4) | AEROSIL OX 50 | 2.0 | 26.3 | 22.8 | 80 | 0.46 |

| | Physical properties of water-absorbing agent | | | | | |
|---|---|---|---|---|---|---|
| | D50 [μm] | σζ | 150-710 μm particle proportion [%] | Gap fluid retention property under pressure [g/g] | Re-wet under pressure [g] | Wet porosity [%] |
| Example 8 | 428 | 0.36 | 99.4 | 9.8 | 2.81 | 28.9 |
| Example 9 | 431 | 0.38 | 99.2 | 9.6 | 2.71 | 28.9 |
| Comparative Example 13 | 435 | 0.40 | 99.0 | 7.7 | 3.87 | 28.4 |
| Example 10 | 420 | 0.37 | 98.6 | 10.1 | 2.45 | 29.1 |
| Example 11 | 433 | 0.39 | 98.5 | 9.8 | 2.60 | 28.7 |
| Comparative Example 14 | 442 | 0.42 | 99.0 | 8.9 | 2.99 | 28.3 |
| Example 12 | 410 | 0.38 | 98.7 | 9.5 | 2.78 | 29.0 |
| Comparative Example 15 | 405 | 0.36 | 98.7 | 8.6 | 3.95 | 28.3 |
| Example 13 | 420 | 0.41 | 98.3 | 9.2 | 2.85 | 28.7 |
| Comparative Example 16 | 415 | 0.38 | 98.5 | 8.3 | 3.22 | 28.6 |
| Example 14 | 418 | 0.39 | 98.5 | 9.2 | 2.23 | 29.3 |
| Comparative Example 17 | 425 | 0.39 | 93.3 | 8.9 | 2.99 | 28.9 |
| Example 15 | 429 | 0.40 | 98.2 | 10.1 | 2.48 | 29.5 |
| Comparative Example 18 | 417 | 0.38 | 98.2 | 8.8 | 3.02 | 28.5 |

Comparative Example 19

A comparative water-absorbing agent (19) was prepared as in Example 2 of Patent Literature 11 above (International Publication No. 2011/126079). Table 5 shows physical properties of the comparative water-absorbing agent (19) produced.

In Comparative Example 19, the gel-grinding energy 2 (GGE2) was 14 J/g, D50 (weight average particle diameter) of the particulate comparative hydrogel (19) was 820 μm, and σζ (logarithmic standard deviation of a particle size distribution) was 0.83. Water-absorbing resin powder produced in Comparative Example 19 had a solid content of 96 weight %, D50 (weight average particle diameter) of 352 μm, σζ (logarithmic standard deviation of a particle size distribution) of 0.39, and a BET specific surface area of 0.0300 m²/g.

Comparative Examples 20 to 23

Disposable diapers commercially available in different countries were purchased, and a water-absorbing agent contained in each disposable diaper was taken out for analysis in order to determine the respective gap fluid retention properties under pressure of different water-absorbing resins commercially available at the time of the filing of the present application.

Specifically, water-absorbing agents were taken out from a disposable diaper purchased in the U.S. in June 2013 (product name: Luvs SUPER ABSORBENT LEAK-GUARDS; available from Procter & Gamble Co.), a disposable diaper purchased in Belgium in June 2013 (product name: Pampers Simply Dry; available from Procter & Gamble Co.), a disposable diaper purchased in Mexico in May 2013 (product name: KleenBebeAbsorSec; available from Kimberly-Clark Corp.), and a disposable diaper purchased in Thailand in November 2013 (product name: GOO.N Hajimete no Hadagi; available from Daio Paper Corporation) as comparative water-absorbing agents (20) to (23).

The CRC, AAP, SFC, FSR, particle size distribution, gap fluid retention property under pressure, and re-wet under pressure of each of the comparative water-absorbing agents (20) to (23) were measured. Table 5 shows the results.

Regarding each of the comparative water-absorbing agents (22) and (23), the gap fluid retention property under pressure could not be measured. The gap fluid retention property under pressure is typically measured in the following manner: A liquid flows down from a cylinder as an SFC instrument. Subsequently, the weight of the SFC instruments is measured at a time point at which no single drop has flown down from the cylinder over a period of 30 seconds (that is, a time point at which the hydrostatic height inside the cylinder has become equal to the height of a gel layer). The comparative water-absorbing agents (22) and (23) each had an extremely low liquid permeability, so that the hydrostatic height inside the cylinder hardly changed over a period of 30 minutes. This led to the determination that the gap fluid retention property under pressure could not be measured.

TABLE 5

| | CRC [g/g] | AAP [g/g] | SFC [×10⁻⁷ · cm³ · s · g⁻¹] | FSR [g/g/s] | D50 [μm] | σζ | 150-710 μm particle proportion [%] | Gap fluid retention property under pressure [g/g] | Re-wet under pressure [g] | Wet porosity [%] |
|---|---|---|---|---|---|---|---|---|---|---|
| Comparative Example 19 | 26.5 | 23.5 | 120 | 0.37 | 332 | 0.49 | 88.0 | 8.5 | 3.08 | 29.7 |
| Comparative Example 20 | 28.1 | 23.7 | 51 | 0.15 | 469 | 0.38 | 99.1 | 6.0 | 6.11 | 26.0 |
| Comparative Example 21 | 29.9 | 23.3 | 53 | 0.19 | 499 | 0.40 | 98.5 | 5.8 | 6.23 | 25.6 |
| Comparative Example 22 | 29.4 | 17.6 | 1 | 0.58 | 335 | 0.44 | 93.3 | Could not be measured | 6.60 | Could not be measured |
| Comparative Example 23 | 34.0 | 14.9 | 0 | 0.27 | 325 | 0.29 | 98.1 | Could not be measured | 6.47 | Could not be measured |

Production Example 9

Operations similar to those of Production Example 2 were carried out except that the plate pore diameter of the meat chopper used for gel-crushing was changed from 8.0 mm to 4.5 mm. The operations produced water-absorbing resin powder (9) ground to have uneven shapes. The water-absorbing resin powder (9) produced had a solid content of 96.3 wt %, D50 (weight average particle diameter) of 388 μm, σζ (logarithmic standard deviation of a particle size distribution) of 0.37, and a BET specific surface area of 0.0386 m²/g.

In Production Example 9, the gel-grinding energy 2 (GGE2) was 47 J/g, D50 (weight average particle diameter) of the particulate hydrogel (9) was 230 μm, and σζ (logarithmic standard deviation of a particle size distribution) was 1.05.

Example 16

Operations similar to those of Comparative Example 1 were carried out except that the water-absorbing resin powder (1) was replaced with the water-absorbing resin powder (9) produced in Production Example 9. The operations produced a water-absorbing agent (16). Table 6 shows physical properties of the water-absorbing agent (16) produced.

Example 17

Operations similar to those of Example 7 were carried out except that the water-absorbing agent (1) was replaced with the water-absorbing agent (16) produced in Example 16. The operations produced a water-absorbing agent (17). Table 6 shows physical properties of the water-absorbing agent (17) produced.

TABLE 6

| | CRC [g/g] | AAP [g/g] | SFC [×10⁻⁷ · cm³ · s · g⁻¹] | FSR [g/g/s] | D50 [μm] | σζ | 710-150 μm particle proportion [%] | Gap fluid retention property under pressure [g/g] | Re-wet under pressure [g] | Wet porosity [%] |
|---|---|---|---|---|---|---|---|---|---|---|
| Example 16 | 27.6 | 24.3 | 60 | 0.58 | 385 | 0.39 | 98.9 | 14.0 | 0.20 | 29.5 |
| Example 17 | 26.2 | 23.9 | 90 | 0.54 | 371 | 0.37 | 97.8 | 12.3 | 0.40 | 31.1 |

[Recap]

Tables 2 to 6 show that a method in accordance with the present invention for producing a water-absorbing agent allows production of an unconventional, well-balanced water-absorbing agent having a high liquid permeability (SFC) and an improved gap fluid retention property under pressure.

Comparative Example 1 and Examples 1 to 4 and 16 indicate that water-absorbing resin powder having a BET specific surface area of not less than 0.027 m$^2$/g allows production of a water-absorbing agent having an improved gap fluid retention property under pressure. Comparative Examples 2 and 3, on the other hand, indicate that even with an increased gel-grinding energy (2) (GGE (2)), water-absorbing resin powder having a BET specific surface area of less than 0.027 m$^2$/g results in production of a water-absorbing agent having a poor gap fluid retention property under pressure.

Examples 5 and 17 and Comparative Examples 5 to 10 indicate that while adding a liquid permeability improving agent degrades the gap fluid retention property under pressure, water-absorbing resin powder having a BET specific surface area of not less than 0.031 m$^2$/g allows production of a water-absorbing agent having a good gap fluid retention property under pressure.

A comparison between Example 1 and Comparative Example 4 shows that the gap fluid retention property under pressure is poor if the proportion of particles each having a particle diameter of not less than 150 μm and less than 710 μm is less than 90 weight %.

Examples 6 to 15 and Comparative Examples 11 to 18 indicate that controlling the BET specific surface area of water-absorbing resin powder and the type and amount of a liquid permeability improving agent to be added makes it possible to maintain a good gap fluid retention property under pressure.

In a case where water-absorbing resin powder has a small BET specific surface area, reducing the amount of a liquid permeability improving agent to be added allows the water-absorbing agent to have an improved gap fluid retention property under pressure. In a case where water-absorbing resin powder has a large BET specific surface area, increasing the amount of a liquid permeability improving agent to be added allows the water-absorbing agent to have an improved gap fluid retention property under pressure. The amount of a liquid permeability improving agent to be added is controlled so that the water-absorbing agent will maintain a small specific surface area in a case where the water-absorbing resin powder has a small specific surface area and that the water-absorbing agent will have an even larger specific surface area in a case where the water-absorbing resin powder has a large specific surface area. Although the specific surface area of the water-absorbing agent differs greatly, either of the above approaches can improve the gap fluid retention property under pressure. This is an unconventional method for adjusting the amount of a liquid permeability improving agent to be added.

Comparative Example 19 indicates that although conventional art allows for a high SFC, it results in a poor gap fluid retention property under pressure.

Comparative Examples 20 to 23 indicate that water-absorbing agents commercially available at the time of the filing of the present application (that is, water-absorbing resins taken out from commercially available disposable diapers) each had a gap fluid retention property under pressure which gap fluid retention property could not be measured or was not more than 6.0 g/g. In other words, no commercially available water-absorbing agent suggests that there is a water-absorbing resin having a gap fluid retention property under pressure of the present invention.

The following description will discuss how the gap fluid retention property under pressure is more correlated to the re-wet under pressure than the wet porosity is.

The values of the gap fluid retention property under pressure and re-wet under pressure in Tables 2 to 6 show that a better gap fluid retention property under pressure leads to a reduced re-wet under pressure. In other words, a water-absorbing agent of the present invention is capable of retaining a larger amount of liquid in the gap between particles even under pressure, and thus has a reduced re-wet under pressure.

Further, the values of the wet porosity and re-wet under pressure in Tables 2 and 3 show that these physical properties are not related to each other. In other words, while the re-wet under pressure is related to the gap fluid retention property under pressure, the re-wet under pressure is not related to the wet porosity. Also in a case where the measuring methods are compared with each other, the method for swelling a water-absorbing agent for measurement of the gap fluid retention property under pressure is close to the method for absorbing water for measurement of the re-wet under pressure. Measuring a gap fluid retention property under pressure involves introducing a large amount of absorption liquid onto a water-absorbing agent layer from above, whereas measuring a wet porosity involves letting a water-absorbing agent layer suck an absorption liquid from below for absorption. Different methods for absorbing an absorption liquid lead to different gel layers formed as a result of, for example, gel blocking. This should be a reason why the gap fluid retention property under pressure and the wet porosity are related differently to the re-wet under pressure. Assuming a case where a water-absorbing agent is actually included in a disposable diaper or the like, an absorption liquid will be introduced from above in a large amount. Thus, the method for measuring a gap fluid retention property under pressure should be more realistic in terms of practical use.

Measurement Example 1

Of each of the six types of water-absorbing agents, i.e., the water-absorbing agents (4), (6), and (16) and comparative water-absorbing agents (5), (13), and (15), produced in the corresponding Examples and Comparative Examples above, the gap fluid retention property under pressure was measured with variations in the salt concentration of a measurement solution used for measuring the gap fluid retention property under pressure. Table 7 shows the results.

Measurement Example 2

For each of the two types of water-absorbing agent, i.e., the water-absorbing agent (2) and comparative water-absorbing agent (6), produced in the corresponding Example and Comparative Example above, a model absorbent body was prepared, and the re-wet was measured. Table 8 shows the results.

TABLE 7

| Measurement solution salt concentration | | Gap fluid retention property under pressure [g/g] | | |
|---|---|---|---|---|
| | | 0.45 wt % | 0.69 wt % | 0.90 wt % |
| Example 16 | Water-absorbing agent (16) | 15.0 | 14.0 | 13.8 |
| Example 4 | Water-absorbing agent (4) | 13.2 | 11.0 | 10.8 |
| Example 6 | Water-absorbing agent (6) | 12.3 | 9.7 | 9.9 |
| Comparative Example 15 | Comparative water-absorbing agent (15) | 11.3 | 8.6 | 8.5 |
| Comparative Example 13 | Comparative water-absorbing agent (13) | 10.9 | 7.7 | 7.8 |
| Comparative Example 5 | Comparative water-absorbing agent (5) | 9.2 | 7.0 | 6.9 |

TABLE 8

| | | Re-wet of model absorbent body [g] |
|---|---|---|
| Example 2 | Water-absorbing agent (2) | 0.84 |
| Comparative Example 6 | Comparative water-absorbing agent (6) | 7.84 |

[Recap]

Table 7 shows that the use of a 0.45 weight % aqueous sodium chloride solution for measurement of the gap fluid retention property under pressure augmented the gap fluid retention property under pressure. During the measurement, a water-absorbing agent(s) had a gel layer with an extremely large thickness and had a height close to the hydrostatic height (5 cm) necessary for the measurement. The measurement could not be carried out stably in consequence. The 0.45 weight % aqueous sodium chloride solution was not suitable for measurement of the gap fluid retention property under pressure.

In contrast, the use of a 0.90 weight % aqueous sodium chloride solution for measurement of the gap fluid retention property under pressure resulted in a value substantially equal to that as measured with use of a 0.69 weight %/n aqueous sodium chloride solution. Thus, although the gap fluid retention property under pressure may be measured with use of a 0.90 weight % aqueous sodium chloride solution, it should preferably be measured with use of a 0.69 weight % aqueous sodium chloride solution from an economical viewpoint.

Table 8 shows that an improved gap fluid retention property under pressure results in a smaller re-wet for a model absorbent body as well.

INDUSTRIAL APPLICABILITY

Using a water-absorbing agent, produced in accordance with the present invention, for an absorbent body of an absorbent article such as a disposable diaper makes it possible to provide absorption performance in which re-wet under pressure is reduced, and which is superior in comparison to conventional absorbent articles.

REFERENCE SIGNS LIST

100 Glass tube having an open lower end
101 Rubber stopper section
102 Storage tank
103 Laboratory jack
104 Glass tube having a valve
105 Valve
106 Gap fluid retention property under pressure measuring instrument
107 Collection tank
108 Support
109 Flexible tube
110 Weight
111 Acrylic piston
112 Acrylic cover
113 Acrylic cylinder (cylinder (A))
114 Piston head
115 400-mesh wire mesh (stainless steel wire mesh)
116 Swollen water-absorbing agent
117 Liquid to be measured (aqueous medium (C))
500 Measuring device for measuring re-wet of a model absorbent body
501 Acrylic resin tray
502 Double-side tape
503 Water-absorbing sheet
504 Water-absorbing agent
505 Top sheet
506 Metal gauze
507 Inlet
508 Lid
509 Weight
510 Kitchen paper

The invention claimed is:

1. A water-absorbing agent comprising:
a polyacrylic acid (salt)-based water-absorbing resin as a main component, said water-absorbing agent satisfying (A) to (C) below:
(A) a saline flow conductivity (SFC) is not less than $20 \times 10^{-7} \cdot cm^3 \cdot s \cdot g^{-1}$;
(B) a gap fluid retention property under pressure is not less than 9 g/g; and
(C) a proportion of particles having a particle diameter of not less than 150 μm and less than 710 μm is not less than 90 weight %;
wherein, in (B), when a water-absorbing resin is swollen in a 0.69 weight % aqueous sodium chloride solution, said gap fluid retention property under pressure is a weight of the aqueous sodium chloride solution per gram of said water-absorbing agent, the sodium chloride solution being retained under a load of 2.07 kPa in gaps within said water-absorbing agent.

2. The water-absorbing agent according to claim 1, further satisfying (D) below:
(D) a centrifuge retention capacity (CRC) is not less than 25 g/g.

3. The water-absorbing agent according to claim 1, further satisfying (E) below:
(E) a fluid retention capacity under pressure (AAP) is not less than 20 g/g.

4. The water-absorbing agent according to claim 1, further satisfying (F) below:
(F) a water absorption speed (FSR) is not less than 0.25 g/g/s.

5. The water-absorbing agent according to claim 1, further satisfying (G) and/or (H) below:
(G) a weight average particle diameter (D50) is 300 μm to 450 μm; and
(H) a logarithmic standard deviation (GO of a particle size distribution is 0.25 to 0.45.

6. The water-absorbing agent according to claim 1, further comprising, as a liquid permeability improving agent, at least one material selected from a group consisting of a polyvalent metal cation, a cationic polymer and inorganic fine particles.

7. The water-absorbing agent according to claim 1, further comprising:

a surfactant and/or a dispersant.

8. The water-absorbing agent according to claim 1, wherein said water-absorbing agent is used for an absorbent body included in an absorbent article.

9. An absorbent article comprising: a water-absorbing agent according to claim 1.

10. The water-absorbing agent according to claim 1, wherein the gap fluid retention property under pressure is not less than 10 g/g.

* * * * *